US009220569B2

(12) United States Patent
Parihar et al.

(10) Patent No.: US 9,220,569 B2
(45) Date of Patent: Dec. 29, 2015

(54) ELECTROSURGICAL DEVICE WITH DISPOSABLE SHAFT HAVING TRANSLATING GEAR AND SNAP FIT

(71) Applicant: Ethicon Endo-Surgery, Inc., Cincinnati, OH (US)

(72) Inventors: Shailendra K. Parihar, Mason, OH (US); David T. Martin, Milford, OH (US); Gregory W. Johnson, Milford, OH (US); William J. White, West Chester, OH (US); Thomas W. Lytle, IV, Liberty Township, OH (US); Jason L. Harris, Mason, OH (US); Michael J. Stokes, Cincinnati, OH (US); Omar J. Vakharia, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 246 days.

(21) Appl. No.: 13/798,663

(22) Filed: Mar. 13, 2013

(65) Prior Publication Data

US 2014/0276761 A1    Sep. 18, 2014

(51) Int. Cl.
*A61B 19/00* (2006.01)
*A61B 18/12* (2006.01)
*A61B 18/14* (2006.01)
(Continued)

(52) U.S. Cl.
CPC ............ *A61B 19/2203* (2013.01); *A61B 18/12* (2013.01); *A61B 19/56* (2013.01); *A61B 18/1445* (2013.01); *A61B 2017/00477* (2013.01);
(Continued)

(58) Field of Classification Search
CPC ............... A61B 18/12; A61B 19/2203; A61B 2019/2211; A61B 17/072; A61B 18/1445; A61B 2018/1455
USPC ............................................ 606/34, 45, 130
See application file for complete search history.

(56) References Cited

U.S. PATENT DOCUMENTS 5,792,135 A    8/1998  Madhani et al.
5,807,378 A *  9/1998  Jensen et al. ...................... 606/1
(Continued)

FOREIGN PATENT DOCUMENTS

WO    WO 2011/109283    9/2011
WO    WO 2012/082719    6/2012

OTHER PUBLICATIONS

U.S. Appl. No. 61/550,768, filed Oct. 24, 2011.
(Continued)

*Primary Examiner* — Victor Nguyen
(74) *Attorney, Agent, or Firm* — Frost Brown Todd LLC

(57) ABSTRACT

An apparatus includes an interface assembly and a shaft assembly. The interface assembly is configured for use with a robotic system and includes a first drive assembly and a mounting plate. The mounting plate includes an opening. The first drive assembly is positioned within the opening such that the first drive assembly is laterally translatable within the opening from a first position to a second position. The shaft assembly is removably coupled with the interface assembly. The shaft assembly includes an end effector and a first coupling feature. The first drive assembly of the interface assembly actuates the end effector of the shaft assembly. The first coupling feature is longitudinally aligned with the first drive assembly. The first drive assembly engages the first coupling feature of the shaft assembly when the first drive assembly is laterally translated from the first position to the second position.

20 Claims, 79 Drawing Sheets

(51) Int. Cl.
*A61B 17/00* (2006.01)
*A61B 18/00* (2006.01)

(52) U.S. Cl.
CPC .................. *A61B2018/0063* (2013.01); *A61B 2018/00601* (2013.01); *A61B 2018/1455* (2013.01)

(56) References Cited

U.S. PATENT DOCUMENTS

| | | | |
|---|---|---|---|
| 5,817,084 | A | 10/1998 | Jensen |
| 5,878,193 | A | 3/1999 | Wang et al. |
| 6,231,565 | B1 | 5/2001 | Tovey et al. |
| 6,364,888 | B1 | 4/2002 | Niemeyer et al. |
| 6,500,176 | B1 | 12/2002 | Truckai et al. |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,380,696 | B2 | 6/2008 | Shelton, IV et al. |
| 7,381,209 | B2 | 6/2008 | Truckai et al. |
| 7,404,508 | B2 | 7/2008 | Smith et al. |
| 7,455,208 | B2 | 11/2008 | Wales et al. |
| 7,506,790 | B2 | 3/2009 | Shelton, IV et al. |
| 7,524,320 | B2 | 4/2009 | Tierney et al. |
| 7,549,564 | B2 | 6/2009 | Boudreaux |
| 7,559,450 | B2 | 7/2009 | Wales et al. |
| 7,654,431 | B2 | 2/2010 | Hueil et al. |
| 7,691,098 | B2 | 4/2010 | Wallace et al. |
| 7,780,054 | B2 | 8/2010 | Wales |
| 7,784,662 | B2 | 8/2010 | Wales et al. |
| 7,798,386 | B2 | 9/2010 | Schall et al. |
| 7,806,891 | B2 | 10/2010 | Nowlin et al. |
| 7,824,401 | B2 | 11/2010 | Manzo et al. |
| 8,021,326 | B2 | 9/2011 | Moll et al. |
| 8,461,744 | B2 | 6/2013 | Wiener et al. |
| 8,479,969 | B2 | 7/2013 | Shelton, IV et al. |
| 8,573,461 | B2 | 11/2013 | Shelton, IV et al. |
| 8,573,465 | B2 | 11/2013 | Shelton, IV |
| 8,602,288 | B2 | 12/2013 | Shelton, IV et al. |
| 8,616,431 | B2 | 12/2013 | Timm et al. |
| 8,752,749 | B2 | 6/2014 | Moore et al. |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2011/0082486 | A1 | 4/2011 | Messerly et al. |
| 2011/0087212 | A1 | 4/2011 | Aldridge et al. |
| 2011/0087213 | A1 | 4/2011 | Messerly et al. |
| 2011/0087214 | A1 | 4/2011 | Giordano et al. |
| 2011/0087215 | A1 | 4/2011 | Aldridge et al. |
| 2011/0087216 | A1 | 4/2011 | Aldridge et al. |
| 2011/0087217 | A1 | 4/2011 | Yates et al. |
| 2011/0087218 | A1 | 4/2011 | Boudreaux et al. |
| 2012/0078243 | A1 | 3/2012 | Worrell et al. |
| 2012/0078247 | A1 | 3/2012 | Worrell et al. |
| 2012/0078248 | A1 | 3/2012 | Worrell et al. |
| 2012/0116379 | A1 | 5/2012 | Yates et al. |
| 2012/0138660 | A1 | 6/2012 | Shelton, IV et al. |
| 2012/0199630 | A1 | 8/2012 | Shelton, IV et al. |
| 2012/0199632 | A1 | 8/2012 | Spivey et al. |
| 2012/0203247 | A1 | 8/2012 | Shelton, IV et al. |
| 2013/0012957 | A1 | 1/2013 | Shelton, IV et al. |
| 2013/0023868 | A1 | 1/2013 | Worrell et al. |
| 2013/0030428 | A1 | 1/2013 | Worrell et al. |
| 2013/0267969 | A1 | 10/2013 | Martin et al. |

OTHER PUBLICATIONS

U.S. Appl. No. 61/597,603, filed Feb. 10, 2012.
International Search Report dated Sep. 15, 2014 for Application No. PCT/US14/16413, 6 pages.
International Written Opinion dated Sep. 15, 2014 for Application No. PCT/US14/16413, 9 pages.

* cited by examiner

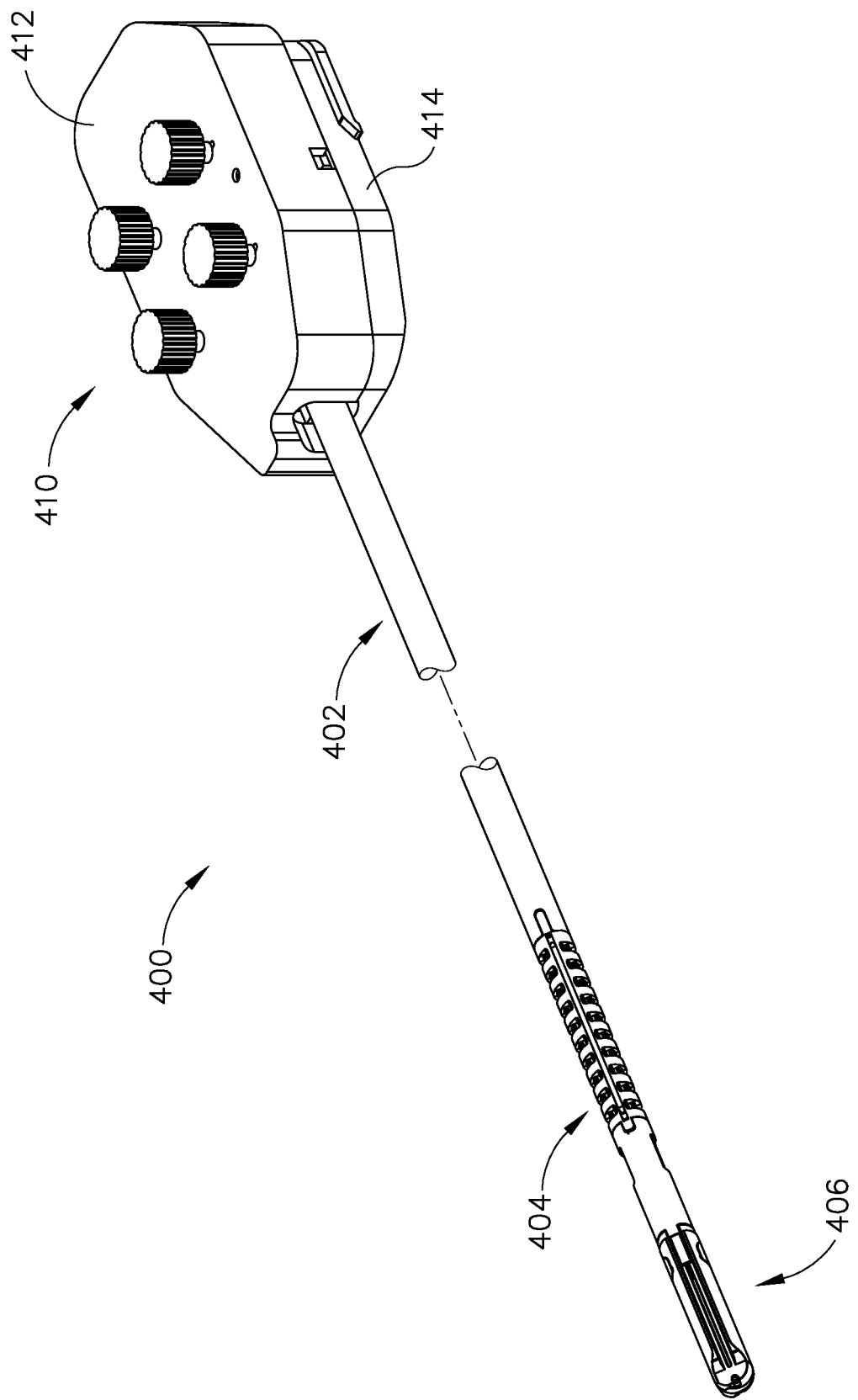

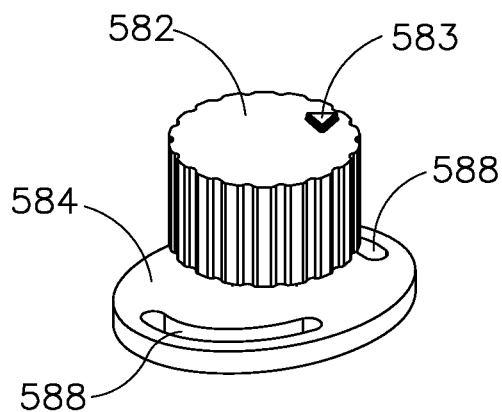
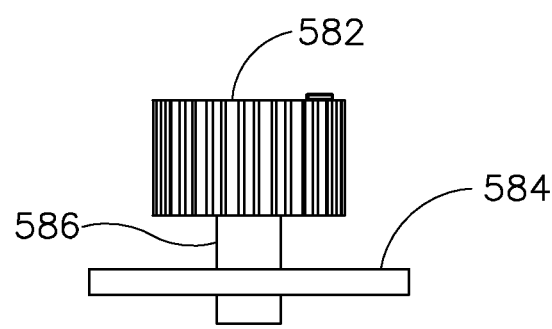
Fig.47
Fig.48
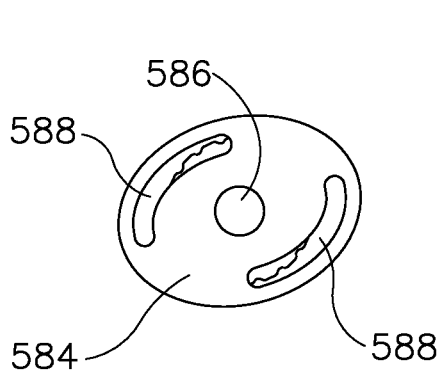
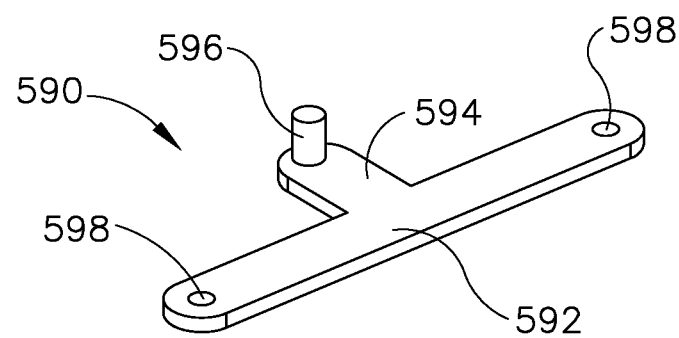
Fig.49
Fig.50

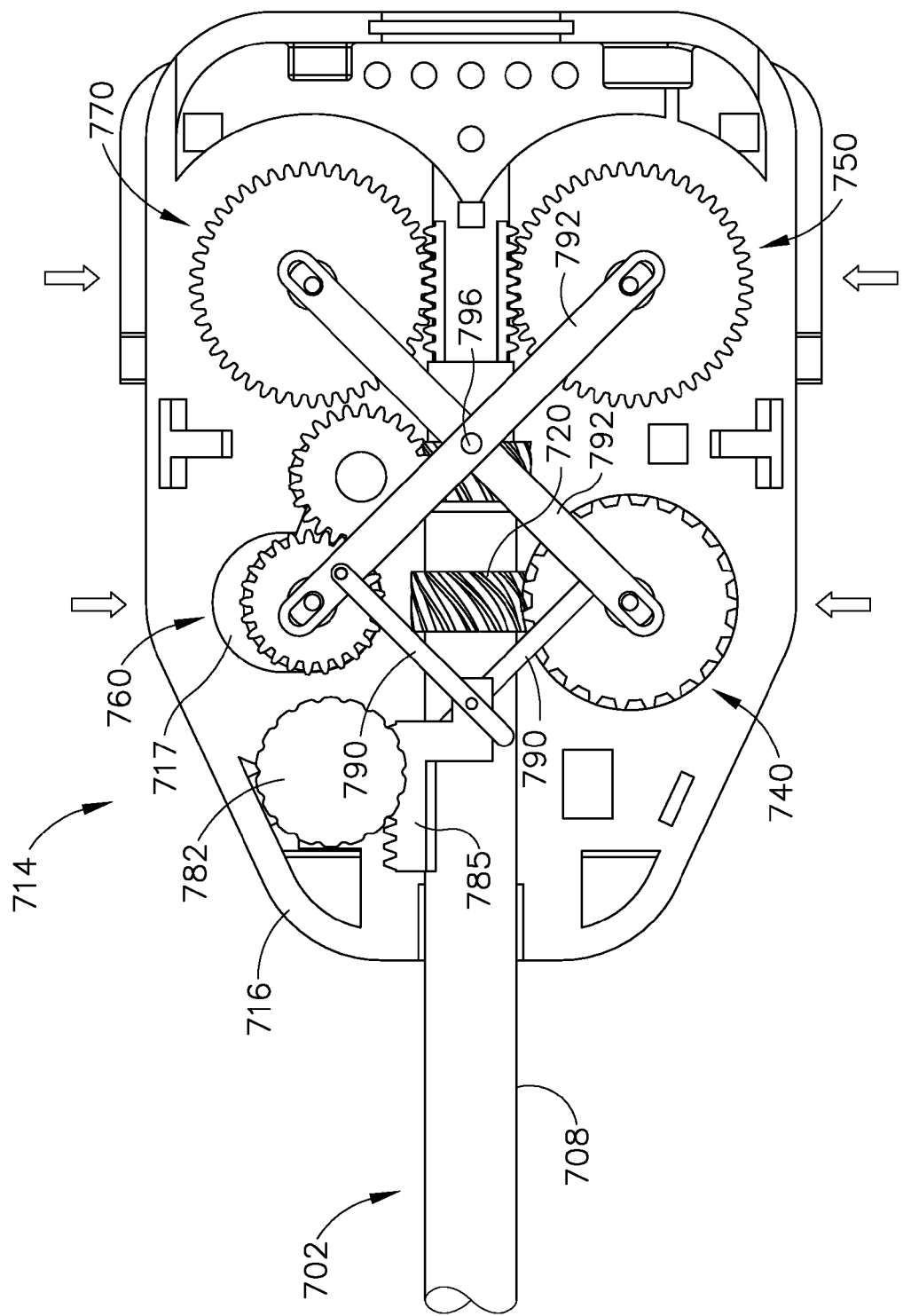

ELECTROSURGICAL DEVICE WITH DISPOSABLE SHAFT HAVING TRANSLATING GEAR AND SNAP FIT

BACKGROUND

A variety of surgical instruments include a tissue cutting element and one or more elements that transmit radio frequency (RF) energy to tissue (e.g., to coagulate or seal the tissue). An example of an RF electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013, issued as U.S. Pat. No. 9,089,327 on Jul. 28, 2015, the disclosure of which is incorporated by reference herein; and U.S. Pub. No. 2013/0023868, entitled "Surgical Instrument with Contained Dual Helix Actuator Assembly," published Jan. 31, 2013, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 20, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012, issued as U.S. Pat. No. 8,479,969 on Jul. 9, 2013; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014, the disclosure of which is incorporated by reference herein; U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein; U.S. patent application Ser. No. 13/443,101, entitled "Control Interface for Laparoscopic Suturing Instrument," filed Apr. 10, 2012, published as U.S. Pub. No. 2013/0267969 on Oct. 10, 2013, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 38 depicts a perspective view of another exemplary surgical instrument suitable for incorporation with the system of FIG. 1;

FIG. 47 depicts a perspective view of a knob assembly of the interface assembly of FIG. 46;

FIG. 48 depicts a side elevational view of the knob assembly of FIG. 47;

FIG. 49 depicts a bottom view of the knob assembly of FIG. 47;

FIG. 50 depicts a perspective view of a linkage of the interface assembly of FIG. 46;

FIG. 64B depicts a partial top view of the interface assembly of FIG. 59 in an engaged position;

Figure 1:
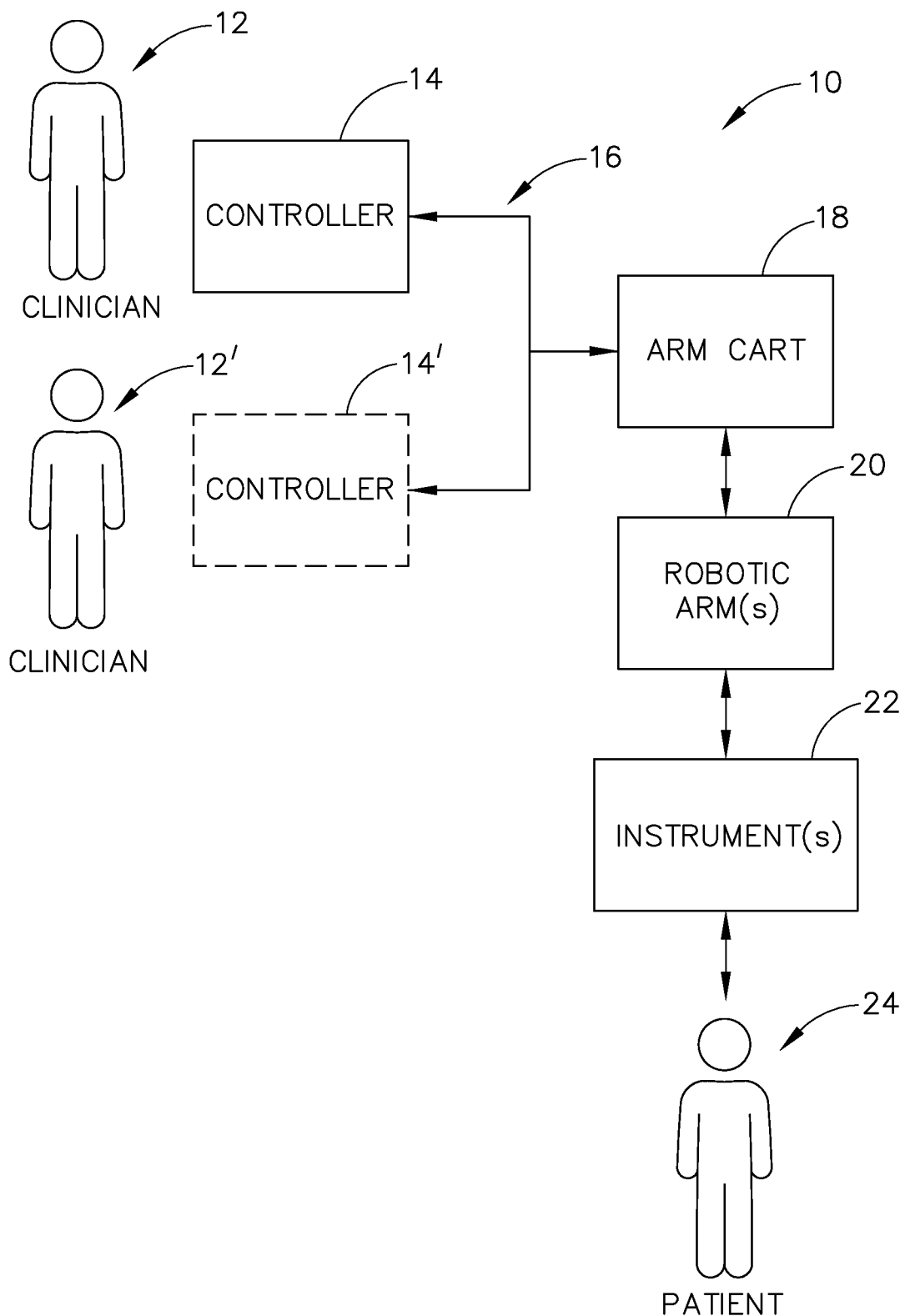
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
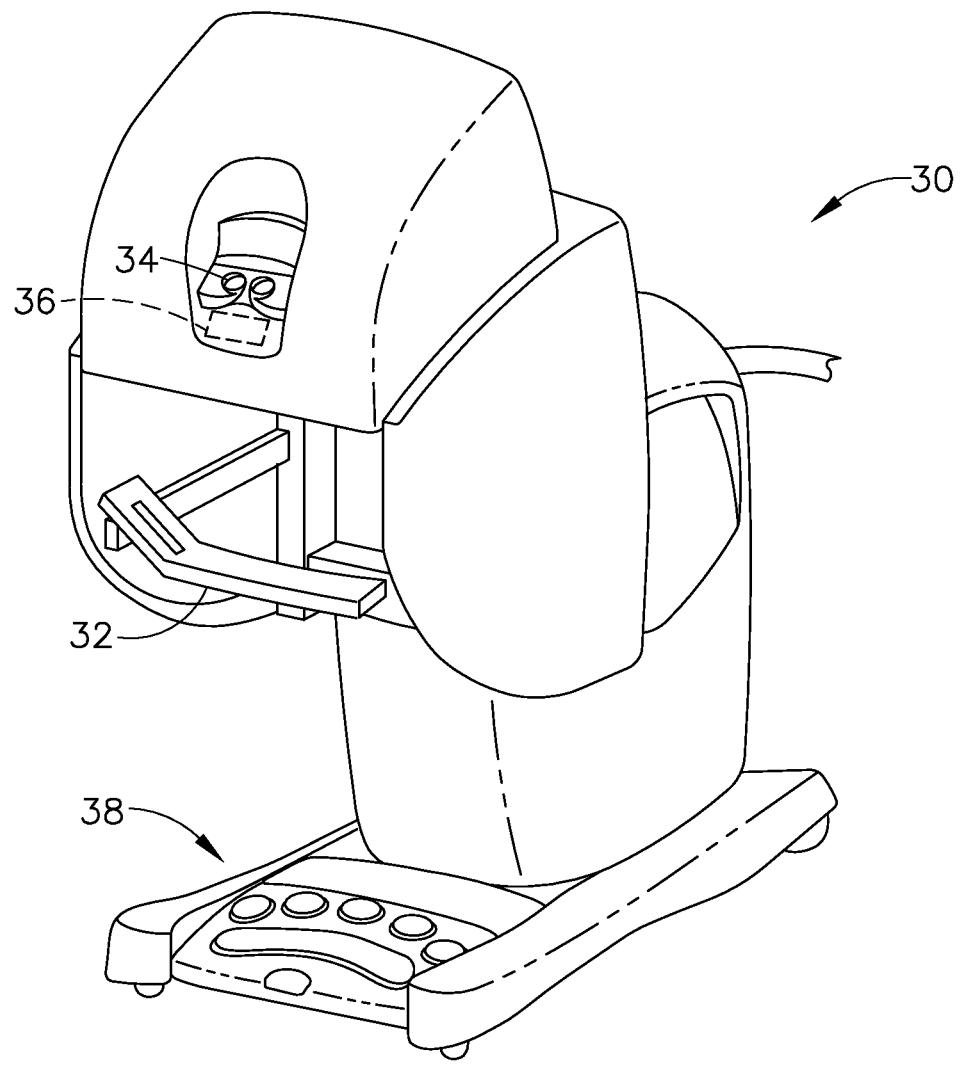
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge has been loaded into an end effector of instrument (22), whether an anvil of instrument (22) has been moved to a closed position prior to firing, and/or some other operational condition of instrument (22).

Figure 3:
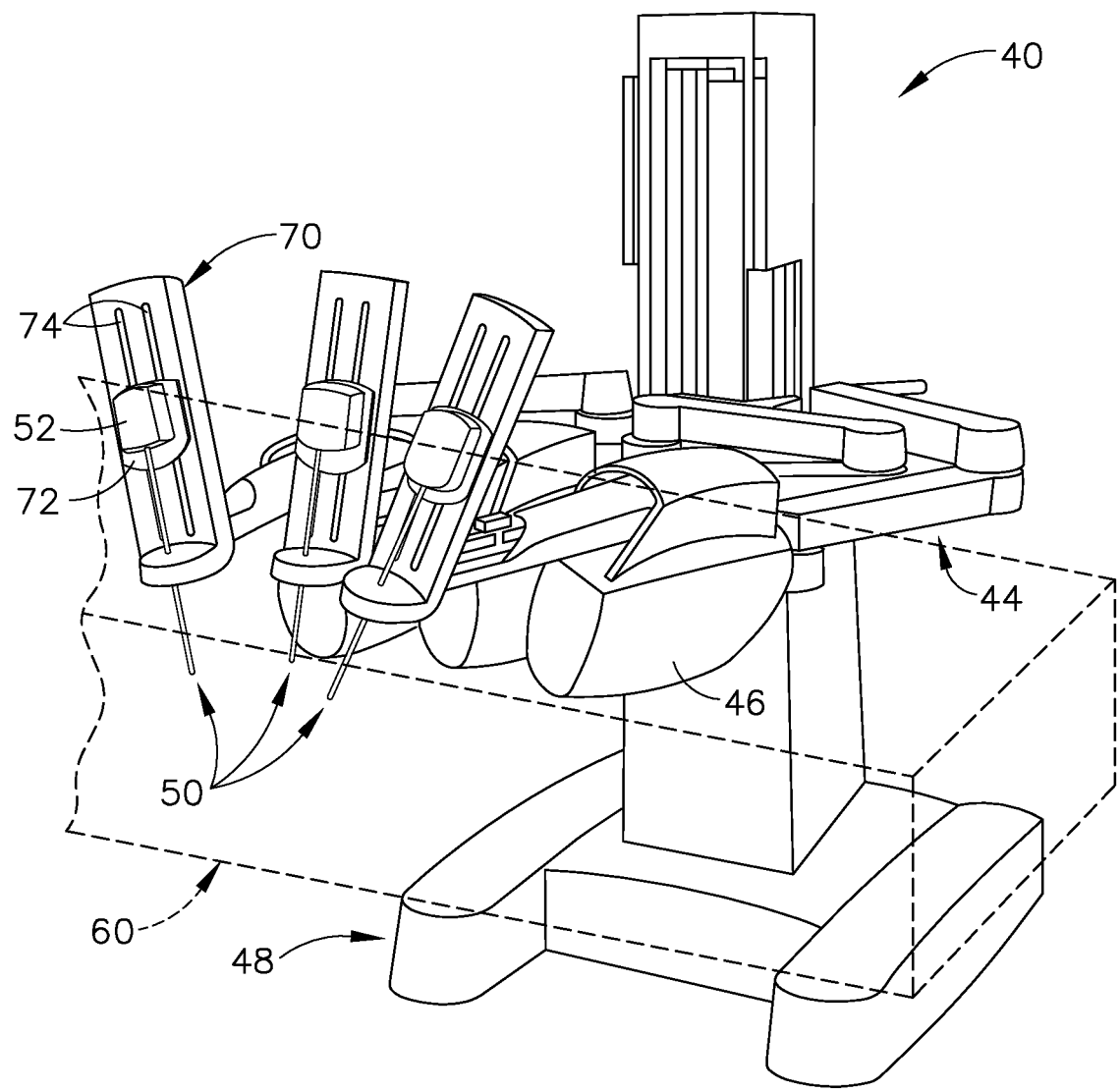
FIG. 3 depicts a perspective view of an exemplary robotic arm cart of the system of FIG. 1.
Figure 4:
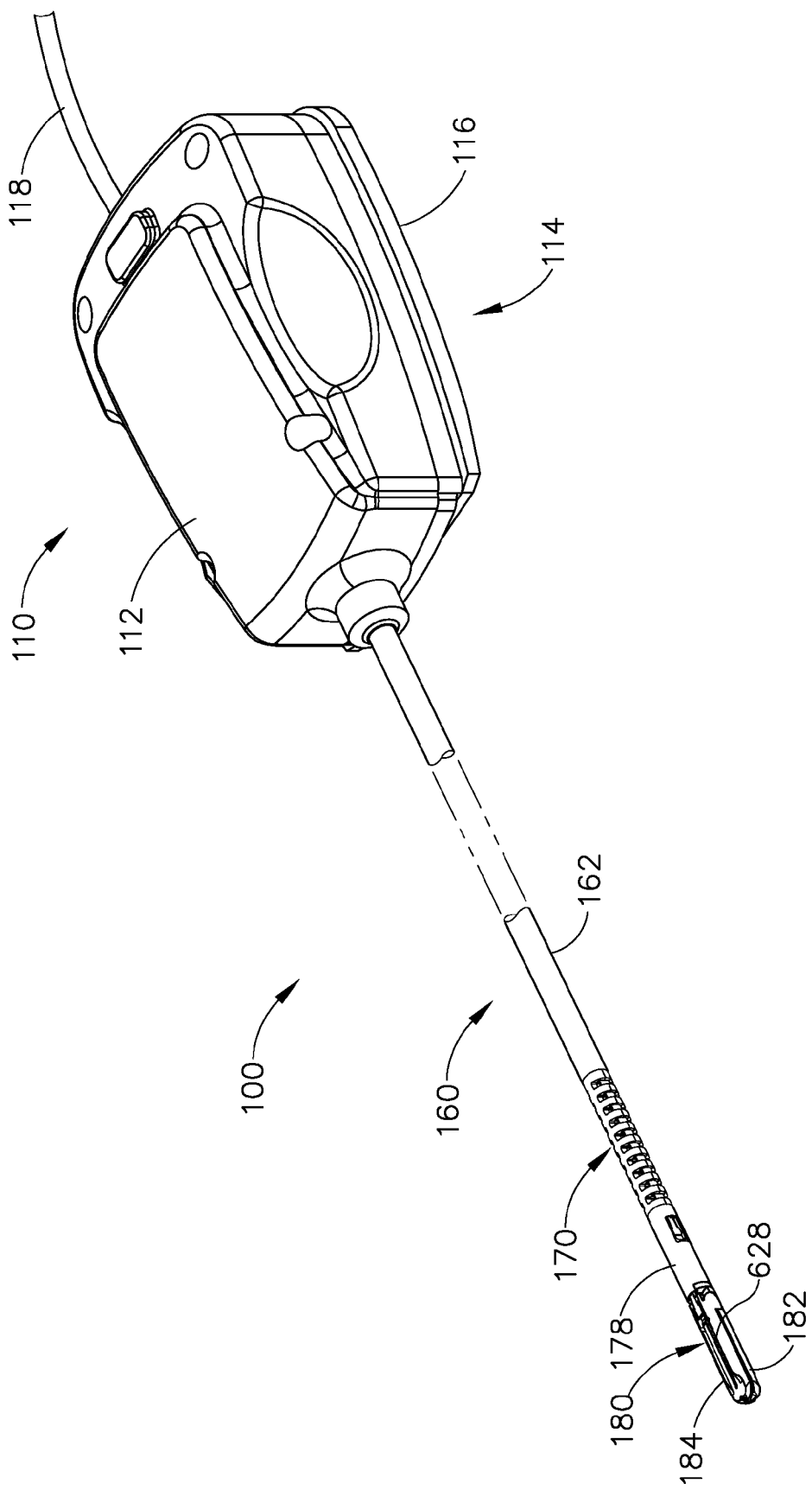
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. No. 5,792,135; U.S. Pat. No. 5,817,084; U.S. Pat. No. 5,878,193; U.S. Pat. No. 6,231,565; U.S. Pat. No. 6,783,524; U.S. Pat. No. 6,364,888; U.S. Pat. No. 7,524,320; U.S. Pat. No. 7,691,098; U.S. Pat. No. 7,806,891; U.S. Pat. No. 7,824,401; and/or U.S. Pub. No. 2013/0012957, issued as U.S. Pat. No. 8,844,789 on Sep. 30, 2014. The disclosures of each of the foregoing U.S. patents and U.S. patent Publication are incorporated by reference herein. Still other suitable features and operabilities that may be incorporated into system (10) will be apparent to those of ordinary skill in the art in view of the teachings herein.

II. Exemplary Electrosurgical Instrument with Articulation Feature

FIGS. 4-13 show an exemplary electrosurgical instrument (100) that may be used as at least one instrument (50) within system (10). At least part of instrument (100) may be constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, issued as U.S. Pat. No. 8,939,974 on Jan. 27, 2015; U.S. Pub. No. 2012/0116379; U.S. Pub. No. 2012/0078243; U.S. Pub. No. 2012/0078247; U.S. Pub. No. 2013/0030428, issued as U.S. Pat. No. 9,089,327 on Jul. 28, 2015; and/or U.S. Pub. No. 2013/0023868. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of bipolar RF energy instead of providing lines of staples to join tissue. It should also be understood that instrument (100) may have various structural and functional similarities with the ENSEAL® Tissue Sealing Device by Ethicon Endo-Surgery, Inc., of Cincinnati, Ohio. Furthermore, instrument (100) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to instrument (100), there is no intent for any of the description herein to be presumed as admitted prior art. Several teachings herein will in fact go beyond the scope of the teachings of the references cited herein and the ENSEAL® Tissue Sealing Device by Ethicon Endo-Surgery, Inc., of Cincinnati, Ohio.

Instrument (100) of the present example includes an interface assembly (110), a shaft assembly (160), an articulation section (170), and an end effector (180). Interface assembly (110) is configured to couple with a dock (72) of robotic arm cart (40) and is thereby further operable to drive articulation section (170) and end effector (180) as will be described in greater detail below. As will also be described in greater detail below, instrument (100) is operable to articulate end effector (180) to provide a desired positioning relative to tissue (e.g., a large blood vessel, etc.), then sever the tissue and apply bipolar RF energy to the tissue with end effector (180) to thereby seal the tissue.

A. Exemplary Shaft Assembly and Articulation Section

Figure 5:
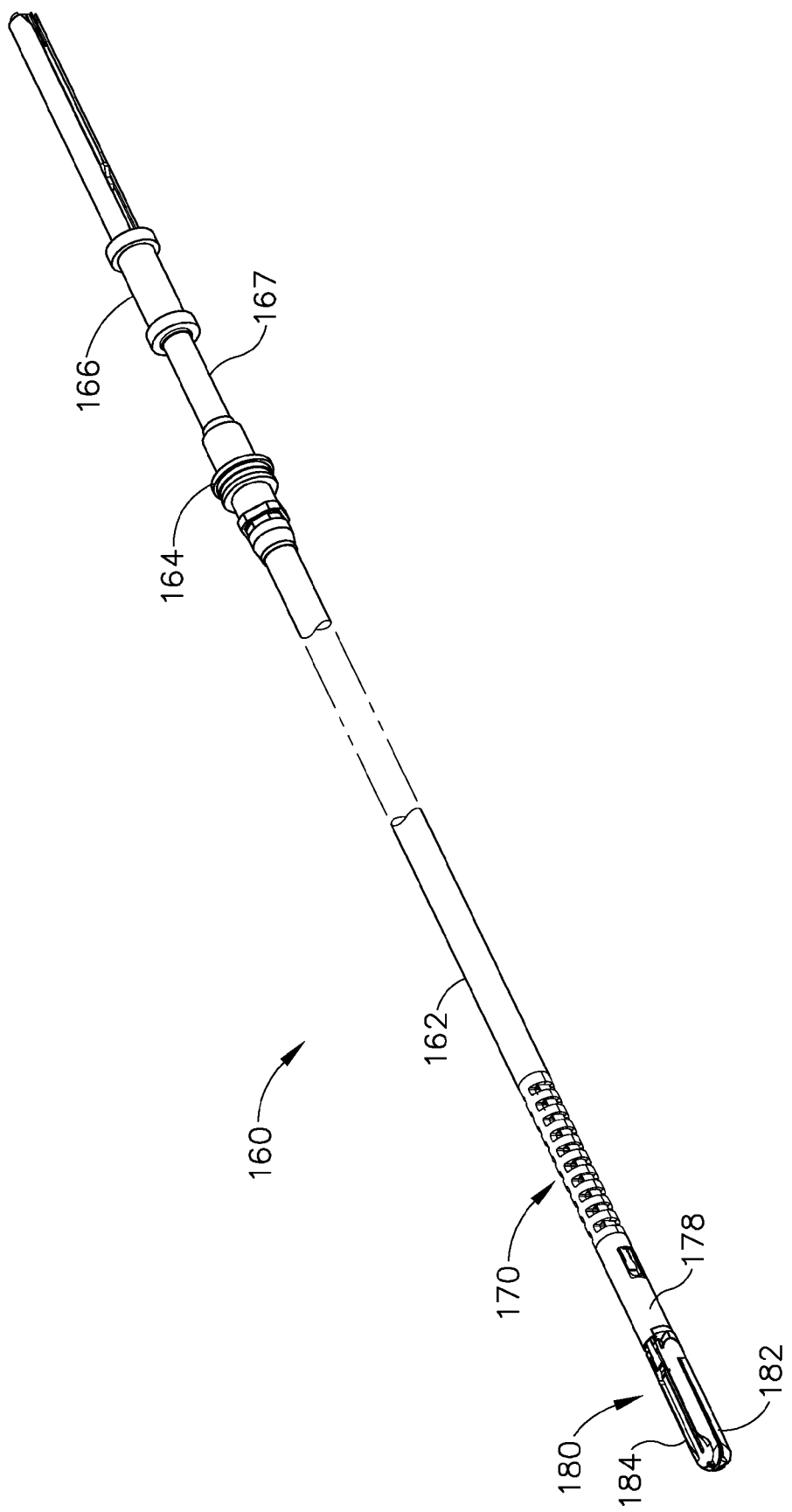
FIG. 5 depicts a perspective view of the shaft assembly of the surgical instrument of FIG. 4.

Shaft assembly (160) of the present example extends distally from interface assembly (110). Articulation section (170) is located at the distal end of shaft assembly (160), with end effector (180) being located distal to articulation section (170). Shaft assembly (160) includes an outer sheath (162) that encloses drive features and electrical features that couple interface assembly (110) with articulation section (170) and end effector (180). As best seen in FIG. 5, shaft assembly (160) further includes a unitary rotary coupling (164) and a firing beam coupling (166). Shaft assembly (160) is rotatable about the longitudinal axis defined by sheath (162), relative to interface assembly (110), via rotary coupling (164). Such rotation may provide rotation of end effector (180), articulation section (170), and shaft assembly (160) unitarily. In some other versions, rotary coupling (164) is operable to rotate end effector (180) without rotating any portion of shaft assembly (160) that is proximal of articulation section (170). As another merely illustrative example, instrument (100) may include one rotation control that provides rotatability of shaft assembly (160) and end effector (180) as a single unit; and another rotation control that provides rotatability of end effector (180) without rotating any portion of shaft assembly (160) that is proximal of articulation section (170). Other suitable rotation schemes will be apparent to those of ordinary skill in the art in view of the teachings herein. Of course, rotatable features may simply be omitted if desired.

Articulation section (170) is operable to selectively position end effector (180) at various angles relative to the longitudinal axis defined by sheath (162). Articulation section (170) may take a variety of forms. By way of example only, articulation section (170) may be configured in accordance with one or more teachings of U.S. Pub. No. 2012/0078247, the disclosure of which is incorporated by reference herein. As another merely illustrative example, articulation section (170) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (170) may take will be apparent to those of ordinary skill in the art in view of the teachings herein. It should also be understood that some versions of instrument (10) may simply lack articulation section (170).

Figure 6:
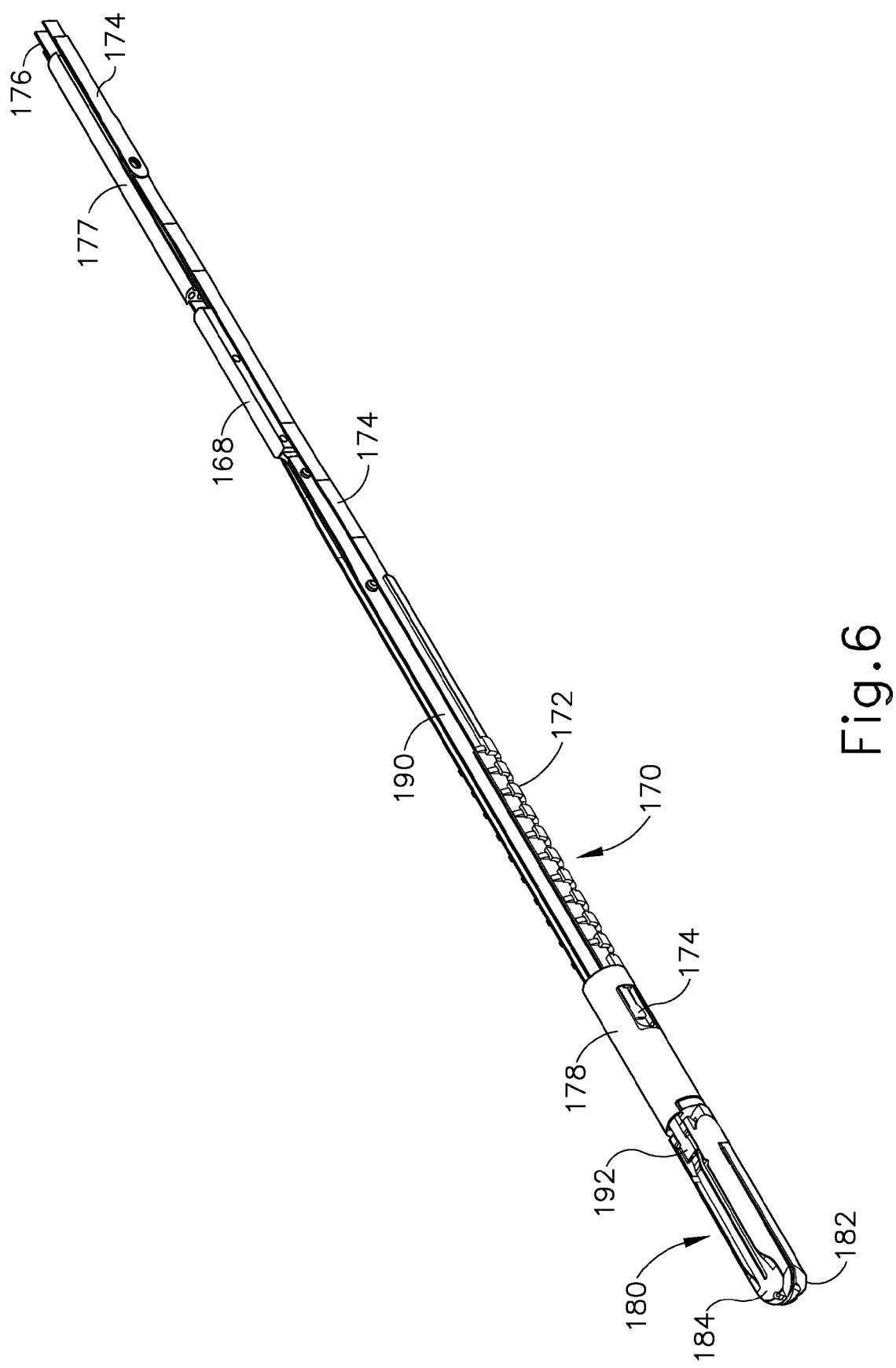
FIG. 6 depicts a perspective view of components of the shaft assembly of FIG. 5.
Figure 7:
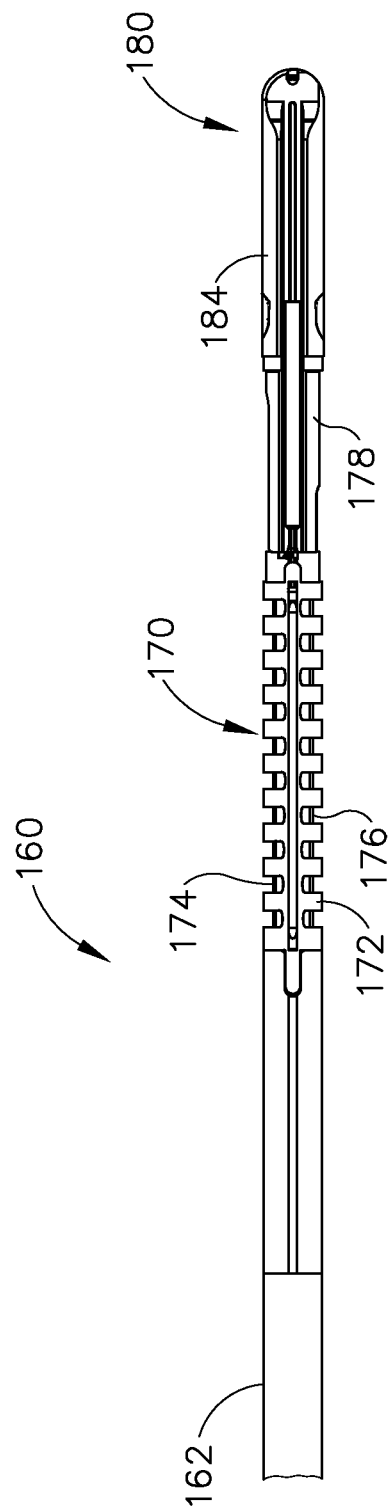
FIG. 7 depicts a top plan view of a distal portion of the shaft assembly of FIG. 5.

As best seen in FIGS. 6-7, articulation section (170) of the present example comprises a ribbed body (172) with a pair of articulation beams (174, 176) extending through ribbed body (172). An upper half of ribbed body (172) is omitted in FIG. 6. Articulation beams (174, 176) are distally anchored within a tube (178) that is positioned between end effector (180) and articulation section (170). Articulation beams (174, 176) are operable to articulate end effector (180) by laterally deflecting end effector (180) away from the longitudinal axis defined by sheath (162). In particular, and referring to the view shown in FIG. 7, end effector (180) will deflect toward articulation beam (174) when articulation beam (174) is retracted proximally while articulation beam (176) is advanced distally. End effector (180) will deflect toward articulation beam (176) when articulation beam (176) is retracted proximally while articulation beam (174) is advanced distally. Merely illustrative examples of how articulation beams (174, 176) may be opposingly translated will be described in greater detail below, while still other examples will be apparent to those of ordinary skill in the art in view of the teachings herein. As best seen in FIG. 6, a spacer body (177) is positioned between articulation beams (174, 176) and is operable to maintain beams (174, 176) in a substantially straight, separated relationship.

B. Exemplary End Effector

End effector (180) of the present example comprises a first jaw (182) and a second jaw (184). In the present example, first jaw (182) is substantially fixed relative to shaft assembly (160); while second jaw (184) pivots relative to shaft assembly (160), toward and away from first jaw (182). In some versions, actuators such as rods or cables, etc., may extend through sheath (162) and be joined with second jaw (184) at a pivotal coupling, such that longitudinal movement of the actuator rods/cables/etc. through shaft assembly (160) provides pivoting of second jaw (184) relative to shaft assembly (160) and relative to first jaw (182). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (190), such that actuator rods/cables/etc. may simply be eliminated in some versions.

Figure 8:
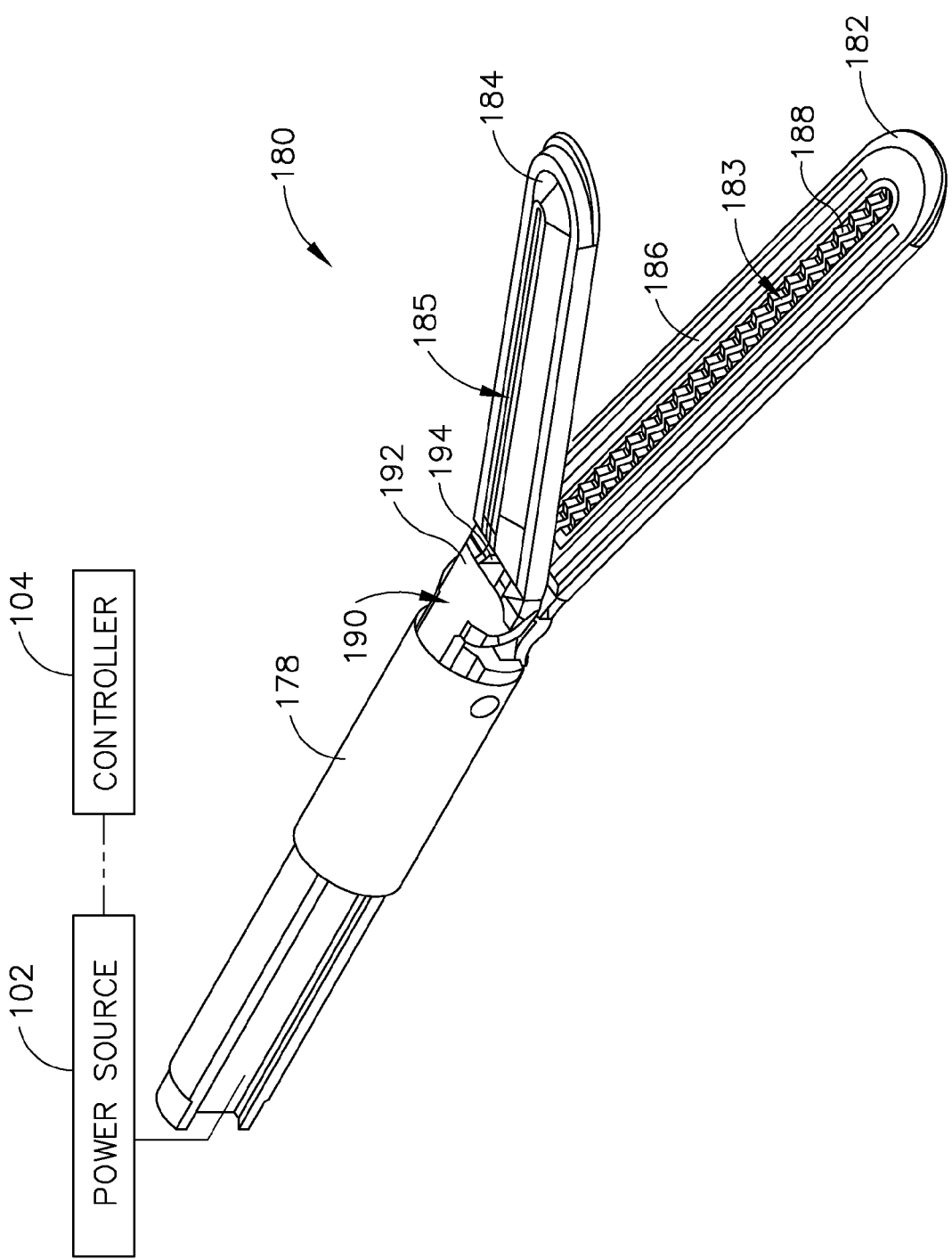
FIG. 8 depicts a perspective view of the end effector of the shaft assembly of FIG. 5, in an open configuration.
Figure 9:
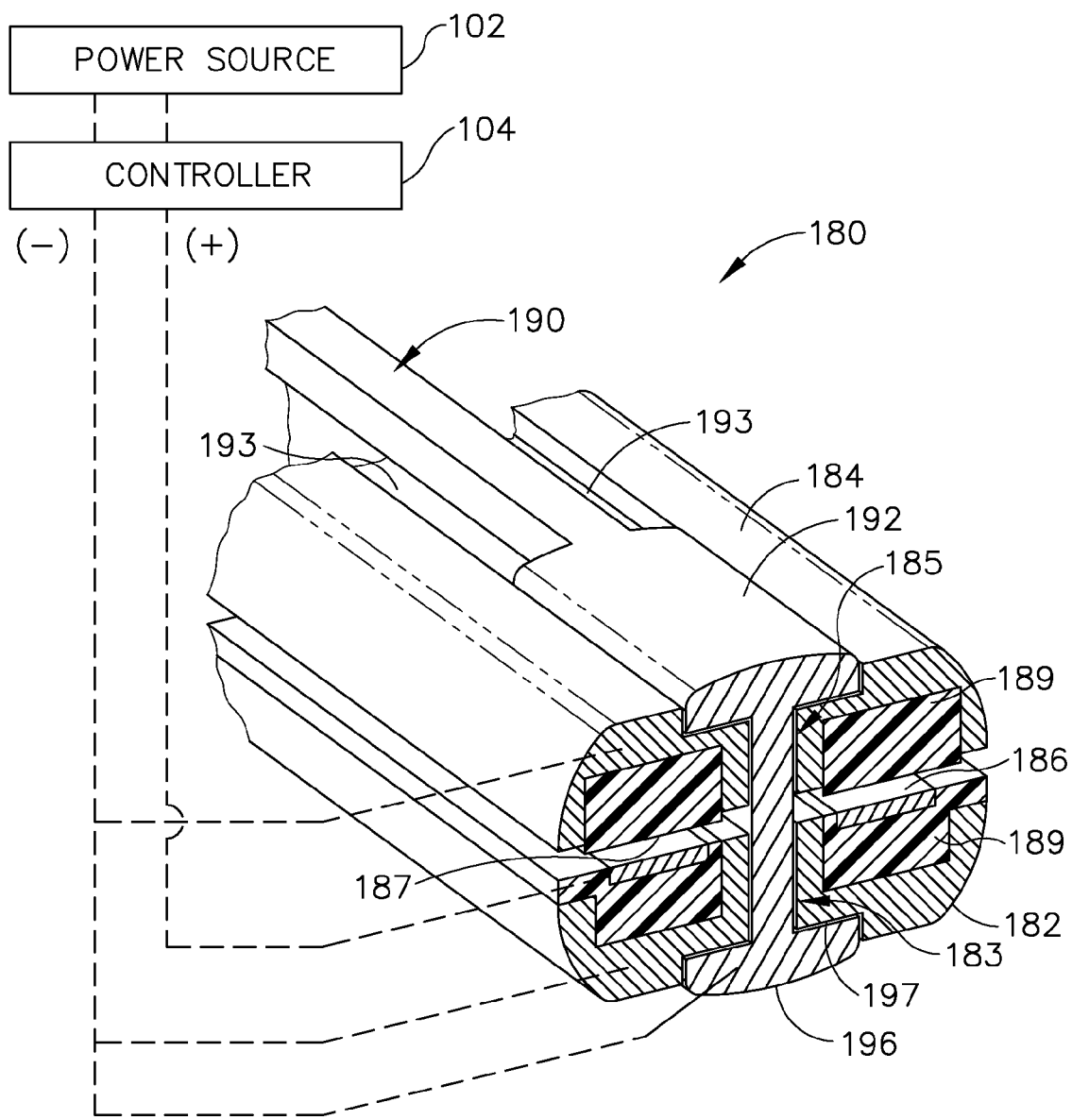
FIG. 9 depicts a perspective view in cross-section of the end effector of FIG. 8, taken along a lateral plane, with the end effector in a closed configuration.

As best seen in FIGS. 8-9, first jaw (182) defines a longitudinally extending elongate slot (183); while second jaw (184) also defines a longitudinally extending elongate slot (185). In addition, the top side of first jaw (182) presents a first electrode surface (186); while the underside of second jaw (184) presents a second electrode surface (187). Electrode surfaces (186, 187) are in communication with an electrical source (102) via one or more conductors (not shown) that extend along the length of shaft assembly (160). Electrical source (102) is operable to deliver RF energy to first electrode surface (186) at a first polarity and to second electrode surface (187) at a second (opposite) polarity, such that RF current flows between electrode surface (186, 187) and thereby through tissue captured between jaws (182, 184). In some versions, firing beam (190) serves as an electrical conductor that cooperates with electrode surface (186, 187) (e.g., as a ground return) for delivery of bipolar RF energy captured between jaws (182, 184).

Electrical source (102) may be external to instrument (100) or may be integral with instrument (100), as described in one or more references cited herein or otherwise. A controller (104) regulates delivery of power from electrical source (102) to electrode surfaces (186, 187). Controller (104) may also be external to instrument (100) or may be integral with electrosurgical instrument (100), as described in one or more references cited herein or otherwise. It should also be understood that electrode surfaces (186, 187) may be provided in a variety of alternative locations, configurations, and relationships. It should also be understood that power source (102) and/or controller (104) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, issued as U.S. Pat. No. 9,089,360 on Jul. 28, 2015, the disclosure of which is incorporated by reference herein; U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, issued as U.S. Pat. No. 8,951,248 on Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, issued as U.S. Pat. No. 9,039,695 on May 26, 2015, the disclosure of which is incorporated by reference herein; U.S. Pub. No. 2011/0087215, entitled "Surgical Generator for Ultrasonic and Electrosurgical Devices," published Apr. 14, 2011, issued as U.S. Pat. No. 9,050,093 on Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, issued as U.S. Pat. No. 8,956,349 on Feb. 17, 2015, the disclosure of which is incorporated by reference herein; and/or U.S. Pub. No. 2011/0087217, entitled "Surgical Generator for Ultrasonic and Electrosurgical Devices," published Apr. 14, 2011, issued as U.S. Pat. No. 9,060,776 on Jun. 23, 2015, the disclosure of which is incorporated by reference herein. Other suitable configurations for power source (102) and controller (104) will be apparent to those of ordinary skill in the art in view of the teachings herein.

As best seen in FIG. 9, the lower side of first jaw (182) includes a longitudinally extending recess (197) adjacent to slot (183); while the upper side of second jaw (184) includes a longitudinally extending recess (193) adjacent to slot (185). FIG. 2 shows the upper side of first jaw (182) including a plurality of teeth serrations (188). It should be understood that the lower side of second jaw (184) may include complementary serrations that nest with serrations (188), to enhance gripping of tissue captured between jaws (182, 184) without necessarily tearing the tissue. Of course, serrations (188) may take any other suitable form or may be simply omitted altogether. It should also be understood that serrations (188) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (182, 184).

With jaws (182, 184) in a closed position, shaft assembly (160) and end effector (180) are sized and configured to fit through trocars having various inner diameters, such that instrument (100) is usable in minimally invasive surgery, though of course instrument (100) could also be used in open procedures if desired. By way of example only, with jaws (182, 184) in a closed position, shaft assembly (160) and end effector (180) may present an outer diameter of approximately 5 mm. Alternatively, shaft assembly (160) and end effector (180) may present any other suitable outer diameter (e.g., between approximately 2 mm and approximately 20 mm, etc.).

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (189) (e.g., PTC polymer, etc.), located adjacent to electrodes (186, 187) and/or elsewhere. Data from sensors may be communicated to controller (104). Controller (104) may process such data in a variety of ways. By way of example only, controller (104) may modulate or otherwise change the RF energy being delivered to electrode surface (186, 187), based at least in part on data acquired from one or more sensors at end effector (180). In addition or in the alternative, controller (104) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (104), and may simply provide a purely localized effect at end effector (180). For instance, PTC thermistor bodies (189) at end effector (180) may automatically reduce the energy delivery at electrode surface (186, 187) as the temperature of the tissue and/or end effector (180) increases, thereby reducing the likelihood of overheating. In some such versions, a PTC thermistor element is in series with power source (102) and electrode surface (186, 187); and the PTC thermistor provides an increased impedance (reducing flow of current) in response to temperatures exceeding a threshold. Furthermore, it should be understood that electrode surface (186, 187) may be used as sensors (e.g., to sense tissue impedance, etc.). Various kinds of sensors that may be incorporated into instrument (100) will be apparent to those of ordinary skill in the art in view of the teachings herein. Similarly various things that can be done with data from sensors, by controller (104) or otherwise, will be apparent to those of ordinary skill in the art in view of the teachings herein. Other suitable variations for end effector (180) will also be apparent to those of ordinary skill in the art in view of the teachings herein.

Firing beam (190) is longitudinally movable along part of the length of end effector (180). Firing beam (190) is coaxially positioned within shaft assembly (160), extends along part of the length of shaft assembly (160), and translates longitudinally within shaft assembly (160) (including articulation section (170) in the present example), though it should be understood that firing beam (190) and shaft assembly (160) may have any other suitable relationship. As shown in FIG. 6, firing beam (190) is secured to a firing block (168), such that firing beam (190) and firing block (168) translate unitarily together within sheath (162). Firing block (168) is secured to firing tube (167), which is best seen in FIG. 5. Firing block (168) and firing tube (167) translate unitarily together within sheath (162). Firing beam coupling (166) is secured to firing tube (167), such that translating firing beam coupling (166) will translate firing beam (190) through the above-described couplings.

Firing beam (190) includes a sharp distal blade (194), an upper flange (192), and a lower flange (196). As best seen in FIGS. 8-9, distal blade (194) extends through slots (183, 185) of jaws (182, 184), with upper flange (192) being located above jaw (184) in recess (59) and lower flange (196) being located below jaw (182) in recess (58). The configuration of distal blade (194) and flanges (62, 66) provides an "I-beam" type of cross section at the distal end of firing beam (190). While flanges (192, 196) extend longitudinally only along a small portion of the length of firing beam (190) in the present example, it should be understood that flanges (192, 196) may extend longitudinally along any suitable length of firing beam (190). In addition, while flanges (192, 196) are positioned along the exterior of jaws (182, 184), flanges (192, 196) may alternatively be disposed in corresponding slots formed within jaws (182, 184). For instance, each jaw (182, 184) may define a "T"-shaped slot, with parts of distal blade (194) being disposed in one vertical portion of each "T"-shaped slot and with flanges (192, 196) being disposed in the horizontal portions of the "T"-shaped slots. Various other suitable configurations and relationships will be apparent to those of ordinary skill in the art in view of the teachings herein.

Distal blade (194) is substantially sharp, such that distal blade (194) will readily sever tissue that is captured between jaws (182, 184). Distal blade (194) is also electrically grounded in the present example, providing a return path for RF energy as described elsewhere herein. In some other versions, distal blade (194) serves as an active electrode. In addition or in the alternative, distal blade (194) may be selectively energized with ultrasonic energy (e.g., harmonic vibrations at approximately 55.5 kHz, etc.).

The "I-beam" type of configuration of firing beam (190) provides closure of jaws (182, 184) as firing beam (190) is advanced distally. In particular, flange (192) urges jaw (184) pivotally toward jaw (182) as firing beam (190) is advanced from a proximal position to a distal position, by bearing against recess (193) formed in jaw (184). This closing effect on jaws (182, 184) by firing beam (190) may occur before distal blade (194) reaches tissue captured between jaws (182, 184). Such staging of encounters by firing beam (190) may reduce the force required to actuate firing beam (190) distally through a full firing stroke. In other words, in some such versions, firing beam (190) may have already overcome an initial resistance required to substantially close jaws (182, 184) on tissue before encountering resistance from severing the tissue captured between jaws (182, 184). Of course, any other suitable staging may be provided.

In the present example, flange (192) is configured to cam against a ramp feature at the proximal end of jaw (184) to open jaw (184) when firing beam (190) is retracted to a proximal position and to hold jaw (184) open when firing beam (190) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (190) is translated in the present example, it should be understood that other versions may provide independent movement of jaws (182, 184) and firing beam (190). By way of example only, one or more cables, rods, beams, or other features may extend through shaft assembly (160) to selectively actuate jaws (182, 184) independently of firing beam (190).

C. Exemplary Robotic Arm Interface Assembly

FIGS. 4 and 10-13 show interface assembly (110) of the present example in greater detail. As shown, interface assembly (110) comprises a housing (112), a base (114), and a cable (118). Housing (112) comprises a shell that simply encloses drive components. In some versions, housing (112) also includes an electronic circuit board, chip, and/or other feature that is configured to identify instrument (100). Such identification may be carried out through cable (118). Cable (118) is configured to couple with power source (102) and controller (104). A strain relief (119) is provided at the interface of cable (118) and housing (112). It should be noted that housing (112) is omitted from FIGS. 11-13 for the sake of clarity.

Figure 10:
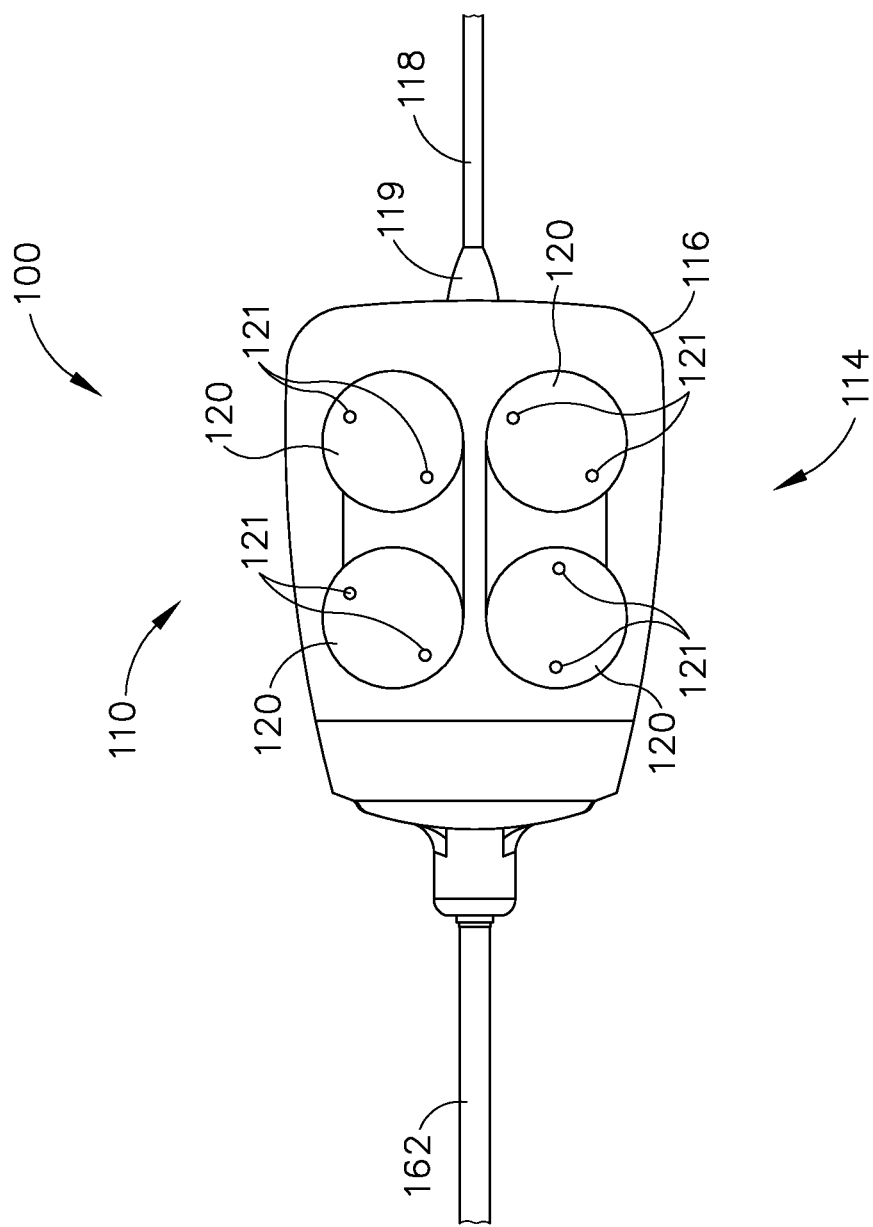
FIG. 10 depicts a bottom plan view of a proximal portion of the instrument of FIG. 4.
Figure 11:
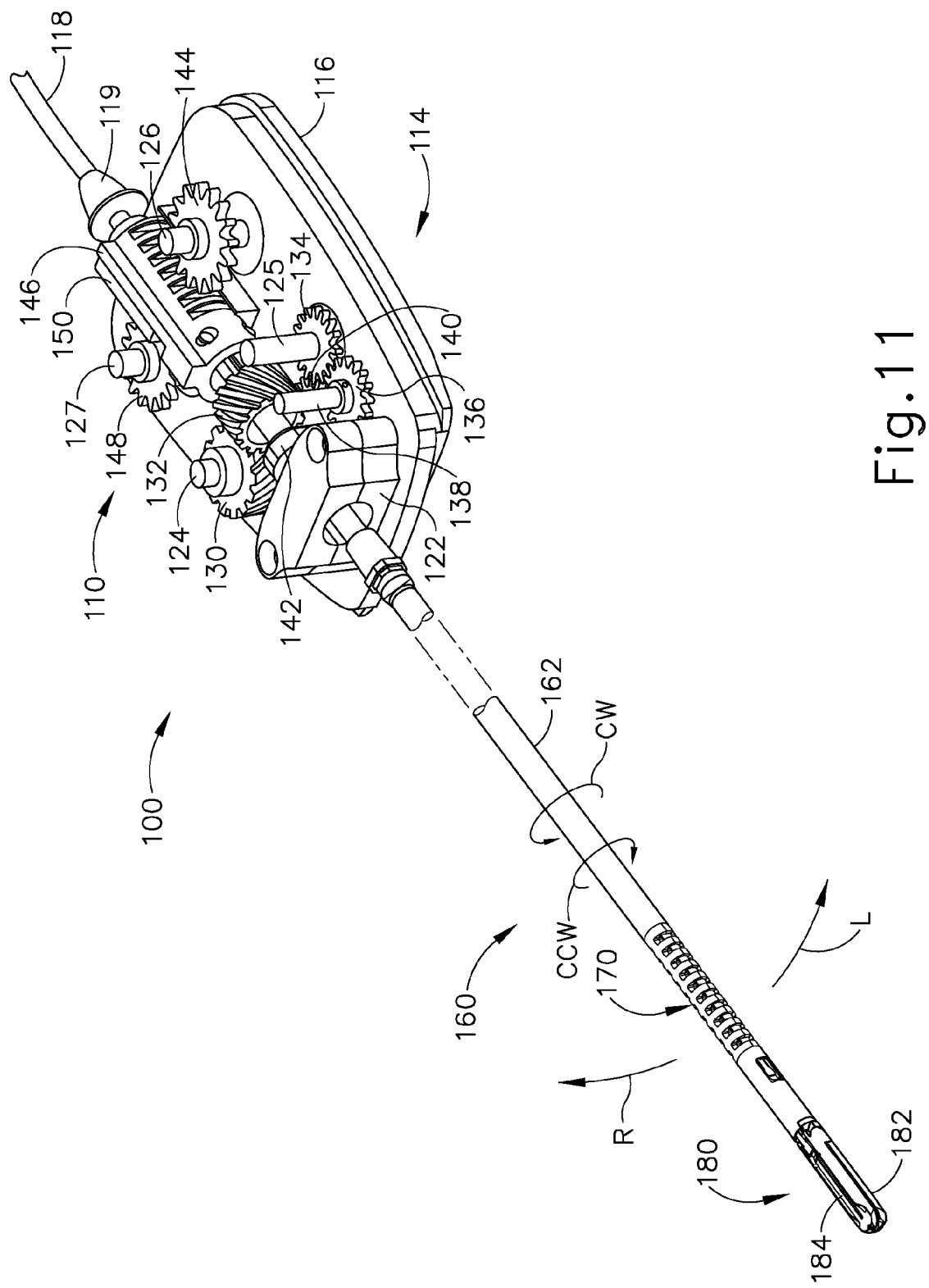
FIG. 11 depicts a perspective view of the instrument of FIG. 4, with a top cover removed.
Figure 12:
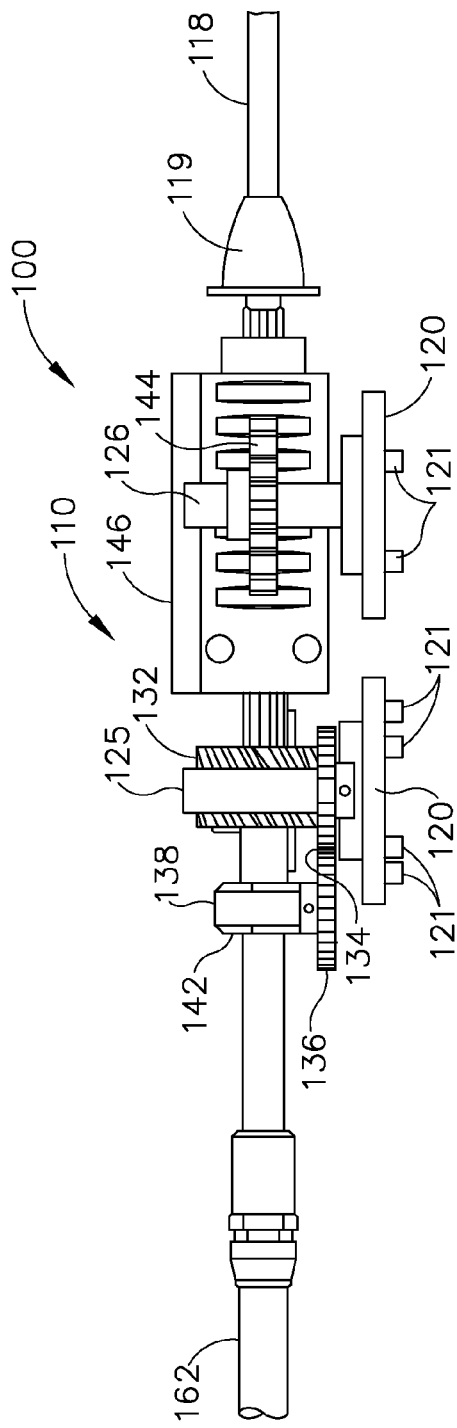
FIG. 12 depicts a left side elevational view of the instrument of FIG. 4, with the top cover removed.
Figure 13:
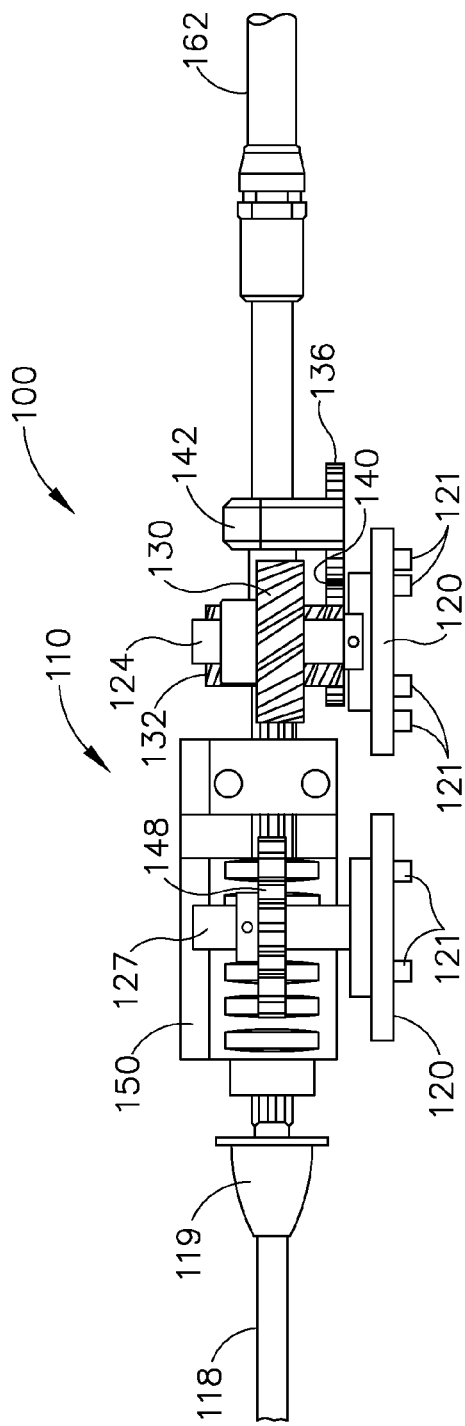
FIG. 13 depicts a right side elevational view of the instrument of FIG. 4, with the top cover removed.

Base (114) includes a mounting plate (116) that engages dock (72) of robotic arm cart (40). It should be noted that plate (116) is omitted from FIGS. 12-13 for the sake of clarity. While not shown, it should be understood that base (114) may also include one or more electrical contacts and/or other features operable to establish electrical communication with a complementary feature of dock (72). A shaft support structure (122) extends upwardly from base (114) and provides support to shaft assembly (160) (while still allowing shaft assembly (160) to rotate). By way of example only, shaft support structure (122) may include a busing, bearings, and/or other features that facilitate rotation of shaft assembly (160) relative to support structure (122). As shown in FIG. 10, base (114) further includes four drive discs (120) that are rotatable relative to plate (116). Each disc (120) includes a pair of unitary pins (121) that couple with complementary recesses (not shown) in drive elements of dock (72). In some versions, one pin (121) of each pair is closer to the axis of rotation of the corresponding disc (120), to ensure proper angular orientation of disc (120) relative to the corresponding drive element of dock (72). As best seen in FIGS. 11-13, a drive shaft (124, 125, 126, 127) extends unitarily upwardly from each disc (120). As will be described in greater detail below, discs (120) are operable to provide independent rotation of shaft assembly (160), bending of articulation section (170), and translation of firing beam (190), through rotation of drive shafts (124, 125, 126, 127).

As best seen in FIG. 11, a first helical gear (130) is fixedly secured to drive shaft (124), such that rotation of the corresponding disc (120) provides rotation of first helical gear (130). First helical gear (130) meshes with a second helical gear (132), which is fixedly secured to rotary coupling (164). Thus, rotation of first helical gear (130) provides rotation of shaft assembly (160). It should be understood that rotation of first helical gear (130) about a first axis is converted into rotation of second helical gear (132) about a second axis, which is orthogonal to the first axis. A clockwise (CW) rotation of second helical gear (132) results in CW rotation of shaft assembly (160). A counter-clockwise (CCW) rotation of second helical gear (132) results in CCW rotation of shaft assembly (160). Other suitable ways in which shaft assembly (160) may be rotated will be apparent to those of ordinary skill in the art in view of the teachings herein.

As best seen in FIGS. 11-12, a spur gear (134) is fixedly secured to drive shaft (125), such that rotation of the corresponding disc (120) provides rotation of spur gear (134). Spur gear (134) meshes with a first spur pinion (136), which is fixedly secured to a pinion shaft (138). Pinion shaft (138) is supported by base (116) and rotates freely relative to base (116), such that first spur pinion (136) is rotatable as an idler. It should therefore be understood that first spur pinion (136) rotates in response to rotation of spur gear (134). First spur pinion (136) also meshes with a rack (140), which is fixedly secured to a drive block (142). Drive block (142) is secured to firing beam coupling (166). Thus, rotation of first spur pinion (136) is converted to translation of firing beam (190) via rack (140), drive block (142), and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (125) via its corresponding disc (120). When this rotation is reversed, firing beam (190) retracts proximally, ultimately opening jaws (182, 184) to release tissue. Other suitable ways in which firing beam (190) may be translated will be apparent to those of ordinary skill in the art in view of the teachings herein.

With respect to articulation control, FIGS. 11-12 show a second spur pinion (144) fixedly secured to drive shaft (126), such that rotation of the corresponding disc (120) provides rotation of second spur pinion (144). Second spur pinion (144) meshes with a left rack (146), which is fixedly secured to articulation beam (174). It should be understood that articulation beam (174) will translate distally or proximally in response to rotation of drive shaft (126). Similarly, FIGS. 11 and 13 show a third spur pinion (148) fixedly secured to drive shaft (127), such that rotation of the corresponding disc (120) provides rotation of third spur pinion (148). Third spur pinion (148) meshes with a right rack (150), which is fixedly secured to articulation beam (176). It should be understood that articulation beam (176) will translate distally or proximally in response to rotation of drive shaft (127).

It should also be understood that drive shafts (126, 127) may be rotated in the same direction simultaneously in order to provide opposing translation of beams (174, 176). For instance, drive shaft (126) may be rotated clockwise to retract beam (174) proximally, with drive shaft (127) being rotated clockwise to advance beam (176) distally, to thereby deflect end effector (180) to the left (L) at articulation section (170). Conversely, drive shaft (126) may be rotated counter-clockwise to advance beam (174) distally, with drive shaft (127) being rotated counter-clockwise to retract beam (176) proximally, to deflect end effector (180) to the left (R) at articulation section (170). Other suitable ways in which end effector (180) may be articulated at articulation section (170) will be apparent to those of ordinary skill in the art in view of the teachings herein. By way of example only, articulation control may be provided in accordance with at least some of the teachings of U.S. Pub. No. 2012/0078243, the disclosure of which is incorporated by reference herein; and/or U.S. Pub. No. 2013/0023868, the disclosure of which is incorporated by reference herein. It should also be understood that some versions of instrument (100) may simply lack an articulation section (170) and corresponding control.

D. Exemplary Operation

In an exemplary use, arm cart (40) is used to insert end effector (180) into a patient via a trocar. Articulation section (170) is substantially straight when end effector (180) and part of shaft assembly (160) are inserted through the trocar. Drive shaft (124) may be rotated through drive features in dock (72) that are coupled with the corresponding disc (120), to position end effector (180) at a desired angular orientation relative to the tissue. Drive shafts (126, 126) may then be rotated through drive features in dock (72) that are coupled with the corresponding discs (120), to pivot or flex articulation section (170) of shaft assembly (160) in order to position end effector (180) at a desired position and orientation relative to an anatomical structure within the patient. Two layers of tissue of the anatomical structure are then captured between jaws (182, 184) by rotating drive shaft (125) to advance firing beam (190) distally through a first range of motion. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of instrument (100) is perpendicular to the longitudinal axis defined by end effector (180), etc.). In other words, the lengths of jaws (182, 184) may be oriented perpendicular to (or at least generally transverse to) the length of the blood vessel. As noted above, flanges (192, 196) cammingly act to pivot jaw (182) toward jaw (184) when firing beam (190) is actuated distally by rotating drive shaft (125).

With tissue layers captured between jaws (182, 184) firing beam (190) continues to advance distally in response to continued rotation of drive shaft (125). As firing beam (190) continues to advance distally, distal blade (194) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (192, 196) immediately above and below jaws (182, 184), respectively, may help keep jaws (182, 184) in a closed and tightly clamping position. In particular, flanges (192, 196) may help maintain a significantly compressive force between jaws (182, 184). With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). In some versions, electrodes (186, 187) are selectively coupled with power source (102) such that electrode surface (186, 187) of jaws (182, 184) are activated with a common first polarity while firing beam (190) is activated at a second polarity that is opposite to the first polarity. Thus, a bipolar RF current flows between firing beam (190) and electrode surfaces (186, 187) of jaws (182, 184), through the compressed regions of severed tissue layer portions. In some other versions, electrode surface (186) has one polarity while electrode surface (187) and firing beam (190) both have the other polarity. In either version (among at least some others), bipolar RF energy delivered by power source (102) ultimately thermally welds the tissue layer portions on one side of firing beam (190) together and the tissue layer portions on the other side of firing beam (190) together.

In certain circumstances, the heat generated by activated electrode surfaces (186, 187) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surface (186, 187) may be activated with bipolar RF energy before firing beam (190) even begins to translate distally and thus before the tissue is even severed. Other suitable ways in which instrument (100) may be operable and operated will be apparent to those of ordinary skill in the art in view of the teachings herein.

Figure 14:
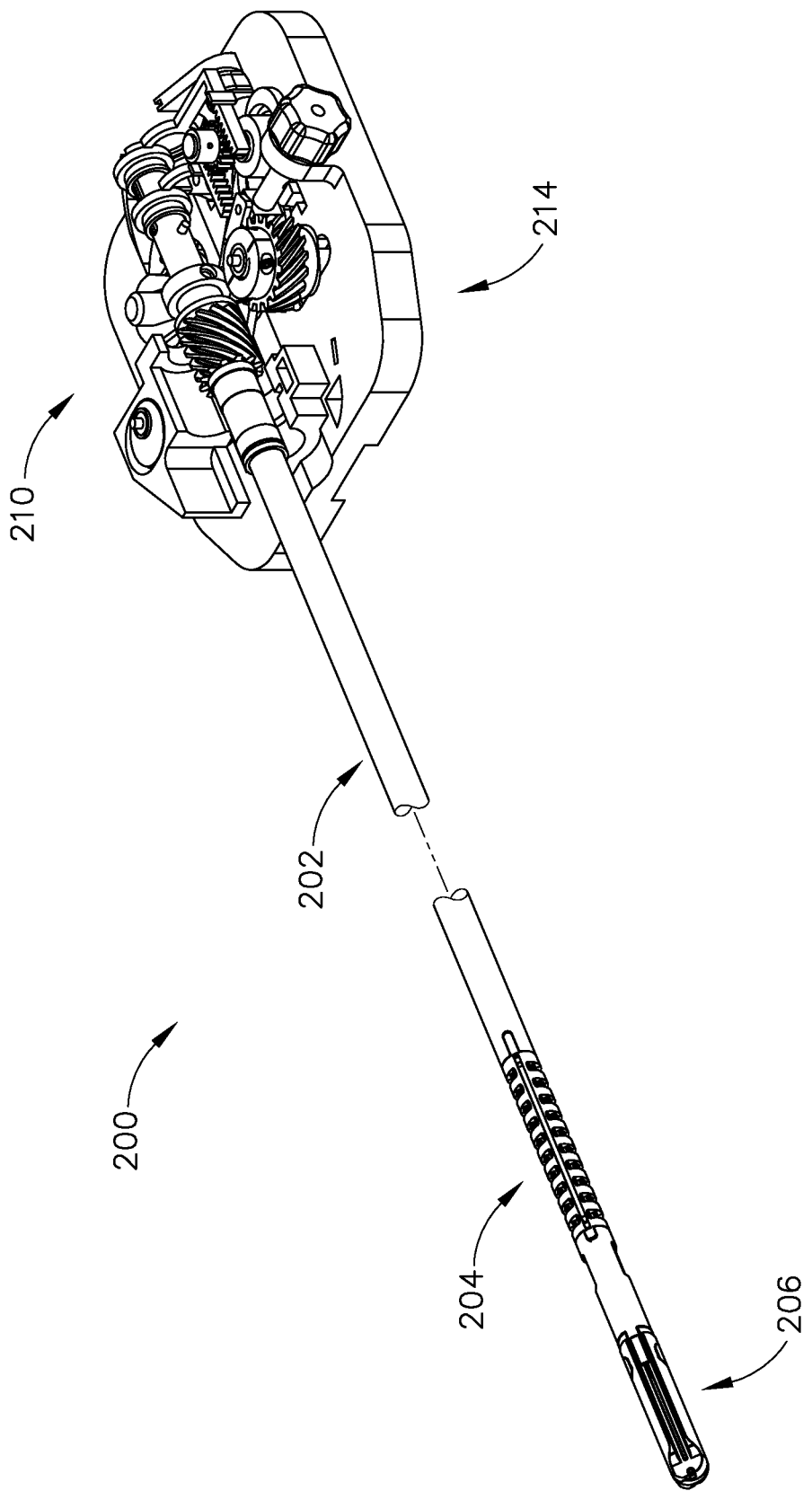
FIG. 14 depicts a partial perspective view of another exemplary surgical instrument suitable for incorporation with the system of FIG. 1.
Figure 15:
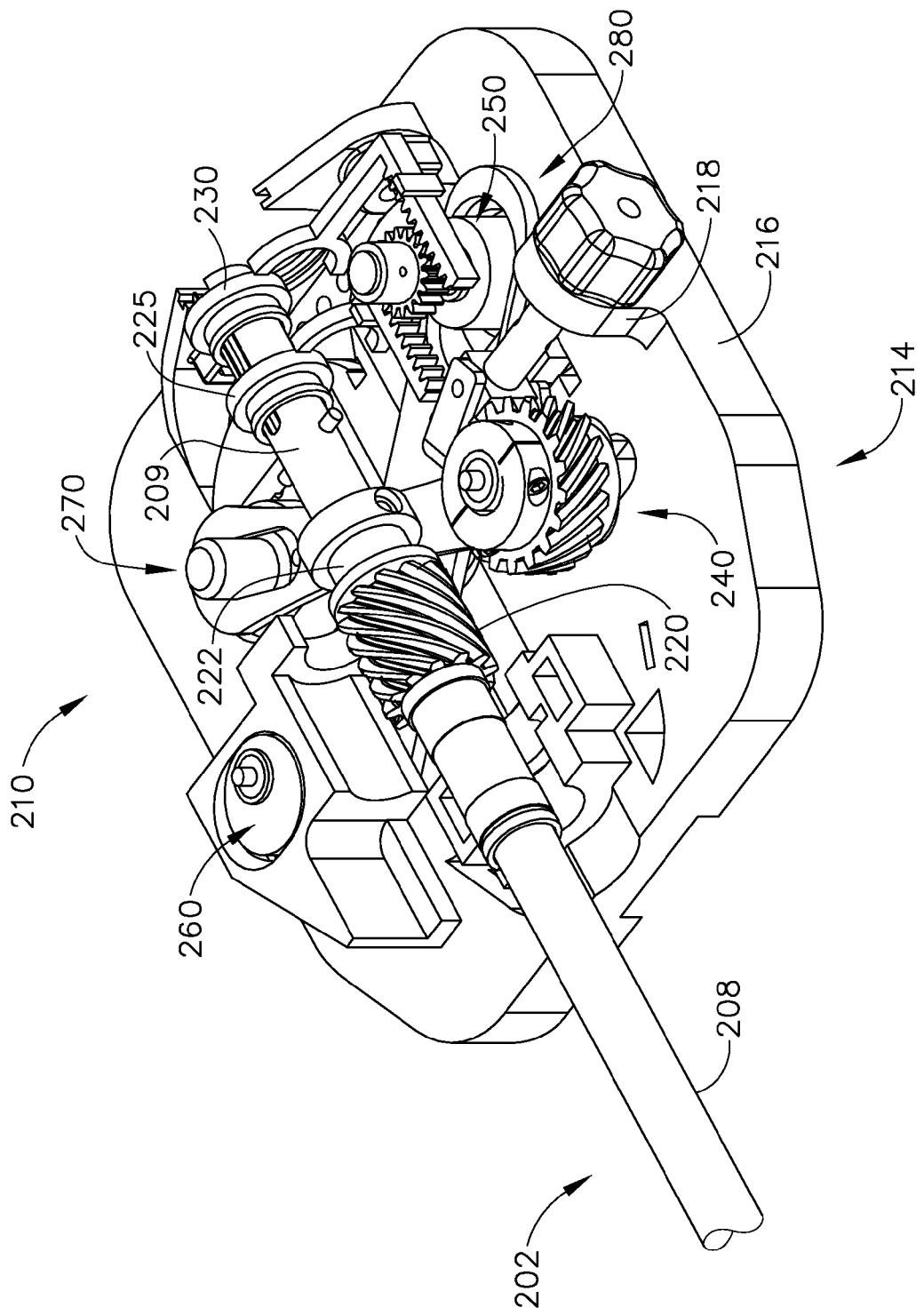
FIG. 15 depicts a partial perspective view of an interface assembly and a proximal portion of the shaft assembly of the instrument of FIG. 14.

III. Exemplary Alternative Electrosurgical Instrument with Translating Drive Assemblies FIGS. 14-15 show an exemplary alternative electrosurgical instrument (200). Instrument (200) of this example is substantially similar to instrument (100) described above in that instrument (200) has a shaft assembly (202), an articulation section (204), and an end effector (206) that are substantially identical to shaft assembly (160), articulation section (170), and end effector (180) described above. Instrument (200) of this example is also operable to couple with a dock (72) of robotic arm cart (40) via an interface assembly (210). However, interface assembly (210) of this example is different from interface assembly (110) described above. In some instances, it may be economically desirable to provide a shaft assembly (202) that is removable from interface assembly (210). For example, shaft assembly (202) may be removed from interface assembly (210) after a surgical procedure such that shaft assembly (202) may be disposed of, while interface assembly (210) may be sterilized and reused in another surgical procedure. Accordingly, shaft assembly (202) and interface assembly (210) include features to allow drive assemblies (240, 250, 260, 270) of interface assembly (210) to translate relative to shaft assembly (202) to removably engage shaft assembly (202) and allow shaft assembly (202) to be inserted and/or removed from interface assembly (210). The examples below include several merely illustrative versions of translating features that may be readily introduced to an instrument (200).

A. Exemplary Translating Drive Assemblies with a Side Rotation Knob

Figure 16:
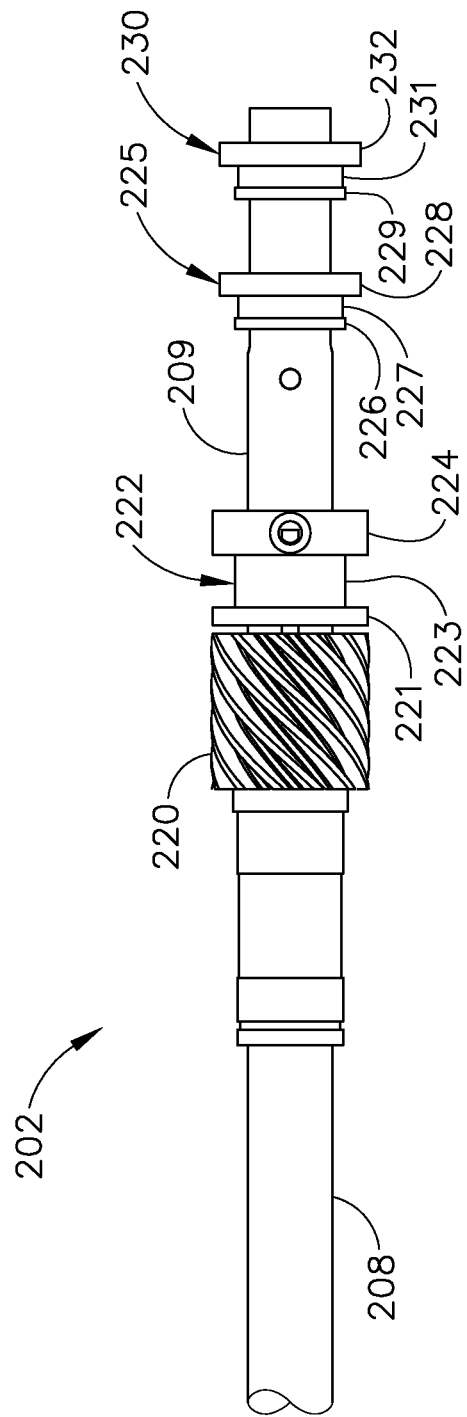
FIG. 16 depicts an elevational side view of a proximal end of the shaft assembly of FIG. 15.

FIG. 16 shows shaft assembly (202) in greater detail. Shaft assembly (202) comprises an outer shaft (208), inner shaft (209), a helical gear (220), and collars (222, 225, 230). Helical gear (220) is positioned around a proximal portion of outer shaft (208) and is operable to rotate outer shaft (208) relative to interface assembly (210). The distal portion of outer shaft (208) is coupled with articulation section (204) and end effector (206) such that rotation of outer shaft (204) by helical gear (220) thereby rotates articulation section (204) and end effector (206). Inner shaft (209) extends proximally from outer shaft (204) and is slidably and coaxially received within outer shaft (204). Collars (222, 225, 230) are positioned around inner shaft (209). First collar (222) is proximal to helical gear (220) and comprises a distal flange (221), a central portion (223), and a proximal flange (224). Central portion (223) connects distal flange (221) and proximal flange (224) and has a smaller outer diameter than distal flange (221) and proximal flange (224). First collar (222) is fixedly coupled with a proximal portion of inner shaft (209). A distal portion of inner shaft (209) is coupled with firing beam (190). Accordingly, translation of first collar (222) thereby translates inner shaft (209) and firing beam (190) relative to outer shaft (208).

Second collar (225) is proximal to first collar (222) and comprises a distal flange (226), a central portion (227), and a proximal flange (228). Central portion (227) connects distal flange (226) and proximal flange (228) and has a smaller outer diameter than distal flange (226) and proximal flange (228). Third collar (230) is proximal to second collar (225) and comprises a distal flange (229), a central portion (231), and a proximal flange (232). Central portion (231) connects distal flange (229) and proximal flange (232) and has a smaller outer diameter than distal flange (229) and proximal flange (232). Second and third collars (225, 230) are translatable relative to inner shaft (209). Second and third collars (225, 230) are each coupled with a respective articulation beam (174, 176) extending within inner shaft (209) such that translation of second and third collars (225, 230) thereby translates articulation beams (174, 176). Thus, translation of collars (225, 230) provides articulation at articulation section (204).

Figure 17:
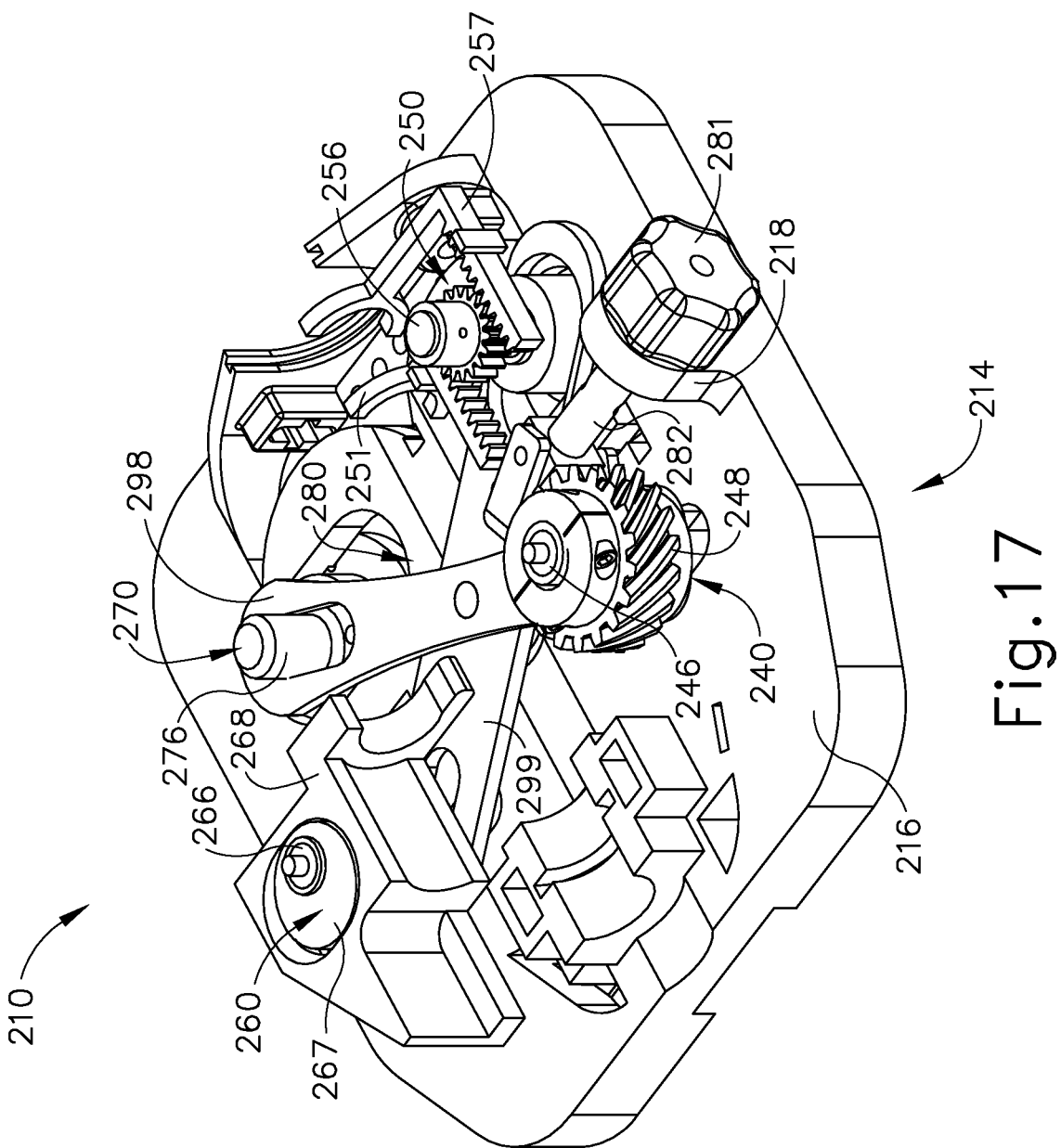
FIG. 17 depicts a perspective view of the interface assembly of FIG. 15.
Figure 18:
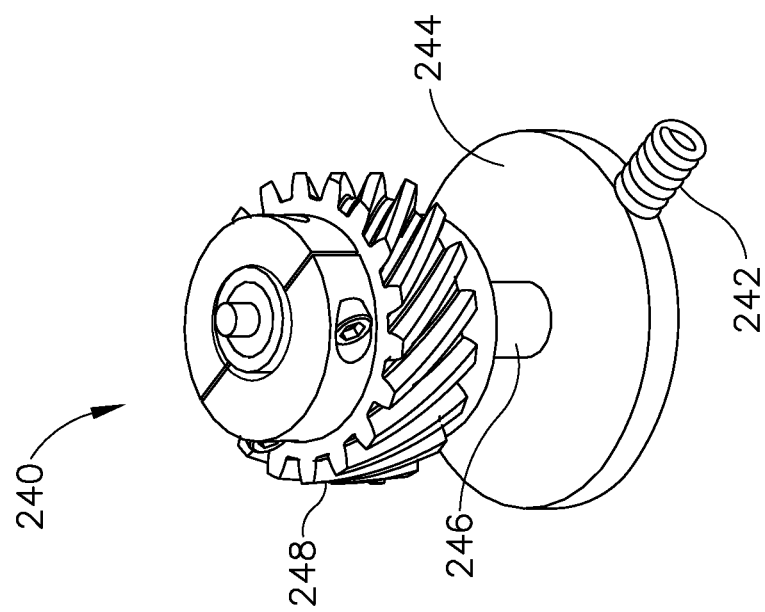
FIG. 18 depicts a perspective view of a first drive assembly of the interface assembly of FIG. 15.

FIG. 17 shows a base (214) of interface assembly (210) that is removably couplable with shaft assembly (202). Base (214) of interface assembly (210) comprises drive assemblies (240, 250, 260, 270) and translation assembly (280) positioned on mounting plate (216). First drive assembly (240) comprises a helical gear (248), drive shaft (246), and disc (244), as shown in FIG. 18. Helical gear (248) is mounted on drive shaft (246), which is mounted on disc (244). Drive shaft (246) extends through an opening of mounting plate (216) such that disc (244) is positioned below mounting plate (216) and helical gear (248) is positioned above mounting plate (216). Helical gear (248) is configured to engage helical gear (220) of shaft assembly (202). Disc (244) is coupled with drive features in dock (72) to rotate disc (244). Rotation of disc (244) thereby rotates outer shaft (208) of shaft assembly (202) through the rotation of drive shaft (246), helical gear (248), and helical gear (220). A resilient member (242) is coupled with disc (244) to resiliently bias disc (244) within mounting plate (216) laterally toward shaft assembly (202).

Figure 19:
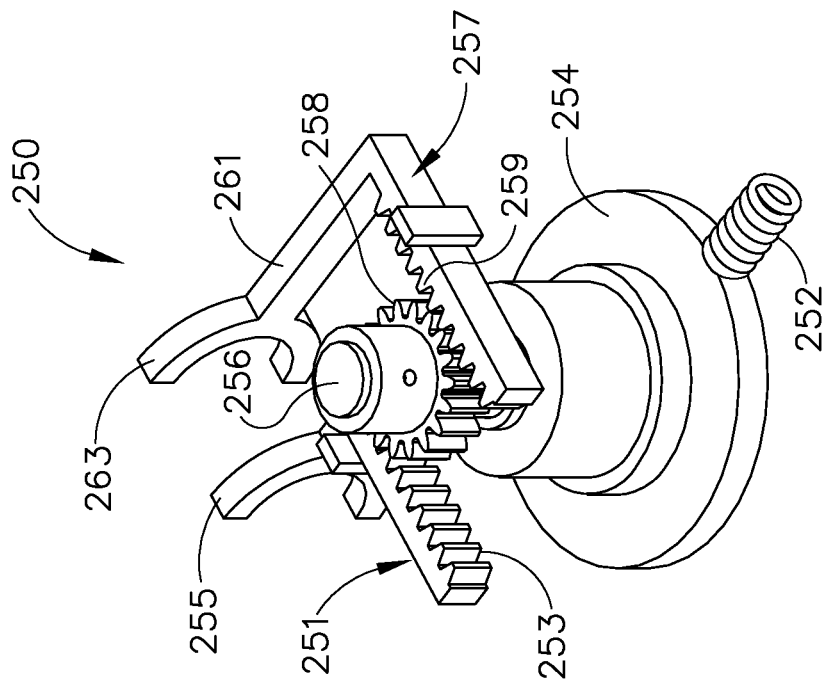
FIG. 19 depicts a perspective view of a second drive assembly of the interface assembly of FIG. 15.

Second drive assembly (250) comprises a pair of racks (251, 257), pinion gear (258), drive shaft (256), and disc (254), as shown in FIG. 19. First rack (251) comprises a first longitudinal row of teeth (253), a first arm (255) extending transversely from teeth (253), and a first engagement feature (255) coupled to first arm (255). First engagement feature (255) is curved and is sized to correspond to central portion (227) of second collar (225) of shaft assembly (202) such that first engagement feature (255) is configured to engage and wrap around a portion of central portion (227). When first engagement feature (255) is engaged with central portion (227), distal flange (226) and proximal flange (228) of second collar (225) extend past first engagement feature (255) to maintain the longitudinal position of first engagement feature (255) relative to second collar (255). First engagement feature (255) is coupled with second collar (225) such that second collar (225) is rotatable relative to first engagement feature (255). Second rack (257) comprises a second longitudinal row of teeth (259), a second arm (261) extending transversely from teeth (259), and a second engagement feature (263) coupled to second arm (261). Second arm (261) extends to longitudinally align first engagement feature (255) and second engagement feature (263). Second engagement feature (263) is curved and is sized to correspond to central portion (231) of third collar (230) of shaft assembly (202) such that second engagement feature (263) is configured to engage and wrap around a portion of central portion (231). When second engagement feature (263) is engaged with central portion (231), distal flange (229) and proximal flange (232) of third collar (230) extend past second engagement feature (263) to maintain the longitudinal position of second engagement feature (263) relative to third collar (230). Second engagement feature (263) is coupled with third collar (230) such that third collar (230) is rotatable relative to second engagement feature (263). Each row of teeth (253, 259) of racks (251, 257) engages a gear (258) mounted on drive shaft (256). Drive shaft (256) extends upwardly from disc (254), through an opening of mounting plate (216) such that disc (254) is positioned below mounting plate (216) and gear (258) is positioned above mounting plate (216). Disc (254) is coupled with drive features in dock (72) to rotate disc (254). Rotation of disc (254) thereby rotates drive shaft (256) and gear (258). Rotation of gear (258) translates racks (251, 257) simultaneously in opposing directions to thereby translate second and third collars (225, 230) in opposing directions. Accordingly, articulation beams (174, 176) are translated by second and third collars (225, 230) to laterally deflect end effector (206) from shaft assembly (202). A resilient member (252) is coupled with disc (254) to resiliently bias disc (254) within mounting plate (216) laterally toward shaft assembly (202).

Figure 20:
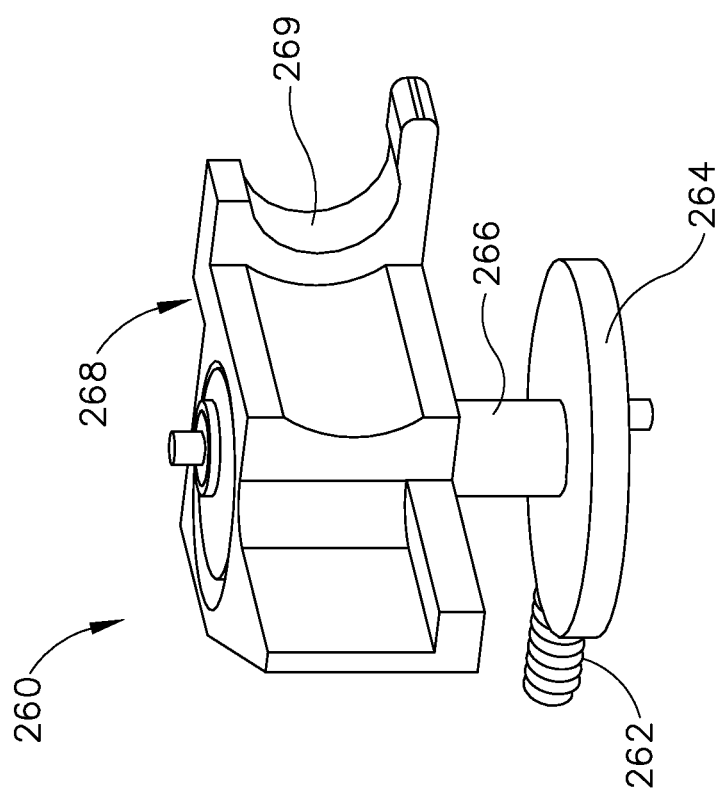
FIG. 20 depicts a perspective view of a third drive assembly of the interface assembly of FIG. 15.

Third drive assembly (260) comprises a eccentric cam (267) mounted on drive shaft (266), which is mounted on disc (264), as shown in FIG. 20. Drive shaft (266) extends through an opening of mounting plate (216) such that disc (264) is positioned below mounting plate (216) and eccentric cam (267) is positioned above mounting plate (216). An elongate opening of arm (268) is positioned around eccentric cam (267). Arm (268) comprises an engagement feature (269) extending laterally from arm (268). Engagement feature (269) has a curved profile and is sized to correspond to central portion (223) of first collar (222) of shaft assembly (202) such that engagement feature (269) is configured to engage and wrap around a portion of central portion (223). When engagement feature (269) is engaged with central portion (223), distal flange (221) and proximal flange (224) of first collar (222) extend past engagement feature (269) to maintain the longitudinal position of engagement feature (269) relative to first collar (222). Engagement feature (269) is coupled with first collar (222) such that first collar (222) is rotatable relative to engagement feature (269). Disc (264) is coupled with drive features in dock (72) to rotate disc (264), which then causes the rotation of drive shaft (266) and eccentric cam (267). The off-center rotation of cam (267) translates arm (268) to thereby translate first collar (222). Accordingly, firing beam (190) is translated by first collar (222). A resilient member (262) is coupled with disc (264) to resiliently bias disc (264) within mounting plate (216) laterally toward shaft assembly (202).

Figure 21:
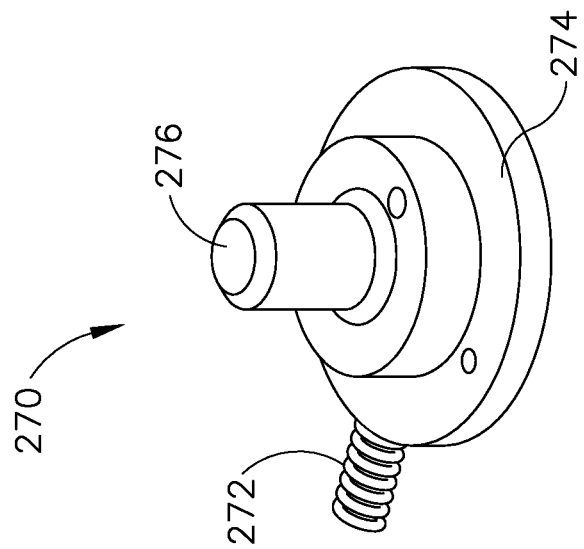
FIG. 21 depicts a perspective view of a fourth drive assembly of the interface assembly of FIG. 15.

Fourth drive assembly (270) comprises a disc (274) and a drive shaft (276) extending upwardly from disc (274), as shown in FIG. 21. Drive shaft (276) is configured to be positioned within an opening of mounting plate (216). In the present example, fourth drive assembly (270) is configured to remain idle and provide pivot support for translation assembly (280). In some instances, disc (274) is coupled with drive features in dock (72) such that fourth drive assembly (270) is configured to translate articulation beams (174, 176), similar to interface assembly (110) described above. A resilient member (272) is coupled with disc (274) to resiliently bias disc (274) within mounting plate (216).

Figure 22:
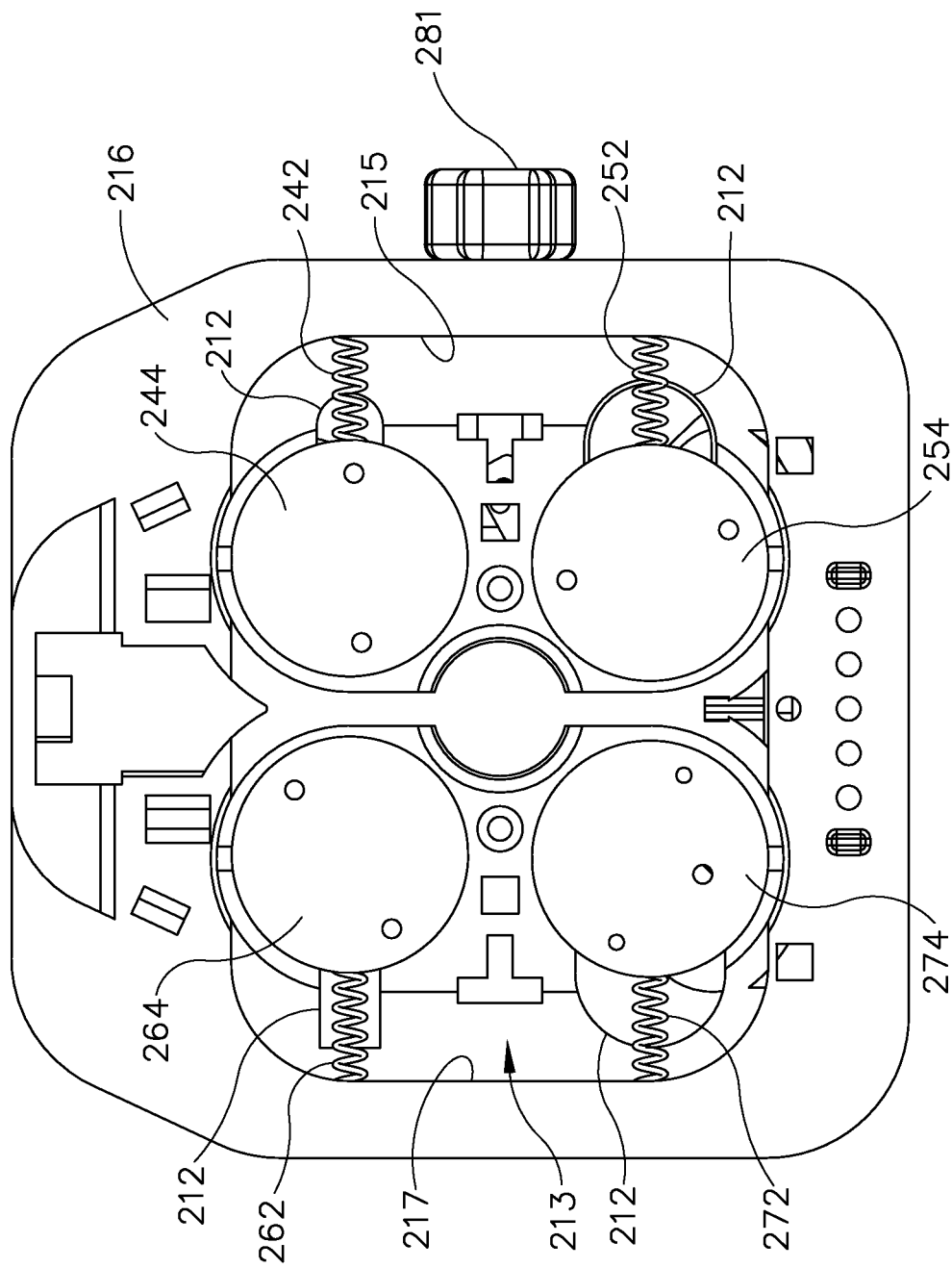
FIG. 22 depicts a bottom plan view of the interface assembly of FIG. 15.

FIG. 22 shows a bottom view of mounting plate (216). The bottom surface of mounting plate (216) comprises a recess (213) extending within mounting plate (216) to house discs (244, 254, 264, 274). Resilient members (242, 252) of drive assemblies (240, 250) are positioned against a first wall (215) of recess (213). Resilient members (262, 272) of drive assemblies (260, 270) are positioned against an opposing wall (217) of recess (213). Resilient members (242, 252, 262, 272) thereby bias discs (244, 254, 264, 274) inwardly within recess (213). Discs (244, 254, 264, 274) are configured to translate inwardly and/or outwardly within recess (213). Mounting plate (216) comprises openings (212) to allow drive shafts (246, 256, 266, 276) to translate within openings (212) as discs (244, 254, 264, 274) are translated.

Figure 23:
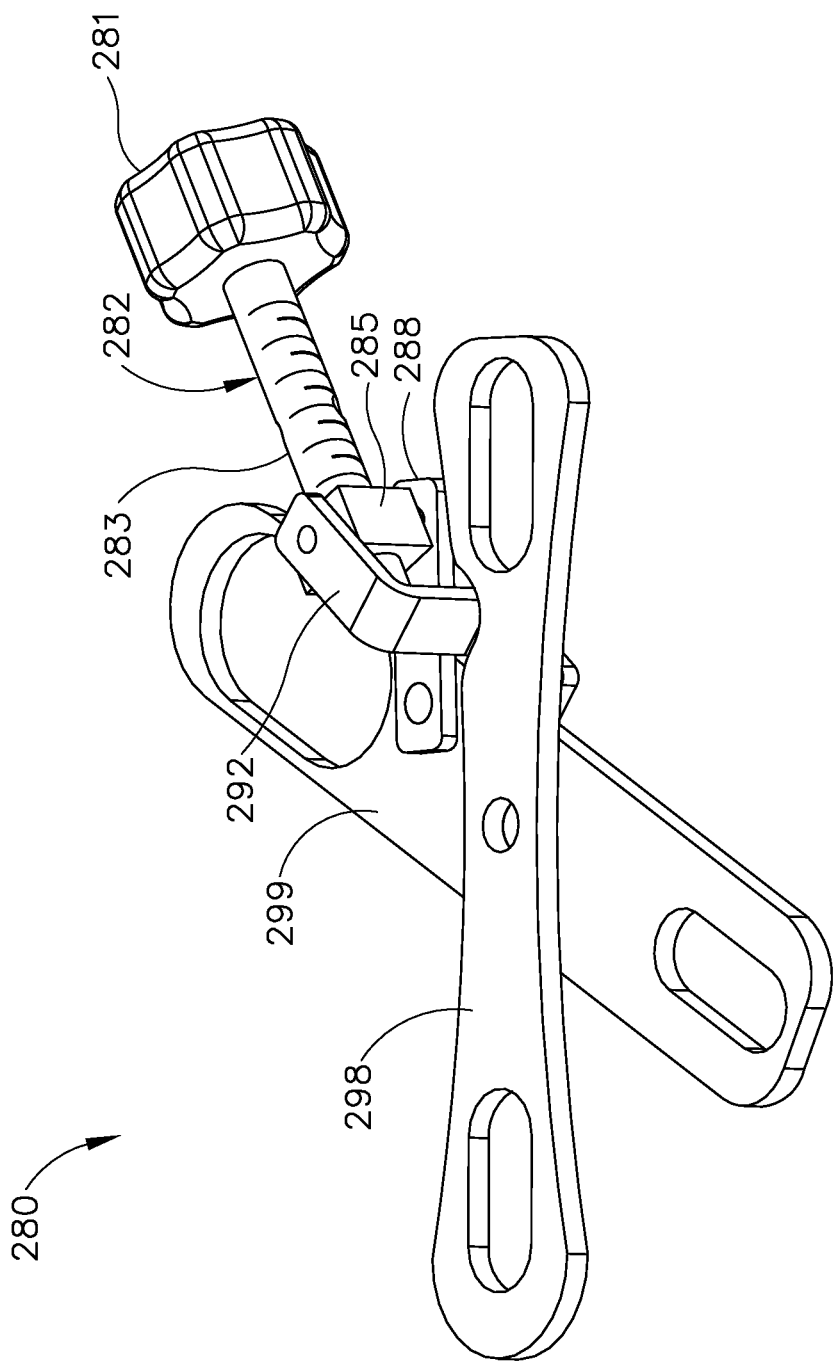
FIG. 23 depicts a perspective view of a linkage assembly of the interface assembly of FIG. 15.
Figure 24:
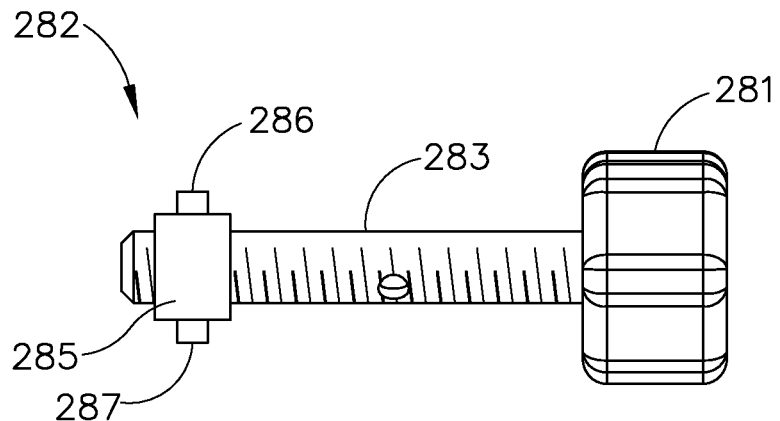
FIG. 24 depicts a side elevational view of a rotation knob assembly of the linkage assembly of FIG. 23.
Figure 25:
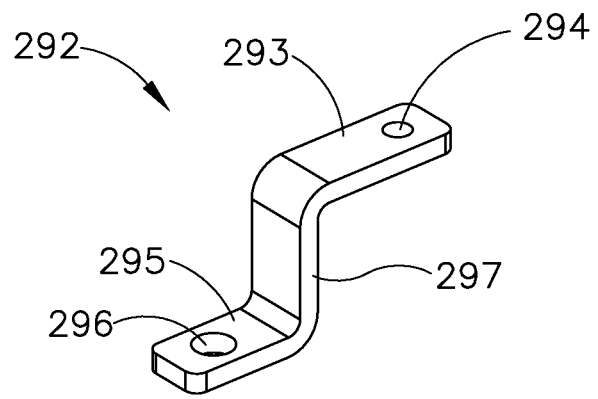
FIG. 25 depicts a perspective view of a first linkage of the linkage assembly of FIG. 23.
Figure 26:
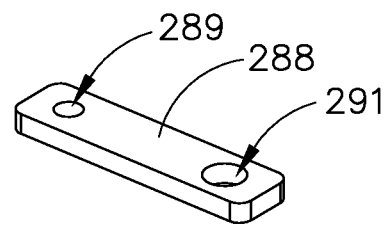
FIG. 26 depicts a perspective view of a second linkage of the linkage assembly of FIG. 23.

FIG. 23 shows translation assembly (280) in more detail. Translation assembly (280) comprises a rotation knob assembly (282), a first link (292), a second link (288), a third link (298), and a fourth link (299). Rotation knob assembly (282) comprises a rotation knob (281) with a threaded screw (283) extending from rotation knob (281), as shown in FIG. 24. A threaded nut (285) is positioned around screw (283) and includes threads corresponding to screw (283) such that rotation of screw (283) by knob (281) translates threaded nut (285). Pins (286, 287) extend outwardly from threaded nut (285) on opposing surfaces. First link (292) comprises a first surface (295), a second surface (297) extending upwardly from first surface (295), and a third surface (293) extending from second surface (297) such that third surface (293) and first surface (295) are substantially parallel, as shown in FIG. 25. Opening (294) is provided on third surface (293) to receive pin (286) of threaded nut (285) such that first link (292) is pivotable relative to threaded nut (285). Another opening (296) is provided on first surface (295). Second link (288) comprises openings (291, 289), as shown in FIG. 26. Opening (291) is configured to receive pin (287) of threaded nut (285) such that second link (288) is pivotable relative to threaded nut (285).

Figure 27:
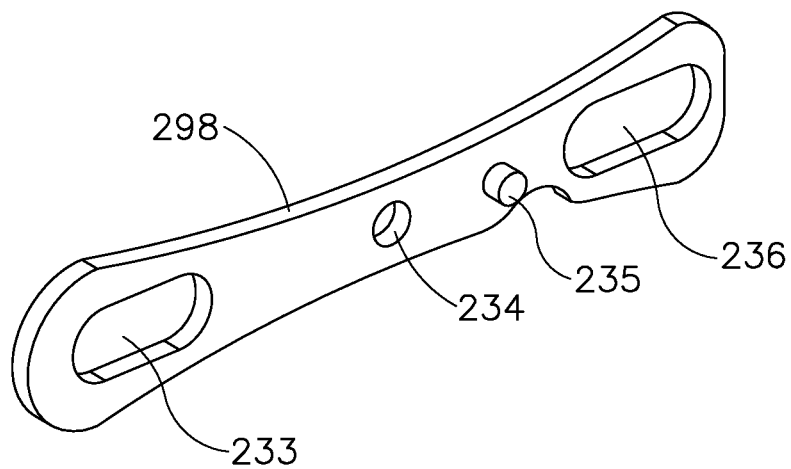
FIG. 27 depicts a perspective view of a third linkage of the linkage assembly of FIG. 23.
Figure 28:
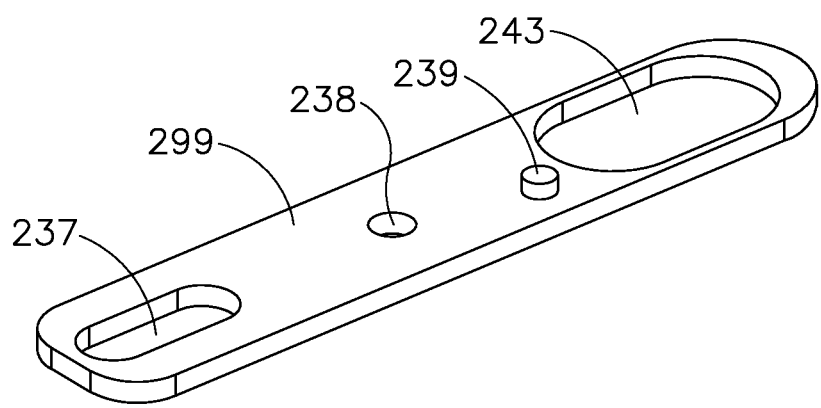
FIG. 28 depicts a perspective view of a fourth linkage of the linkage assembly of FIG. 23.

Third link (298) comprises elongate openings (233, 236) on opposing end portions of third link (298), as shown in FIG. 27. Opening (236) is configured to receive drive shaft (246) of first drive assembly (240) such that drive shaft (246) is translatable within opening (236). Opening (233) is configured to receive drive shaft (276) of fourth drive assembly (270) such that drive shaft (276) is translatable within opening (233). An opening (234) is provided within a central portion of third link (298). A pin (235) extends from third link (298) and is received in opening (296) of first link (292) such that third link (298) is pivotable relative to first link (292). Fourth link (299) comprises elongate openings (237, 243) on opposing end portions of fourth link (299), as shown in FIG. 28. Opening (237) is configured to receive drive shaft (266) of third drive assembly (260) such that drive shaft (266) is translatable within opening (237). Opening (243) is configured to receive drive shaft (256) of second drive assembly (250) such that drive shaft (256) is translatable within opening (243). An opening (238) is provided within a central portion of fourth link (299). Opening (238) of fourth link (299) is positioned adjacent to opening (234) of third link (298). A pin (not shown) may be placed through openings (238, 234) to fix third and fourth links (298, 299) to mounting plate (216) such that fourth link (299) is pivotable relative to third link (298), but the longitudinal and lateral positions of third and fourth links (298, 299) are fixed relative to mounting plate (216). A pin (239) extends from fourth link (299) and is received in opening (289) of second link (288) such that fourth link (299) is pivotable relative to second link (288).

Figure 29A:
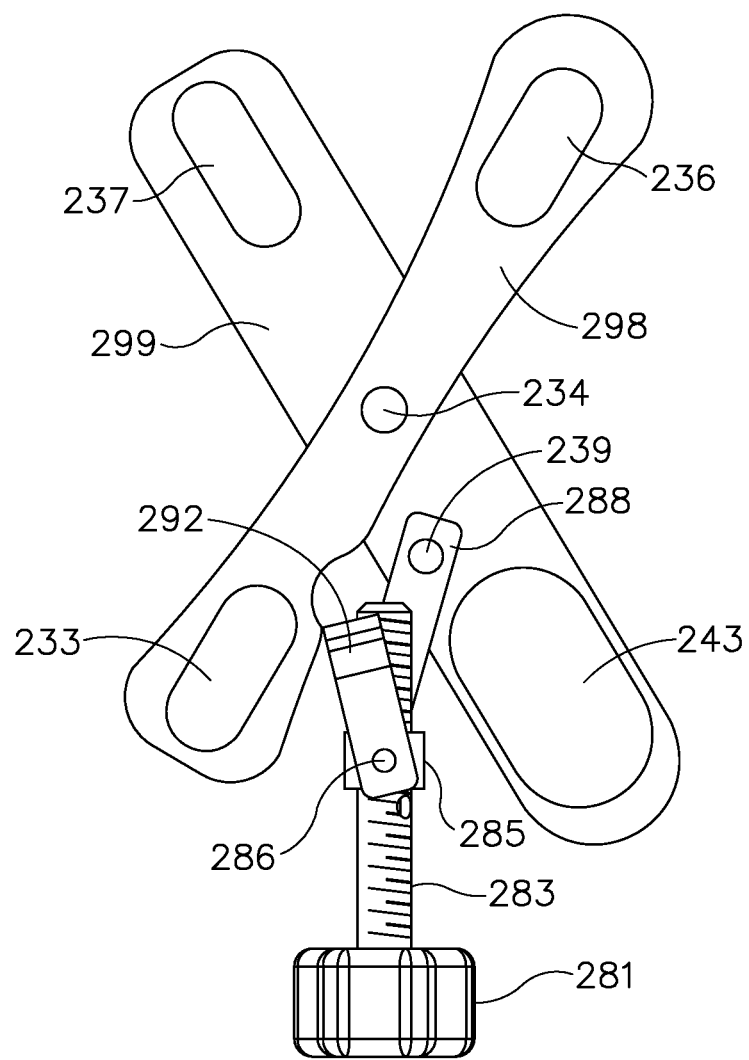
FIG. 29A depicts a top plan view of the linkage assembly of FIG. 23 in a disengaged position.
Figure 29B:
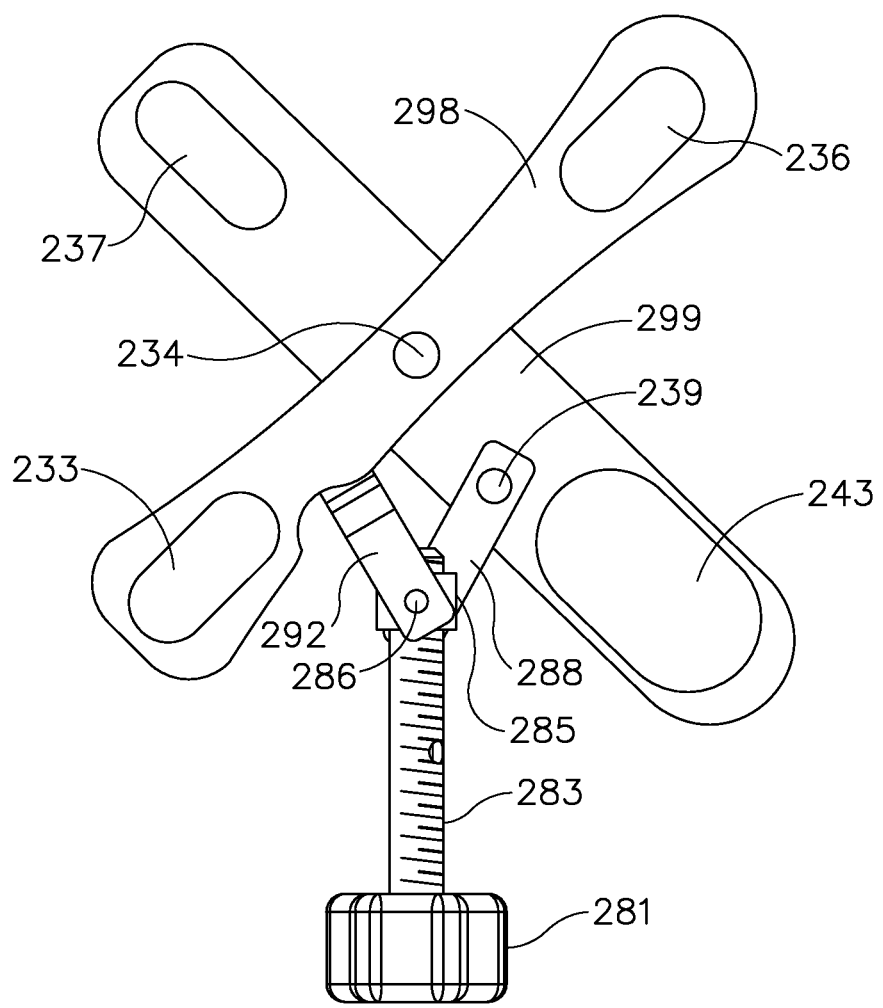
FIG. 29B depicts a top plan view of the linkage assembly of FIG. 23 in an engaged position.
Figure 30A:
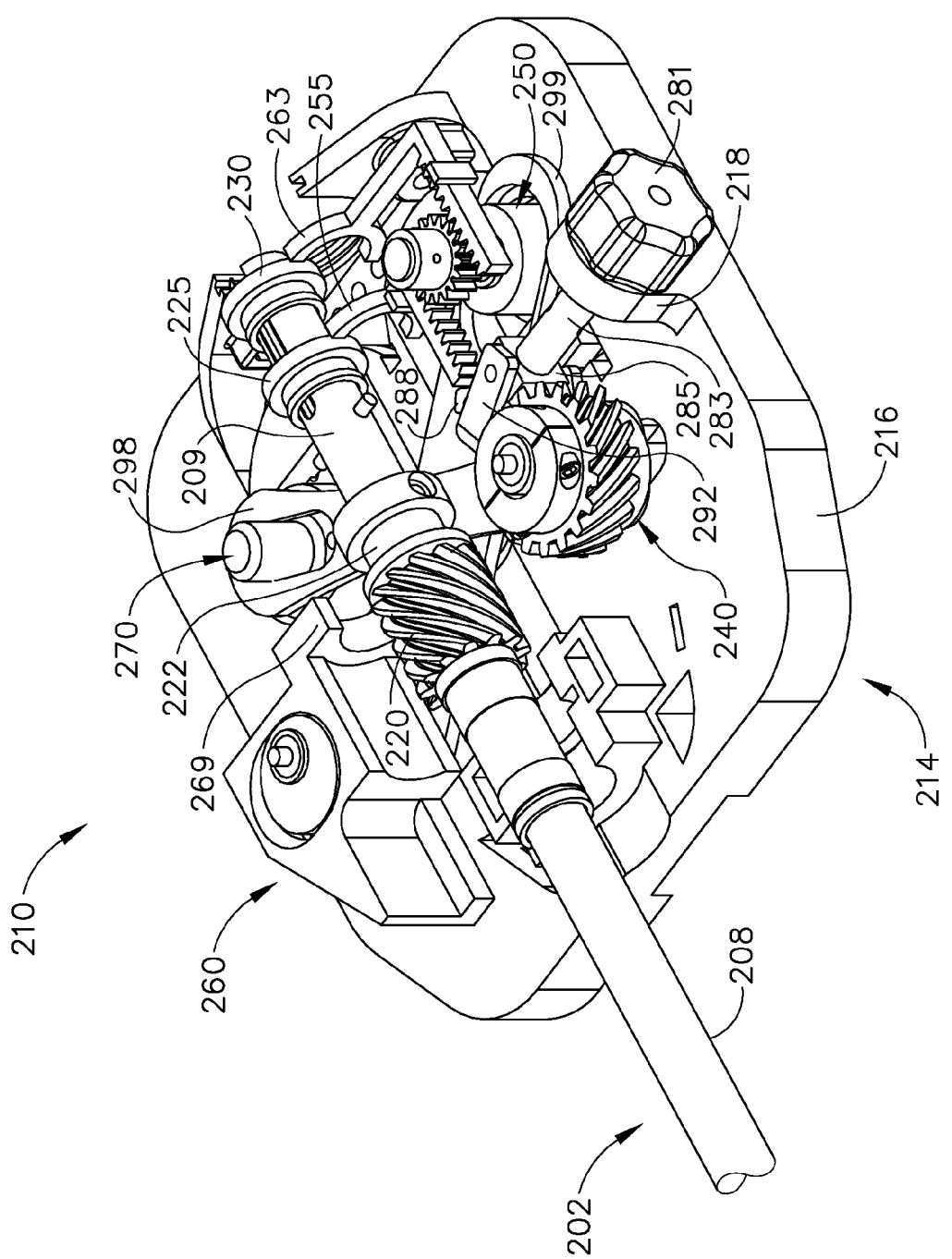
FIG. 30A depicts a partial perspective view of the interface assembly and the shaft assembly of FIG. 15, showing the linkage assembly in the disengaged position.
Figure 30B:
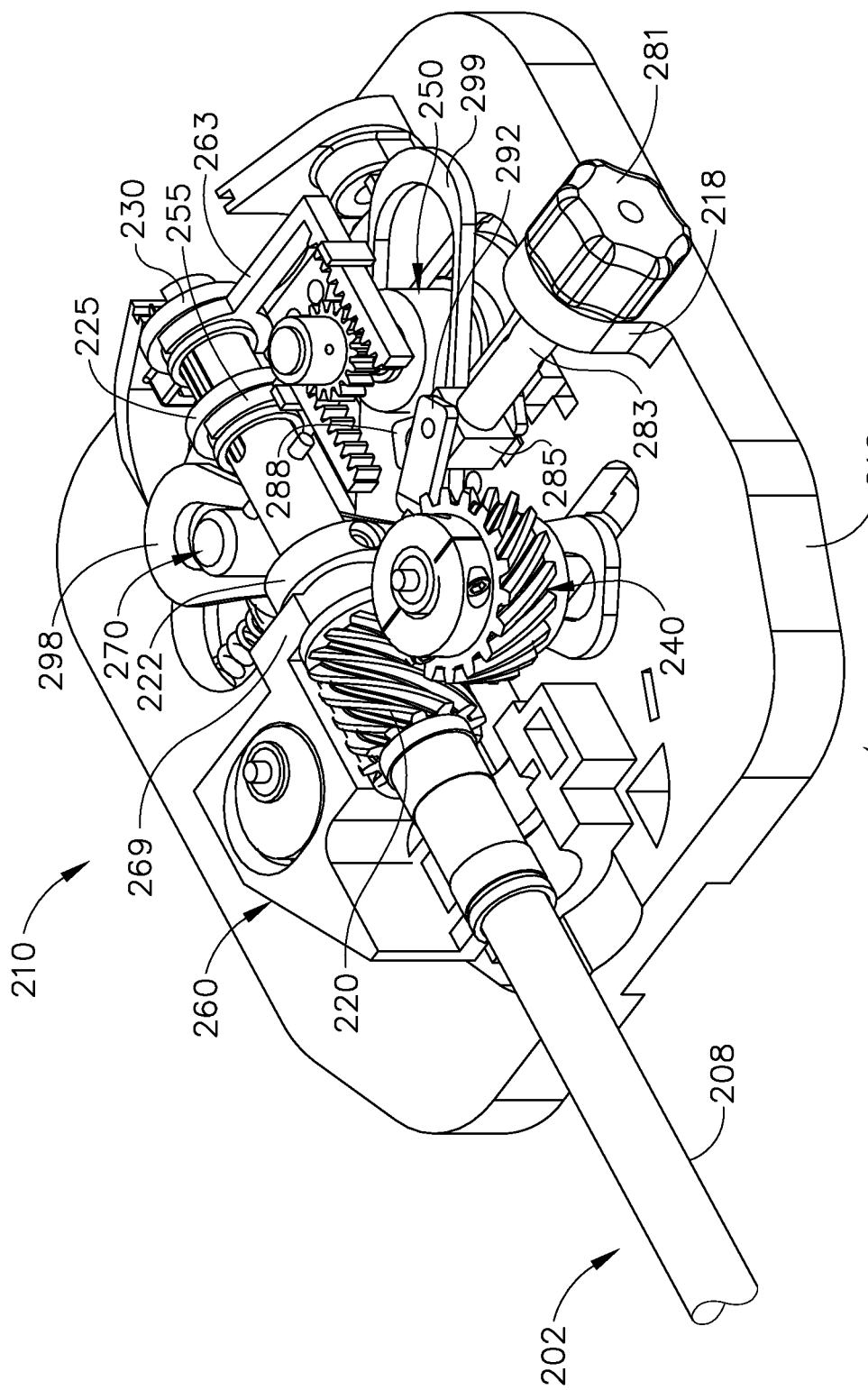
FIG. 30B depicts a partial perspective view of the interface assembly and the shaft assembly of FIG. 15, showing the linkage assembly in the engaged position.

Accordingly, translation assembly (280) is operable to laterally translate drive assemblies (240, 250, 260, 270) within interface assembly (210) to disengage and/or engage shaft assembly (202), as shown in FIGS. 29A-30B. FIG. 29A shows translation assembly (280) in an initial position. In this position, threaded nut (285) is in an inward position on screw (283) and drive assemblies (240, 250, 260, 270) are in an outward position such that drive assemblies (240, 250, 260, 270) are disengaged from shaft assembly (202), as shown in FIG. 30A. Rotation knob (281) is then rotated to translate threaded nut (285) along screw (283) toward an end portion of screw (283), as shown in FIG. 29B. As threaded nut (285) translates toward the end portion of screw (283), first and second links (292, 288) are pivoted away from each other to pivot third and fourth links (298, 299). This causes openings (233, 236, 237, 243) of third and fourth links (298, 299) to translate inwardly within interface assembly (210) to translate drive assemblies (240, 250, 260, 270) inwardly within interface assembly (210) to engage shaft assembly (202), as shown in FIG. 30B. Accordingly, helical gear (248) of first drive assembly (240) engages helical gear (220) of shaft assembly (202), engagement features (255, 263) of second drive assembly (250) engage respective second and third collars (225, 230) of shaft assembly (202), and engagement feature (269) of third drive assembly (260) engages first collar (222) of shaft assembly (202). Resilient members (242, 252, 262, 272) of drive assemblies (240, 250, 260, 270) are biased to help to translate drive assemblies (240, 250, 260, 270) inwardly within interface assembly (210).

To disengage shaft assembly (202), rotation knob (281) may be rotated in the opposite direction to translate links (288, 292, 298, 299) back to the initial position shown in FIGS. 29A and 30A such that drive assemblies (240, 250, 260, 270) translate outwardly within interface assembly (210) to disengage shaft assembly (202). Translation of drive assemblies (240, 250, 260, 270) back to the initial position compresses resilient members (242, 252, 262, 272) within mounting plate (216).

In an exemplary use, translation assembly (280) is positioned in the initial position of FIG. 30A such that drive assemblies (240, 250, 260, 270) are in an outward position within interface assembly (210). Shaft assembly (202) may be inserted distally through a proximal end of interface assembly (210). Shaft assembly (202) may also be positioned above interface assembly (210) with the housing removed and inserted transversely into interface assembly (210). Rotation knob (281) is then rotated to translate threaded nut (285) along screw (283) toward an end portion of screw (283), as shown in FIG. 29B. As threaded nut (285) translates, first and second links (292, 288) are pivoted away from each other to pivot third and fourth links (298, 299). This causes openings (233, 236, 237, 243) of third and fourth links (298, 299) to translate inwardly within interface assembly (210) to translate drive assemblies (240, 250, 260, 270) inwardly within interface assembly (210) to engage shaft assembly (202), as shown in FIG. 30B. Accordingly, helical gear (248) of first drive assembly (240) engages helical gear (220) of shaft assembly (202), engagement features (255, 263) of second drive assembly (250) engage respective second and third collars (225, 230) of shaft assembly (202), and engagement feature (269) of third drive assembly (260) engages first collar (222) of shaft assembly (202). Resilient members (242, 252, 262, 272) of drive assemblies (240, 250, 260, 270) are biased to help to translate drive assemblies (240, 250, 260, 270) inwardly within interface assembly (210).

After drive assemblies (240, 250, 260, 270) engage shaft assembly (202), instrument (200) may be operated. Arm cart (40) is used to insert end effector (206) into a patient via a trocar. Articulation section (204) is substantially straight when end effector (206) and part of shaft assembly (202) are inserted through the trocar. Drive shaft (266) may be rotated to retract firing beam (190) to thereby pivot jaw (182) away from jaw (184). Drive shaft (246) may be rotated through drive features in dock (72) that are coupled with the corresponding disc (244), to position end effector (206) at a desired angular orientation relative to the tissue. Drive shaft (256) may then be rotated through drive features in dock (72) that are coupled with the corresponding discs (254), to pivot or flex articulation section (204) of shaft assembly (202) in order to position end effector (206) at a desired position and orientation relative to an anatomical structure within the patient. Of course end effector (206) may be positioned by drive shaft (246) and/or drive shaft (256) before drive shaft (266) is actuated to open jaws (182, 184). Two layers of tissue of the anatomical structure are then captured between jaws (182, 184) by rotating drive shaft (266) in the opposing direction to advance firing beam (190) distally through a first range of motion. As noted above, flanges (192, 196) cammingly act to pivot jaw (182) toward jaw (184) when firing beam (190) is actuated distally by rotating drive shaft (266).

With tissue layers captured between jaws (182, 184) firing beam (190) continues to advance distally in response to continued rotation of drive shaft (266). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (266) may then be actuated in the opposing direction to retract firing beam (190) and open jaws (182, 184) of end effector (206), thereby releasing the tissue. Articulation section (204) may be again aligned with shaft assembly (202) by actuating drive shaft (256) and jaws (182, 184) may again be closed by actuating drive shaft (266). End effector (206) may then be removed from the patient.

Rotation knob (281) may be rotated in the opposing direction to translate links (288, 292, 298, 299) back to the initial position shown in FIGS. 29A and 30A such that drive assemblies (240, 250, 260, 270) translate outwardly within interface assembly (210) to disengage shaft assembly (202). Shaft assembly (202) is then pulled proximally out of interface assembly (210) or pulled transversely out of interface assembly (210) with the housing removed. Shaft assembly (202) may then be discarded, while interface assembly (210) may be sterilized and reused in another surgical procedure. Of course, various other suitable ways in which instrument (200) may be used will be apparent to those of ordinary skill in the art in view of the teachings herein.

B. Exemplary Translating Drive Assemblies with a Side Pin Assembly

Figure 31:
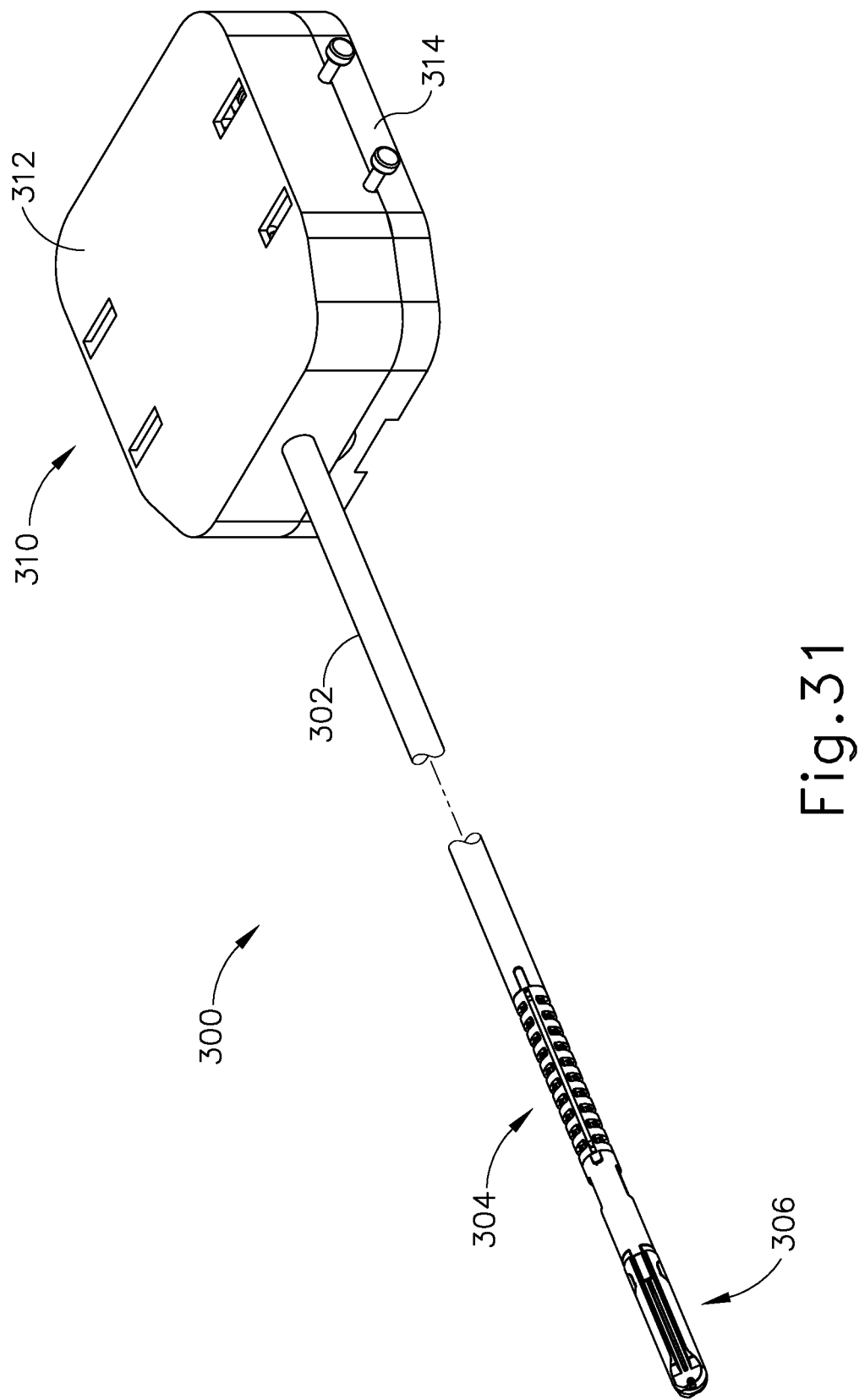
FIG. 31 depicts a perspective view of another exemplary surgical instrument suitable for incorporation with the system of FIG. 1.
Figure 32:
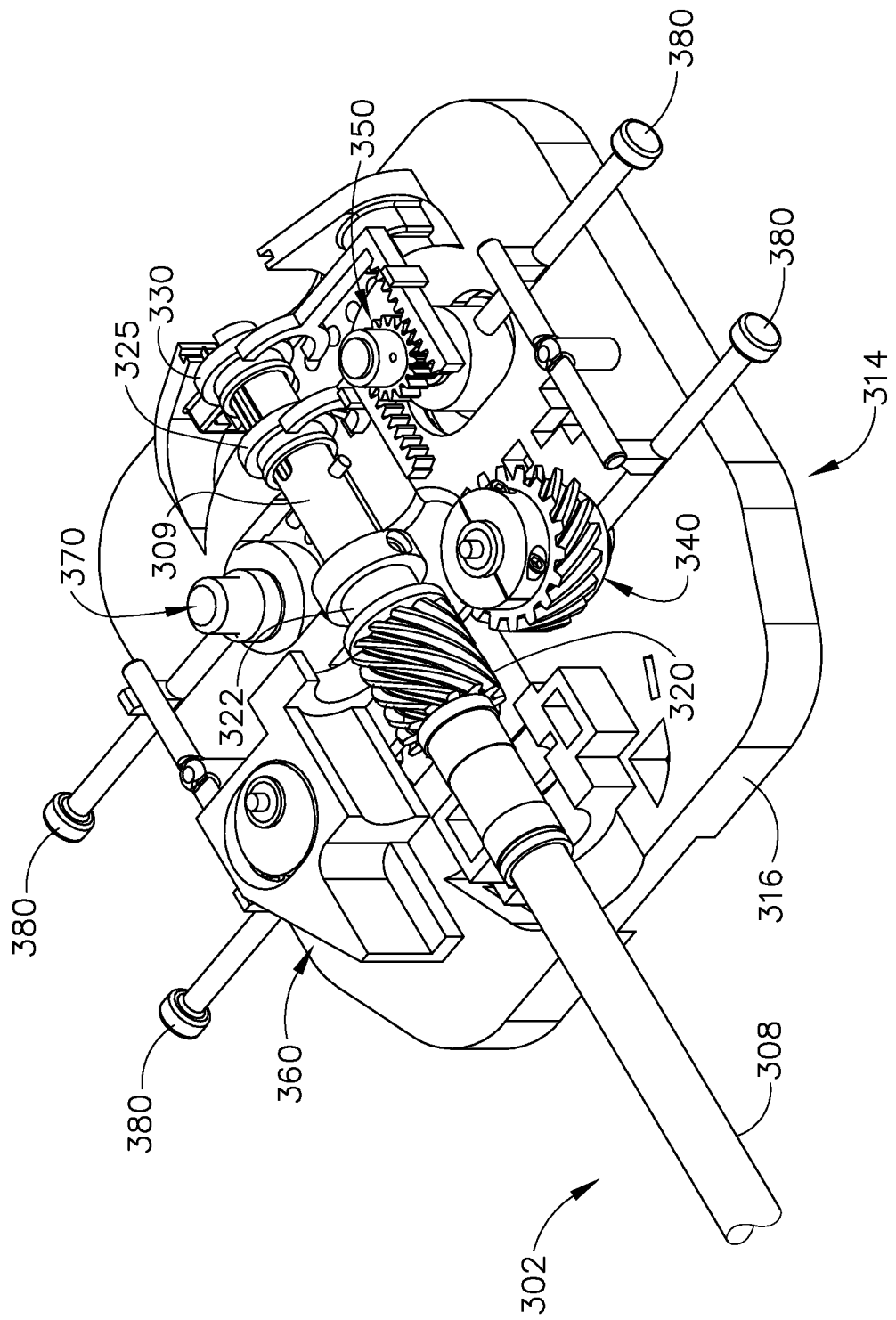
FIG. 32 depicts a partial perspective view of a proximal portion of the shaft assembly and an interface assembly of the instrument of FIG. 31.

FIGS. 31-32 show another exemplary alternative electrosurgical instrument (300) with translating drive assemblies (340, 350, 360, 370). Instrument (300) of this example is substantially similar to instrument (200) described above in that instrument (300) has a shaft assembly (302), an articulation section (304), and an end effector (306) that are substantially identical to shaft assembly (202), articulation section (204), and end effector (206) described above. Shaft assembly (302), first drive assembly (340), second drive assembly (350), third drive assembly (360), and fourth drive assembly (370) are substantially similar to shaft assembly (202), first drive assembly (240), second drive assembly (250), third drive assembly (260), and fourth drive assembly (270). Instrument (300) of this example is also operable to couple with a dock (72) of robotic arm cart (40) via an interface assembly (310). Interface assembly (310) of this example is similar to interface assembly (210), except that interface assembly (310) comprises a plurality of pin assemblies (380) configured to laterally translate drive assemblies (340, 350, 360, 370) instead of a translation assembly (280).

Figure 33:
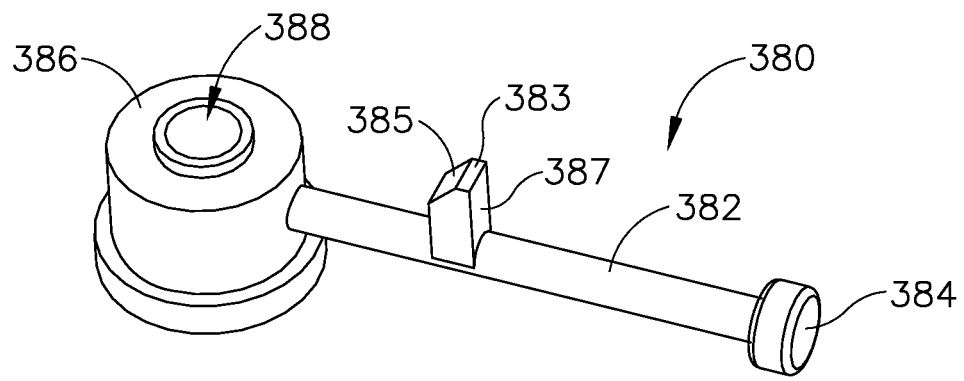
FIG. 33 depicts a perspective view of a pin of the interface assembly of FIG. 32.
Figure 34:
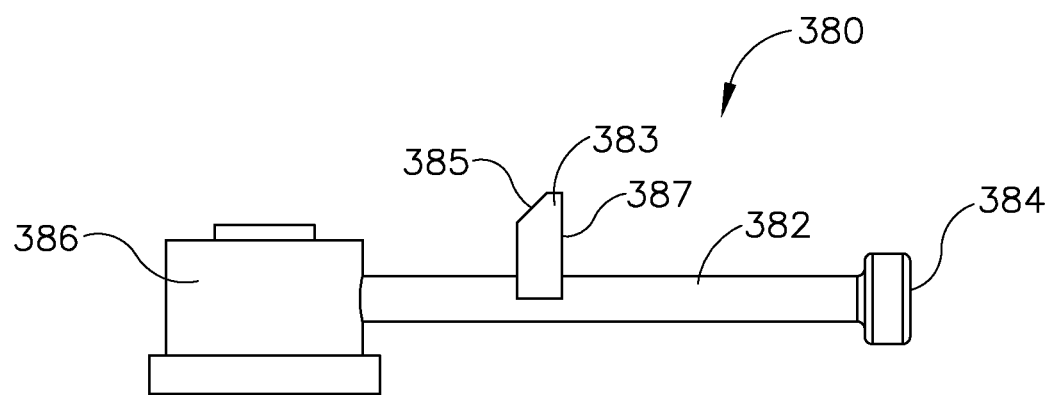
FIG. 34 depicts a side elevational view of the pin of FIG. 33.

Each pin assembly (380) comprises a knob (384), a rod (382) extending from knob (384), and a tubular member (386) positioned on the end of rod (382), as shown in FIGS. 33-34. Tubular member (386) has an opening (388) that extends through tubular member (386). Opening (388) is configured to receive a drive shaft (346, 356, 366, 376) of a drive assembly (340, 350, 360, 370). Accordingly, the present example includes four pin assemblies (380) to couple to each drive assembly (340, 350, 360, 370). However, any other suitable number of pin assemblies (380) may be used. Each knob (384) may be pushed and/or pulled to selectively translate each drive assembly (340, 350, 360, 370) inwardly and/or outwardly within interface assembly (310) to engage and/or disengage shaft assembly (302). In this example, pin assemblies (380) may be translated simultaneously or individually to selectively translate each respective drive assembly (340, 350, 360, 370). Pin assembly (380) further comprises a locking member (383) extending upwardly from rod (382). As best seen in FIG. 34, locking member (383) comprises a ramped surface (385) and a rear wall (387).

Figure 35:
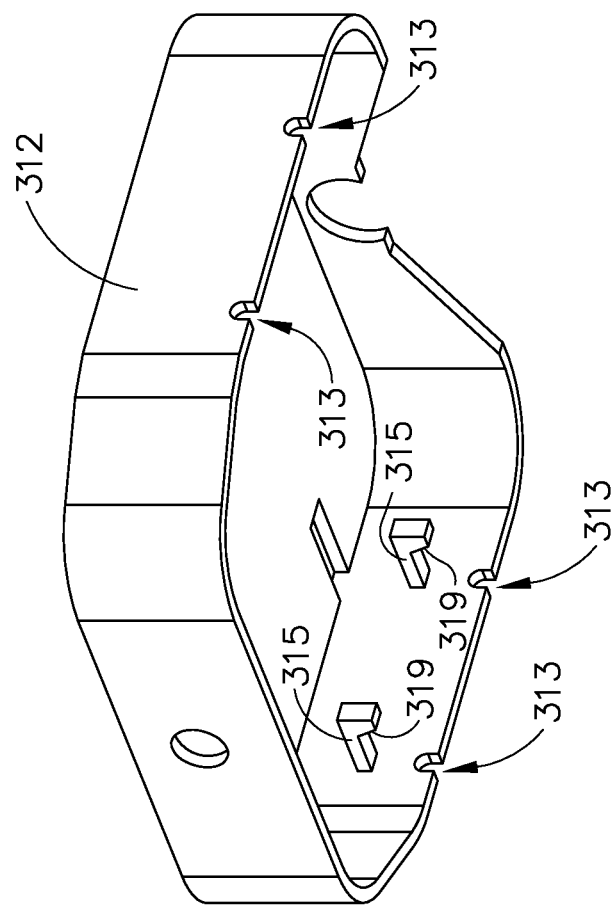
FIG. 35 depicts a bottom perspective view of a cover of the instrument of FIG. 31.
Figure 36A:
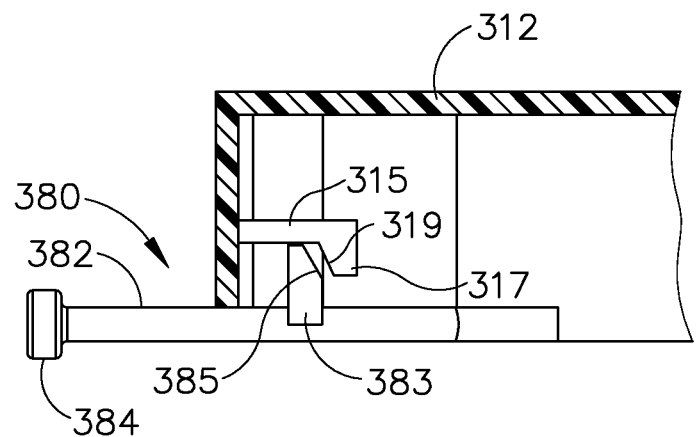
FIG. 36A depicts a partial side view of the pin of FIG. 33 in an initial position within the cover of FIG. 35.
Figure 36B:
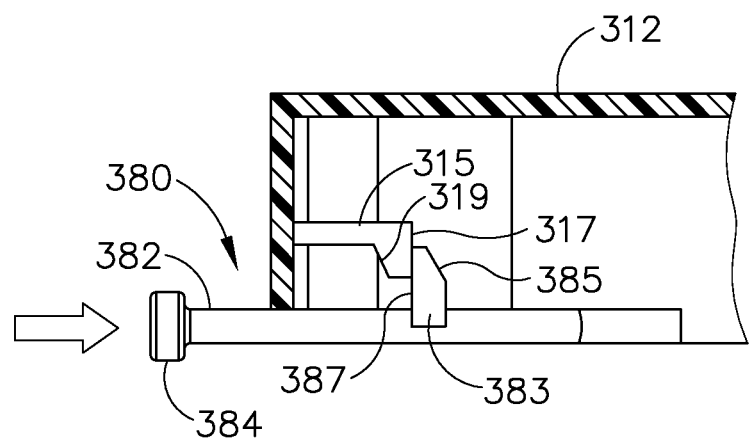
FIG. 36B depicts a partial side view of the pin of FIG. 33 in an engaged position within the cover of FIG. 35.

A housing (312), shown in FIG. 35, is provided to couple with interface assembly (310) and thereby enclose the drive features of instrument (300). Housing (312) comprises recesses (313) and protrusions (315) on opposing side walls to correspond with each pin assembly (380). Recesses (313) are sized to correspond to rods (382) of pin assemblies (380) such that a rod (382) is translatable within a corresponding recess (313). Protrusion (315) extends inwardly and then downwardly from the interior of a side wall of housing (312). Protrusion (315) comprises a ramped surface (319) to correspond to ramped surface (385) of pin assembly (380). As shown in FIG. 36A, locking member (383) of pin assembly (380) is outside of protrusion (315) of housing (312) when pin assembly (380) is in an outward position such that drive assemblies (340, 350, 360, 370) are not engaged with shaft assembly (302). Pin assembly (380) may then be translated inwardly within interface assembly (310) such that the corresponding drive assembly (340, 350, 360, 370) engages shaft assembly (302), as shown in FIG. 36B. When pin assembly (380) translates inwardly, ramped surface (385) of locking member (383) cammingly engages ramped surface (319) of protrusion (315). This causes protrusion (315) to flex upwardly as locking member (383) passes underneath protrusion (315). Once locking member (383) passes protrusion (315), protrusion (315) is resiliently biased to return back to the nominal position in FIG. 36B. Wall (317) of protrusion (315) then engages wall (387) of locking member (383) to maintain pin assembly (380) in the inward position such that the corresponding drive assembly (340, 350, 360, 370) maintains engagement with shaft assembly (302).

Figure 37A:
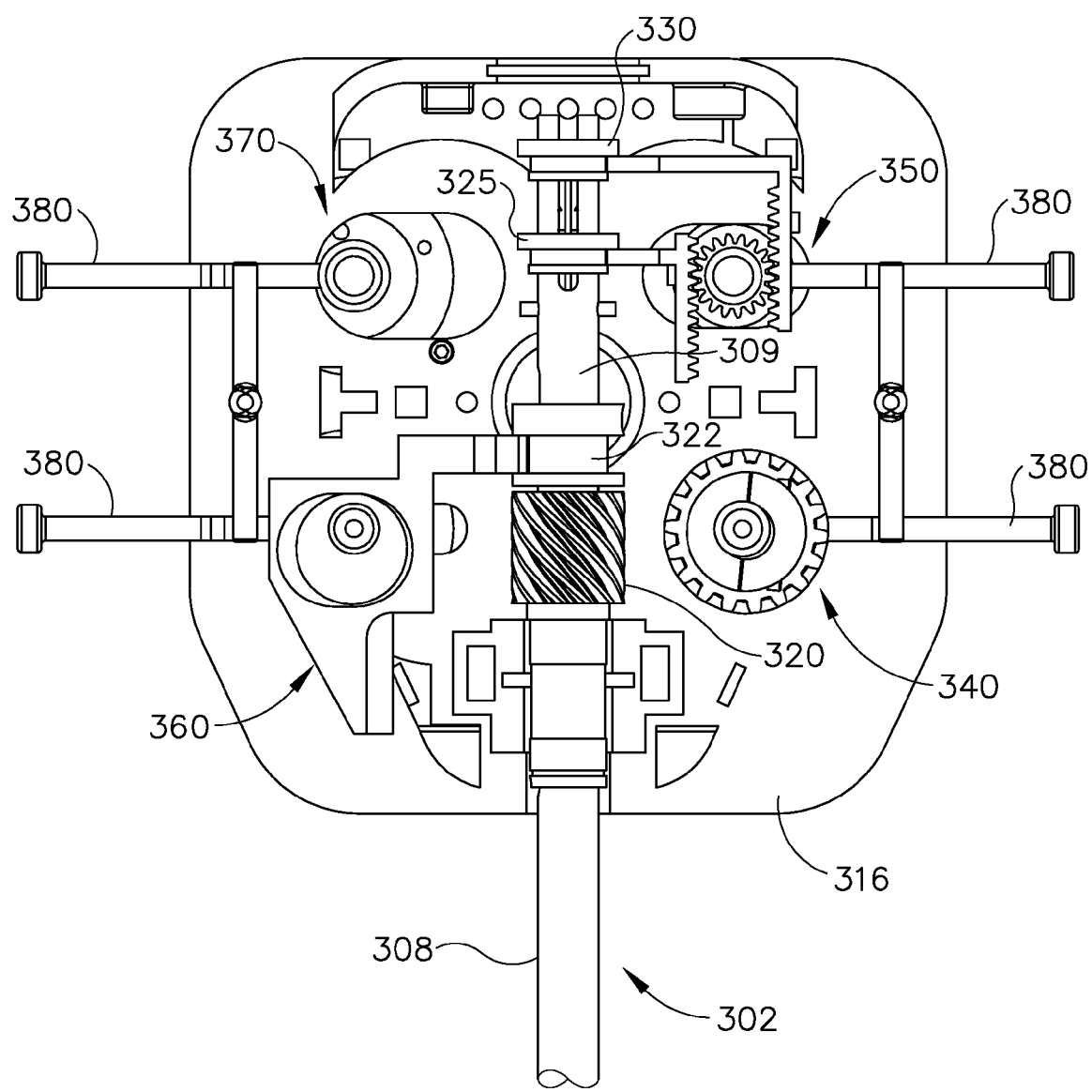
FIG. 37A depicts a top plan view of the interface assembly of FIG. 32 in an initial position.
Figure 37B:
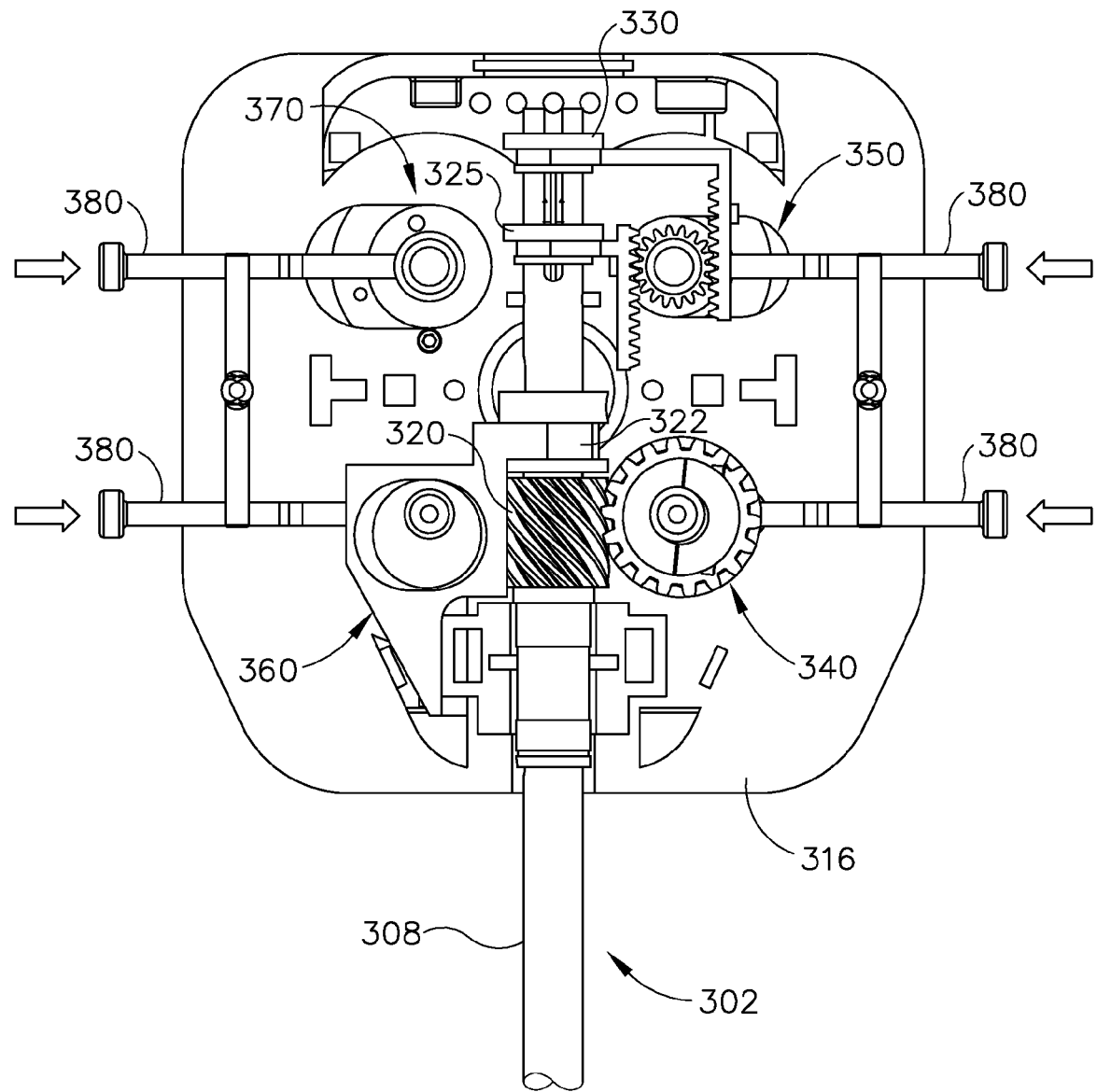
FIG. 37B depicts a top plan view of the interface assembly of FIG. 32 in an engaged position.

In an exemplary use, pin assemblies (380) are positioned in the initial position of FIG. 37A such that drive assemblies (340, 350, 360, 370) are in an outward position within interface assembly (310). Shaft assembly (302) may be inserted distally through a proximal end of interface assembly (310). Alternatively, shaft assembly (302) may be positioned above interface assembly (310) and inserted transversely within interface assembly (310) when housing (312) is removed. A user may selectively push each pin assembly (380) inwardly to translate pin assemblies (380) within interface assembly (310). Accordingly, each corresponding drive assembly (340, 350, 360, 370) engages shaft assembly (302), as shown in FIG. 37B. Locking members (383) of pin assemblies (380) engage protrusions (315) of housing (312) to lock pin assemblies (380) in the inward position. After drive assemblies (340, 350, 360, 370) engage shaft assembly (302), instrument (300) may be operated similar to instrument (200) described above to sever and weld tissue. After the use of instrument (300), housing (312) may be removed from interface assembly (310) such that protrusions (315) of housing (312) disengage locking members (383) of pin assemblies (380). Pin assemblies (380) may then be pulled outwardly to the initial position such that drive assemblies (340, 350, 360, 370) disengage shaft assembly (302), as shown in FIG. 37A. Shaft assembly (302) is then pulled proximally out of interface assembly (310). Alternatively, housing (312) may be removed and shaft assembly (302) may be pulled transversely out of interface assembly (310). Shaft assembly (302) may then be discarded, while interface assembly (310) may be sterilized and reused in another surgical procedure. Of course, various other suitable ways in which instrument (300) may be used will be apparent to those of ordinary skill in the art in view of the teachings herein.

C. Exemplary Translating Drive Assemblies with a Top Pin Assembly

Figure 39:
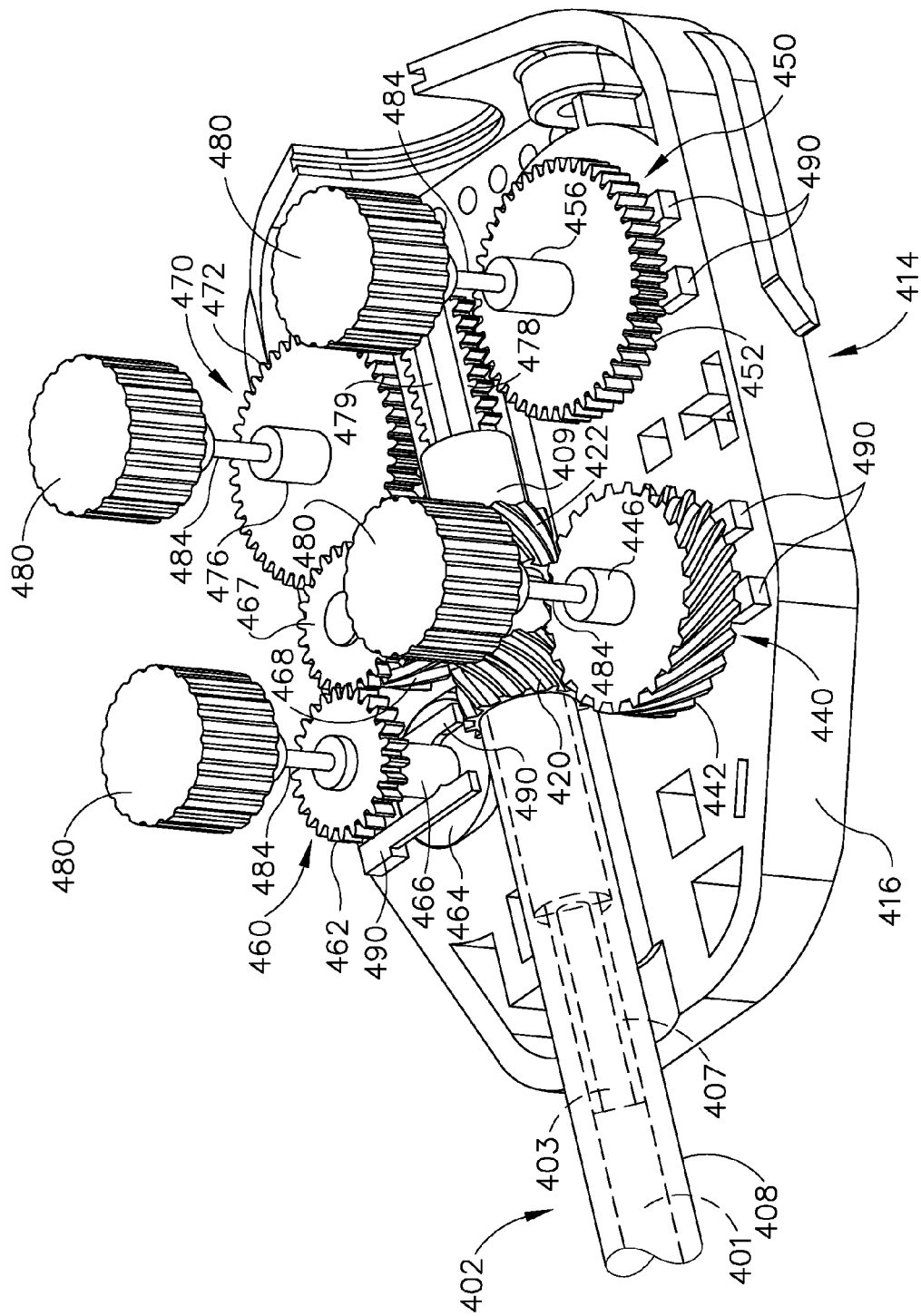
FIG. 39 depicts a partial perspective view of a proximal portion of the shaft assembly and an interface assembly of the instrument of FIG. 38.

FIGS. 38-39 show another exemplary alternative electrosurgical instrument (400) with translating drive assemblies (440, 450, 460, 470). Instrument (400) of this example is substantially similar to instrument (200) described above in that instrument (400) has a shaft assembly (402), an articulation section (404), and an end effector (406) that are substantially identical to shaft assembly (202), articulation section (204), and end effector (206) described above. Instrument (400) of this example is also operable to couple with a dock (72) of robotic arm cart (40) via an interface assembly (410). However, interface assembly (410) of this example is different from interface assembly (210) described above.

Interface assembly (410) comprises drive assemblies (440, 450, 460, 470), as shown in FIG. 39. First drive assembly (440) comprises a helical gear (442) and a drive shaft (446). Helical gear (442) is configured to engage helical gear (420) of on outer shaft (408) of shaft assembly (402). Drive shaft (446) is actuated by a corresponding disc (444) to rotate helical gear (442) of first drive assembly (440) to thereby rotate helical gear (420) of shaft assembly (402) to rotate outer shaft (408), articulation section (404), and end effector (406) together relative to interface assembly (410).

Second drive assembly (460) comprises a disc (464), a drive shaft (466), a first gear (462), a second gear (467), and a helical gear (468). Drive shaft (466) is coupled with disc (464) such that rotation of disc (464) thereby rotates drive shaft (466). First gear (462) is positioned around drive shaft (466) to rotate unitarily with drive shaft (466). First gear (462) engages second gear (467) to thereby rotate second gear (467). Second gear (467) is coupled with helical gear (468) along a common shaft (which is parallel to drive shaft (466)), to unitarily rotate with second gear (467). Helical gear (468) is configured to engage helical gear (422) on inner shaft (409) of shaft assembly (402). Accordingly, drive shaft (466) is actuated by corresponding disc (464) to rotate gears (462, 267, 268) to thereby rotate helical gear (422) of shaft assembly (402). This causes rotation of inner shaft (409). Inner shaft (409) may be coupled to a lead screw (403), which is positioned within a threaded nut (407). Threaded nut (407) is coupled with the proximal end of translation beam (401). Accordingly, inner shaft (409) rotates to rotate lead screw (403), which translates threaded nut (407) and translation beam (401). The distal end of translation beam (401) is coupled with firing beam (190) to thereby translate firing beam (190). Second drive assembly (460) may either rotate freely when first drive assembly (440) is actuated, or second drive assembly (460) may be synchronously driven when first drive assembly (440) is actuated to rotate with first drive assembly (440). This may enable firing beam (190) to rotate together with outer shaft (408), articulation section (404), and end effector (406), without firing beam (190) simultaneously translating relative to these components. Of course, the rotational position of outer shaft (408), articulation section (404), and end effector (406), may be fixed by first drive assembly (440) during intentional translation of firing beam (190).

Third drive assembly (450) comprises a disc (454), a drive shaft (456), and a gear (452). Gear (452) is positioned around drive shaft (456) to rotate unitarily with drive shaft (456) when drive shaft (456) is actuated through disc (456). The teeth of gear (452) are configured to engage an integral rack of articulation beam (478). Fourth drive assembly (470) is similar to third drive assembly (450) and comprises a disc (474), a drive shaft (476), and a gear (472). Gear (472) is positioned around drive shaft (476) to rotate unitarily with drive shaft (476) when drive shaft (476) is actuated through disc (476). The teeth of gear (472) are configured to engage an integral rack of the other articulation beam (479). Accordingly, third and fourth drive assemblies (450, 470) are actuated to rotate drive shafts (456, 476), which drive gears (452, 472) to thereby translate articulation beams (478, 479) in opposing longitudinal directions. A bushing (not shown) may be provided on each articulation beam (478, 479) distal to gears (452, 472) and proximal to outer shaft (408), and may act as mechanical slip rings such that the proximal portions of articulation beams (478, 479) are prevented from rotating when outer shaft (408) rotates. The bushings are configured to communicate the translation of the proximal portions of articulation beams (478, 479) to the distal portions of articulation beams (478, 479) to laterally deflect end effector (406)

relative to shaft assembly (402) at articulation section (404). Outer shaft (408), inner shaft (409), and articulation beams (478, 479) may contain unique identifiers (e.g., in-line resistors, mechanical switches, etc.) that inform surgical system (10) which shaft assembly (402) has been placed within interface assembly (410).

Figure 40:
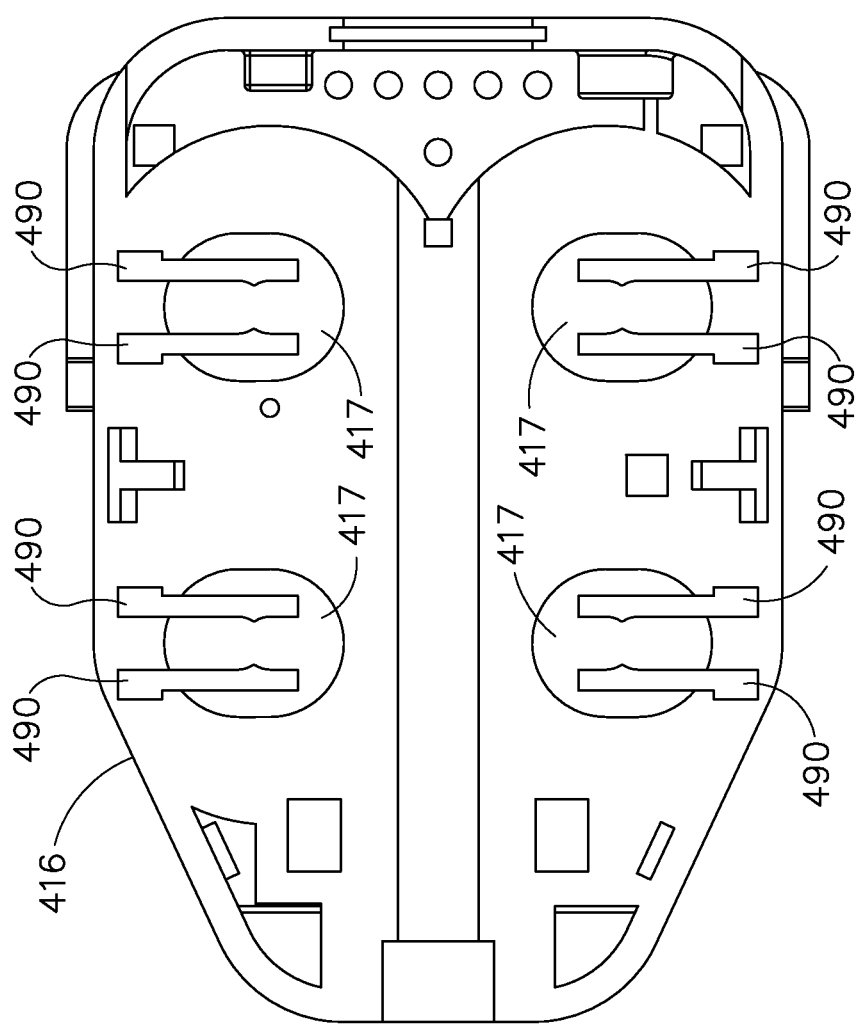
FIG. 40 depicts a top plan view of a base of the interface assembly of FIG. 39.
Figure 41:
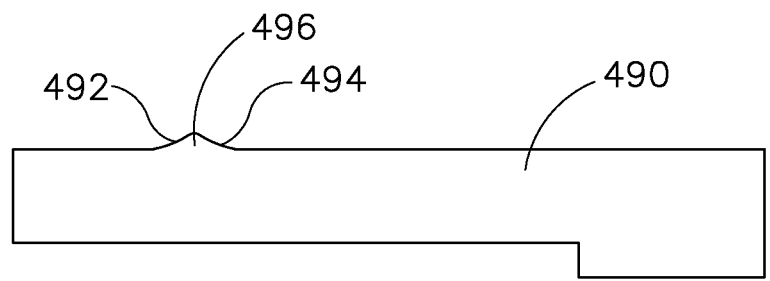
FIG. 41 depicts a top plan view of a locking member of the base of FIG. 40.
Figure 43B:
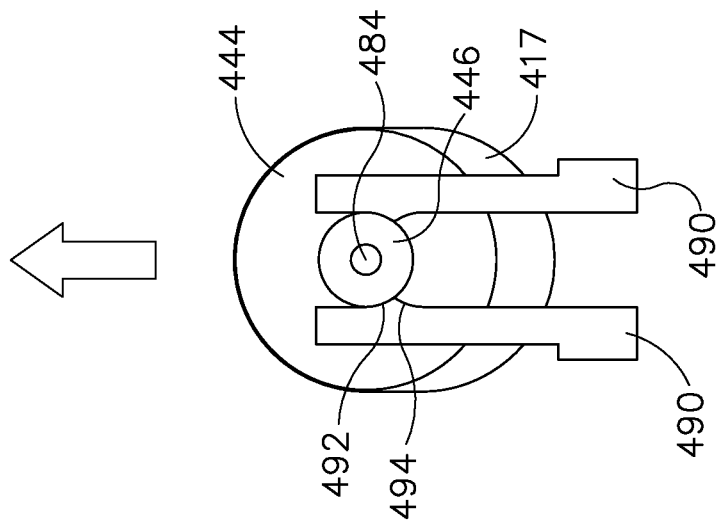
FIG. 43B depicts a partial top plan view of the locking members and knob assembly of the interface assembly of FIG. 39 in an engaged position.
Figure 43A:
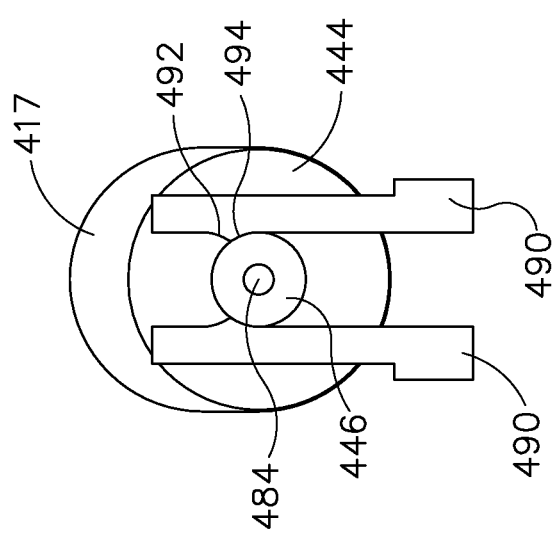
FIG. 43A depicts a partial top plan view of the locking members and knob assembly of the interface assembly of FIG. 39 in an initial position.

Draft shafts (446, 456, 466, 476) of each drive assembly (440, 450, 460, 470) are positioned between a pair of spring clips (490). FIG. 40 shows a pair of spring clips (490) extending inwardly to each opening (417) of mounting plate (416). Spring clips (490) are spaced to correspond to each drive shaft (446, 456, 466, 476) such that the inner wall of each spring clip (490) engages the corresponding drive shaft (446, 456, 466, 476). As shown in FIG. 41, each spring clip (490) comprises a protrusion (496) having a first ramped surface (492) and a second ramped surface (494). Protrusions (496) face inwardly within openings (417) to wrap around a portion of a drive shaft (446, 456, 466, 476) to maintain the lateral positions of drive assemblies (440, 450, 460, 470). For instance, FIGS. 43A and 43B show the translation of first drive assembly (440). In FIG. 43A, first drive assembly (440) is in the outward position such that first drive assembly (440) is disengaged from shaft assembly (402). In this position, the second ramped surface (494) of both spring clips (490) engage drive shaft (446) of drive assembly (440). This maintains the outward position of first drive assembly (440). First drive assembly (440) may then be translated inwardly within opening (417) of mounting plate (416) such that first drive assembly (440) engages shaft assembly (402), as shown in FIG. 43B. As first drive assembly (440) is translated, drive shaft (446) cammingly slides along second ramped surface (494) to drive each spring clip (490) outwardly. When first drive assembly (440) reaches in the inward position, spring clips (490) are resiliently biased to flex back inwardly such that first ramped surface (492) engages drive shaft (446) to maintain drive shaft (446) in the inward position. First drive assembly (440) may then be translated back outwardly to the outward position of FIG. 43A. As first drive assembly (440) translates outward, drive shaft (446) cammingly slides along first ramped surface (492) to drive spring clips (490) outwardly. Spring clips (490) again resiliently flex back inwardly such that second ramped surface (494) engages drive shaft (446).

Figure 42:
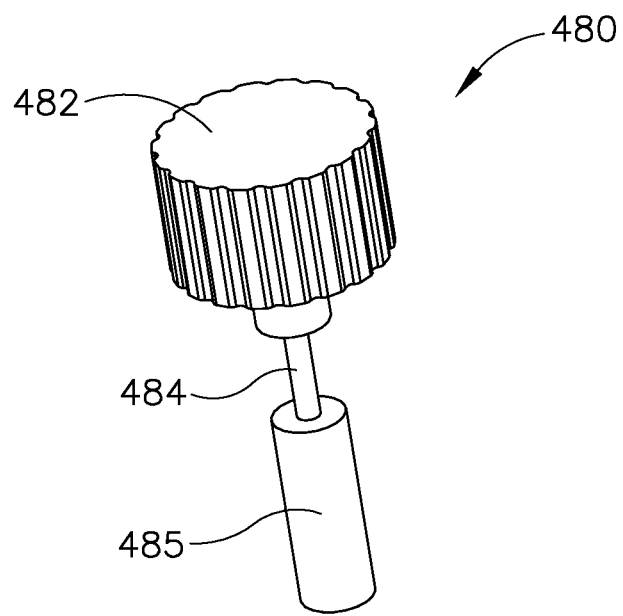
FIG. 42 depicts a perspective view of a knob assembly of the interface assembly of FIG. 39.

In the present example, drive assemblies (440, 450, 460, 470) are translated by pin assemblies (480), shown in FIG. 42. Each pin assembly (480) comprises a knob (482) and a pin (484) extending from knob (482). Each pin (484) is coupled with a corresponding drive shaft (446, 456, 466, 476) of a respective drive assembly (440, 450, 460, 470). Pins (484) extend from a drive shaft (446, 456, 466, 476) through slots within housing (412) such that knobs (482) are positioned above housing (412). Knobs (482) may then be pushed and/or pulled by a user to translate drive assemblies (440, 450, 460, 470) to engage and/or disengage shaft assembly (402). Drive assemblies (440, 450, 460, 470) may be translated simultaneously or independently of each other to selectively engage and/or disengage shaft assembly (402). The slots within cover (412) are configured to allow the translation of pins (484). For example, drive assemblies (440, 450, 460, 470) are in the outward position in FIG. 44A such that drive assemblies (440, 450, 460, 470) are disengaged from shaft assembly (402). Knobs (482) may be pushed inwardly to translate drive assemblies (440, 450, 460, 470) inwardly to engage shaft assembly (402), as shown in FIG. 44B. Knobs (482) may then be pulled outwardly to return drive assemblies (440, 450, 460, 470) to the outward position of FIG. 44A to disengage shaft assembly (402).

Figure 44A:
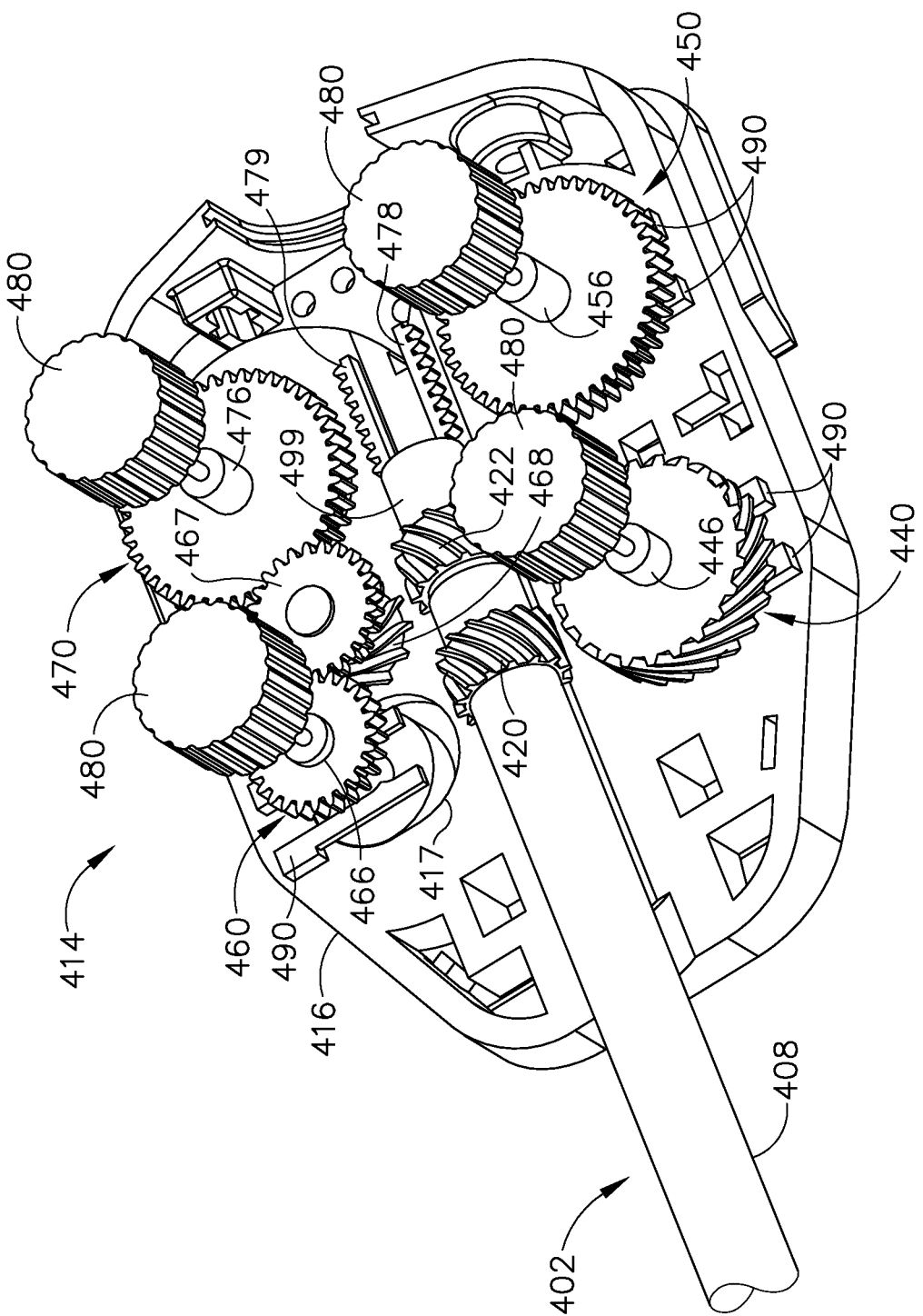
FIG. 44A depicts a partial perspective view of the interface assembly of FIG. 39 in an initial position.
Figure 44B:
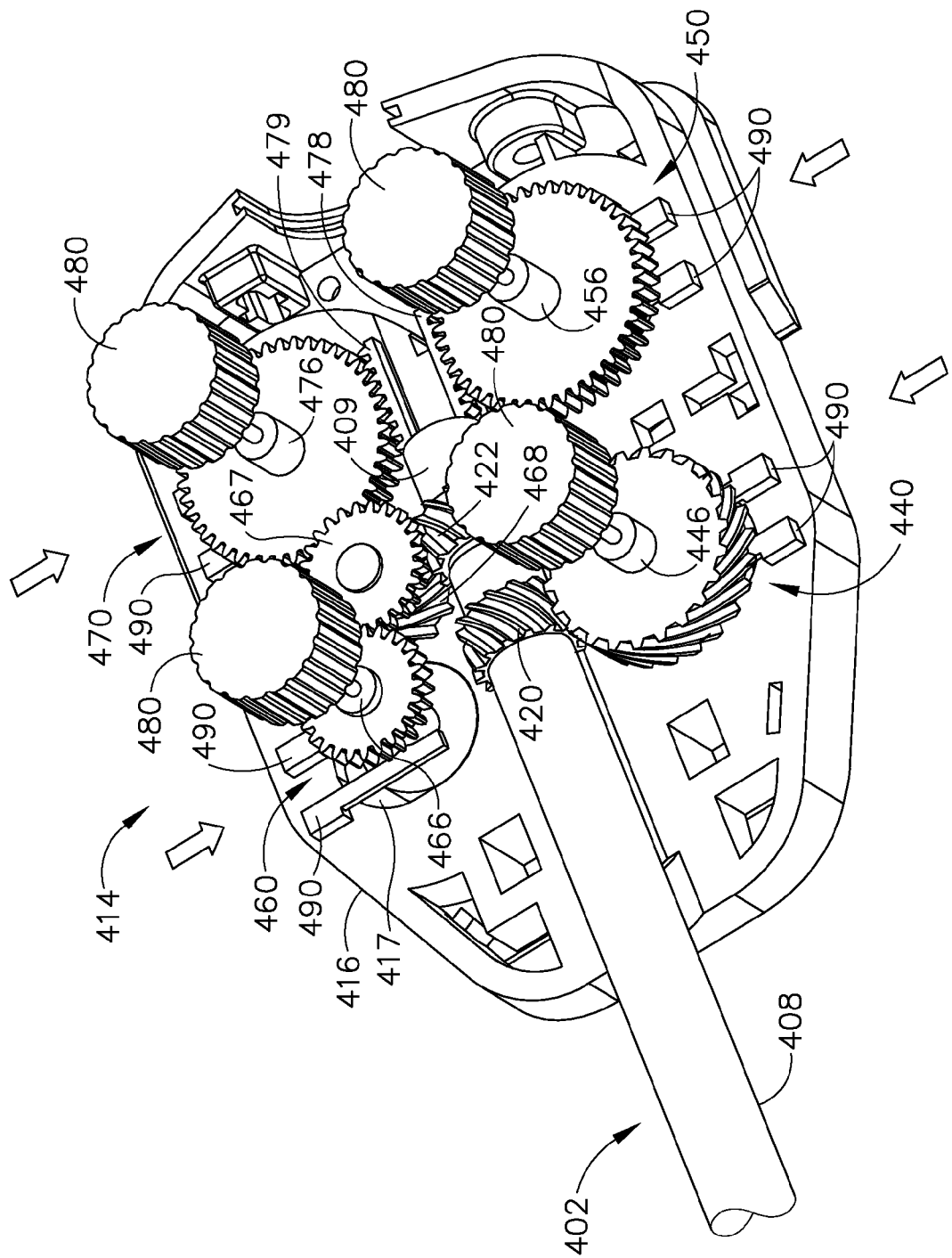
FIG. 44B depicts a partial perspective view of the interface assembly of FIG. 39 in an engaged position.

In an exemplary use, pin assemblies (480) is positioned in the outward position of FIG. 44A such that drive assemblies (440, 450, 460, 470) are in an outward position within interface assembly (410). Shaft assembly (402) may be inserted distally through a proximal end of interface assembly (410). Knobs (482) are then translated inwardly, as shown in FIG. 44B. The translation of knobs (482) thereby translates drive assemblies (440, 450, 460, 470) to engage shaft assembly (402). As drive assemblies (440, 450, 460, 470) are translated, spring clips (490) flex slightly. Spring clips (490) then again engage drive shafts (446, 456, 466, 476) to maintain drive assemblies (440, 450, 460, 470) in the inward position.

After drive assemblies (440, 450, 460, 470) engage shaft assembly (402), instrument (400) may be operated. Arm cart (40) is used to insert end effector (406) into a patient via a trocar. Articulation section (404) is substantially straight when end effector (406) and part of shaft assembly (402) are inserted through the trocar. Drive shaft (466) may be actuated to retract firing beam (190) to thereby pivot jaw (182) away from jaw (184). Drive shaft (446) may be rotated through drive features in dock (72) that are coupled with the corresponding disc (444), to position end effector (406) at a desired angular orientation relative to the tissue. Drive shafts (456, 476) may then be rotated through drive features in dock (72) that are coupled with the corresponding discs (454, 474), to pivot or flex articulation section (404) of shaft assembly (402) in order to position end effector (406) at a desired position and orientation relative to an anatomical structure within the patient. Of course, drive shaft (446) and/or drive shafts (456, 476) may be actuated prior to opening jaws (182, 184). Two layers of tissue of the anatomical structure are then captured between jaws (182, 184) by rotating drive shaft (466) to advance firing beam (190) distally through a first range of motion. As noted above, flanges (192, 196) cammingly act to pivot jaw (182) toward jaw (184) when firing beam (190) is actuated distally by rotating drive shaft (266).

With tissue layers captured between jaws (182, 184) firing beam (190) continues to advance distally in response to continued rotation of drive shaft (466). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (466) may then be actuated in the opposing direction to retract firing beam (190) and open jaws (182, 184) of end effector (406) to release the tissue. Articulation section (404) may be again aligned with shaft assembly (402) by actuating drive shafts (456, 476) and jaws (182, 184) may be re-closed by actuating drive shaft (466). End effector (406) may then be removed from the patient.

Knobs (482) may be translated in the opposing direction to translate drive assemblies (440, 450, 460, 470) back to the initial position shown in FIG. 44A such that drive assemblies (440, 450, 460, 470) disengage shaft assembly (402). Spring clips (490) slightly flex to allow the translation of drive assemblies (440, 450, 460, 470). Shaft assembly (402) is then pulled proximally out of interface assembly (410). Shaft assembly (402) may then be discarded, while interface assembly (410) may be sterilized and reused in another surgical procedure. Of course, various other suitable ways in which instrument (400) may be used will be apparent to those of ordinary skill in the art in view of the teachings herein.

D. Exemplary Translating Drive Assemblies with a Top Rotation Knob Assembly

Figure 45:
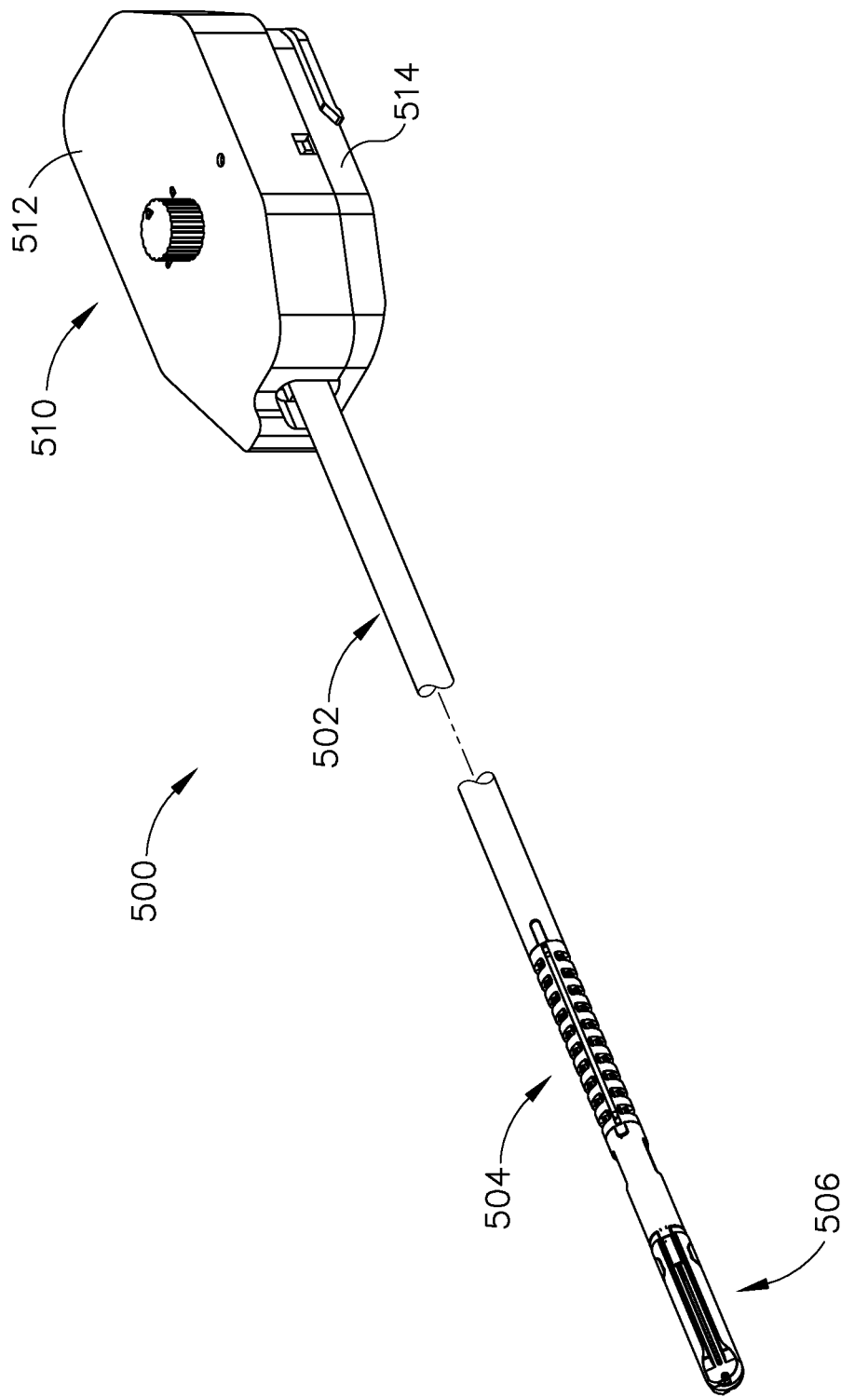
FIG. 45 depicts a perspective view of another exemplary surgical instrument suitable for incorporation with the system of FIG. 1.
Figure 46:
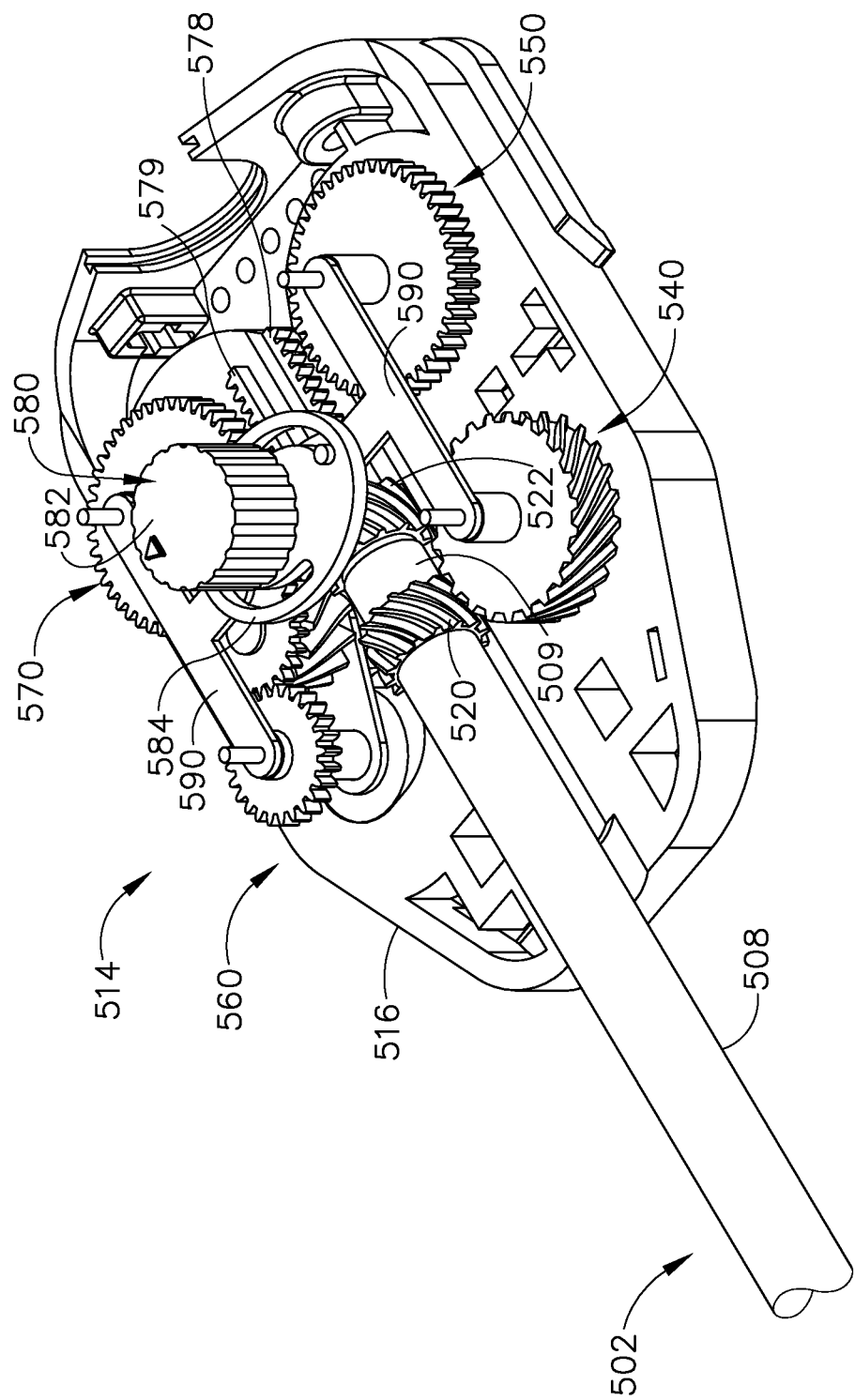
FIG. 46 depicts a partial perspective view of a proximal portion of the shaft assembly and an interface assembly of the instrument of FIG. 45.

FIGS. 45-46 show another exemplary alternative electrosurgical instrument (500) with translating drive assemblies (540, 550, 560, 570). Instrument (500) of this example is substantially similar to instrument (400) described above in that instrument (500) has a shaft assembly (502), an articulation section (504), and an end effector (506) that are substantially identical to shaft assembly (402), articulation section (404), and end effector (406) described above. Shaft assembly (502), first drive assembly (540), second drive assembly (550), third drive assembly (560), and fourth drive assembly (570) are substantially similar to shaft assembly (402), first drive assembly (440), second drive assembly (450), third drive assembly (460), and fourth drive assembly (470) described above. Instrument (500) of this example is also operable to couple with a dock (72) of robotic arm cart (40) via an interface assembly (510). Interface assembly (510) of this example is similar to interface assembly (410), except that interface assembly (510) comprises a rotation knob assembly (580) configured to translate drive assemblies (540, 550, 560, 570) instead of a plurality of pin assemblies (480).

Rotation knob assembly (580) comprises a rotation knob (582), a pin (586) extending downwardly from rotation knob (582), and a plate (584), as shown in FIGS. 47-48. Pin (586) extends through an opening in housing (512) such that rotation knob (582) is positioned above housing (512) and plate (584) is positioned within housing (512). In the present example, an indicator (583) is positioned on a top surface of rotation knob (582) to provide a visual indication of the rotational position of rotation knob (582). As rotation knob (582) rotates, pin (586) and plate (584) rotate with rotation knob (582). As best seen in FIG. 49, plate (584) has an elliptical shape and comprises a pair of channels (588) having curved profiles. Each channel (588) extends around about a quarter of plate (584) and is configured to receive a link (590), shown in FIG. 50. Link (590) comprises a first member (594) with a protrusion (596). Protrusion (596) is configured to translate within a channel (588) of plate (584). First member (594) extends outwardly from plate (584) and connects to second member (592) positioned transversely to first member (594). Second member (592) comprises openings (598) on each end portion of second member (592). Openings (598) are configured to couple with corresponding drive shafts (546, 556, 566, 576) of drive assemblies (540, 550, 560, 570).

Figure 51B:
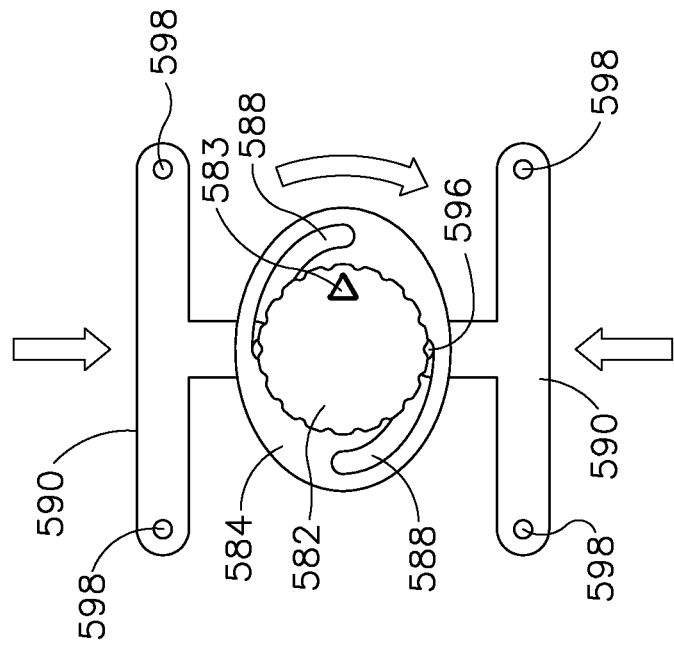
FIG. 51B depicts a top plan view of the knob assembly of FIG. 47 in an engaged position.
Figure 51A:
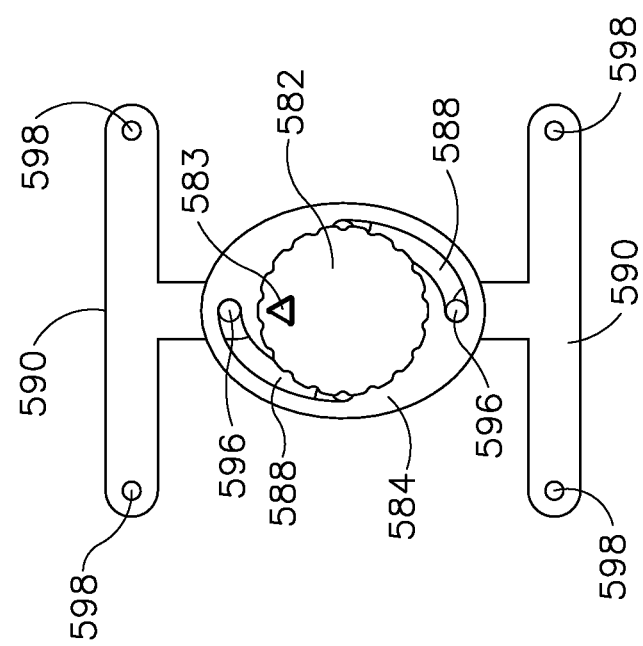
FIG. 51A depicts a top plan view of the knob assembly of FIG. 47 in an initial position.

As rotation knob assembly (580) is actuated, links (590) are configured to translate drive assemblies (540, 550, 560, 570). As shown in FIG. 51A, rotation knob assembly (580) is positioned in an initial position such that elliptical plate (584) is positioned transverse to interface assembly (510). Accordingly, links (590) are in an outward position. Rotation knob (582) is then rotated about 90 degrees, as shown in FIG. 51B. As rotation knob (582) rotates, plate (584) rotates to longitudinally align plate (584) with interface assembly (510). As plate (584) rotates, protrusions (596) of links (590) translate within channels (588) of plate (584). This pulls links (590) inwardly to thereby translate drive assemblies (540, 550, 560, 570) inwardly, which in turn engages drive assemblies (540, 550, 560, 570) with shaft assembly (502). In the present example, rotation knob (582) is rotated clockwise. However, rotation knob (582) may be configured to rotate counterclockwise.

Figure 52A:
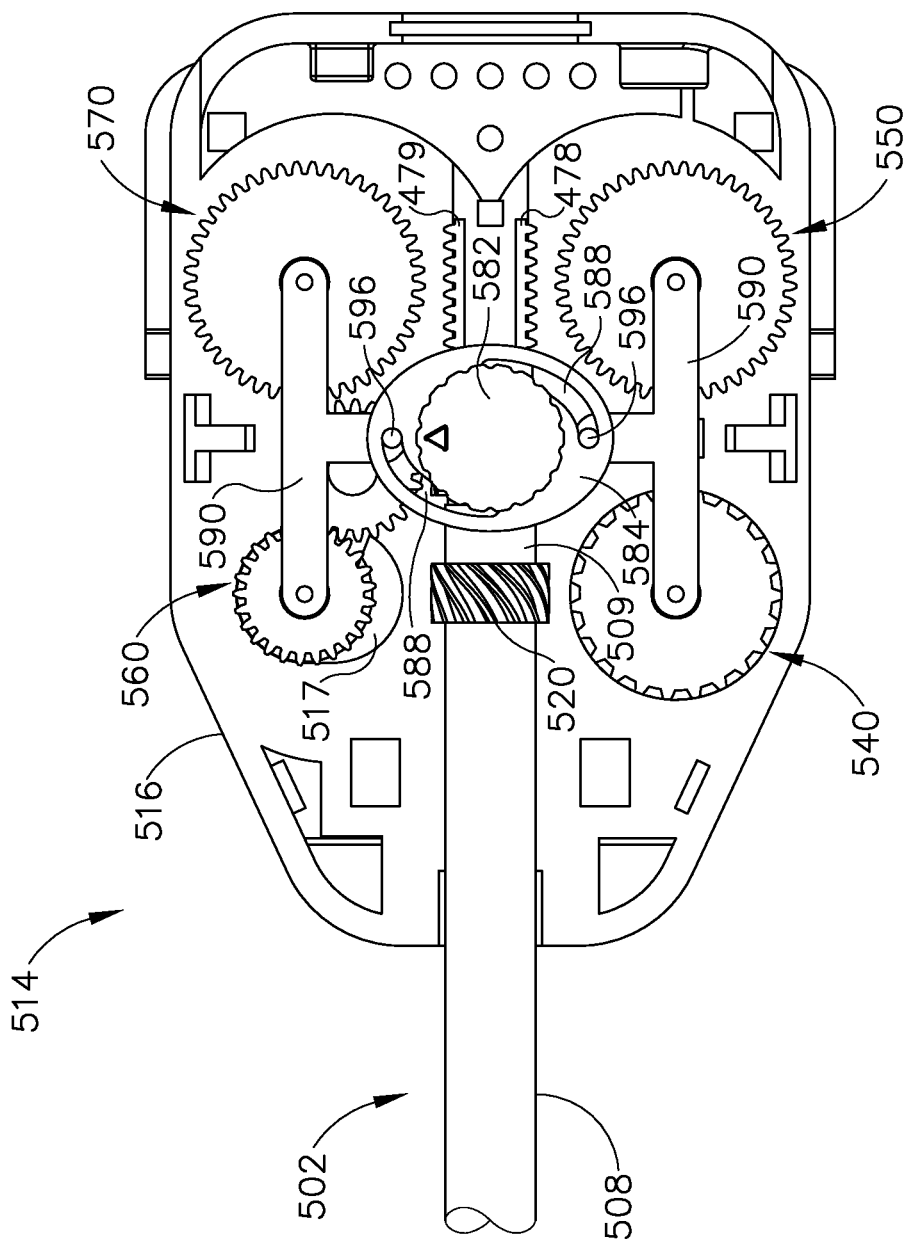
FIG. 52A depicts a partial top view of the interface assembly of FIG. 46 in an initial position.
Figure 52B:
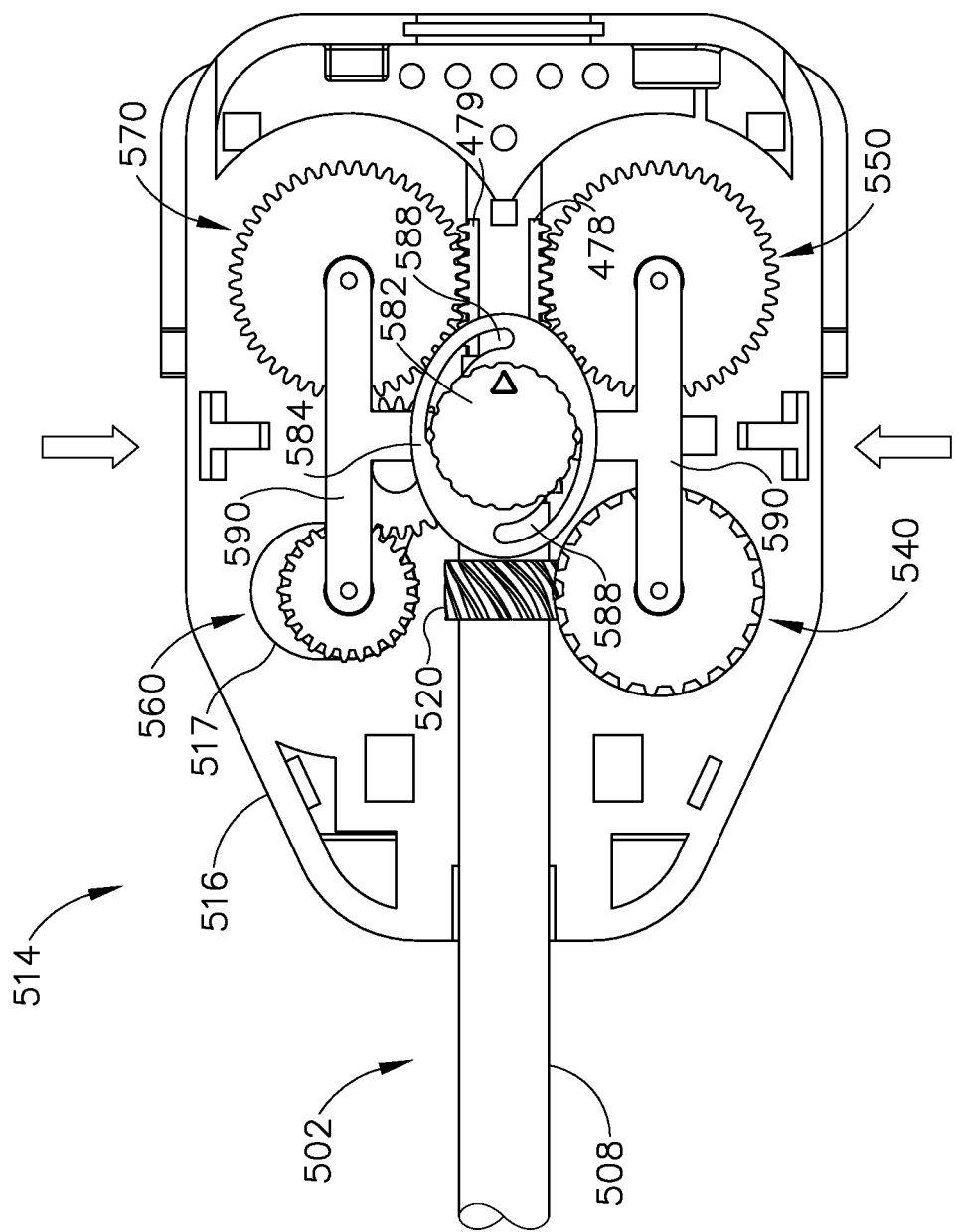
FIG. 52B depicts a partial top view of the interface assembly of FIG. 46 in an engaged position.

In an exemplary use, rotation knob assembly (580) is positioned in the initial position of FIG. 52A such that drive assemblies (540, 550, 560, 570) are in an outward position within interface assembly (510). Shaft assembly (502) may be inserted distally through a proximal end of interface assembly (510). A user may rotate rotation knob assembly (380) about a quarter turn to translate links (590) within interface assembly (510). Accordingly, each corresponding drive assembly (540, 550, 560, 570) engages shaft assembly (502), as shown in FIG. 52B. After drive assemblies (540, 550, 560, 570) engage shaft assembly (502), instrument (500) may be operated similar to instrument (400) described above to sever and weld tissue. After use of instrument (500), rotation knob (582) may be rotated in the opposite direction such that links (590) translate outwardly to thereby translate drive assemblies (540, 550, 560, 570) to disengage shaft assembly (502), as shown in FIG. 52A. Shaft assembly (502) is then pulled proximally out of interface assembly (510). Shaft assembly (502) may then be discarded, while interface assembly (510) may be sterilized and reused in another surgical procedure. Of course, various other suitable ways in which instrument (500) may be used will be apparent to those of ordinary skill in the art in view of the teachings herein.

Figure 53:
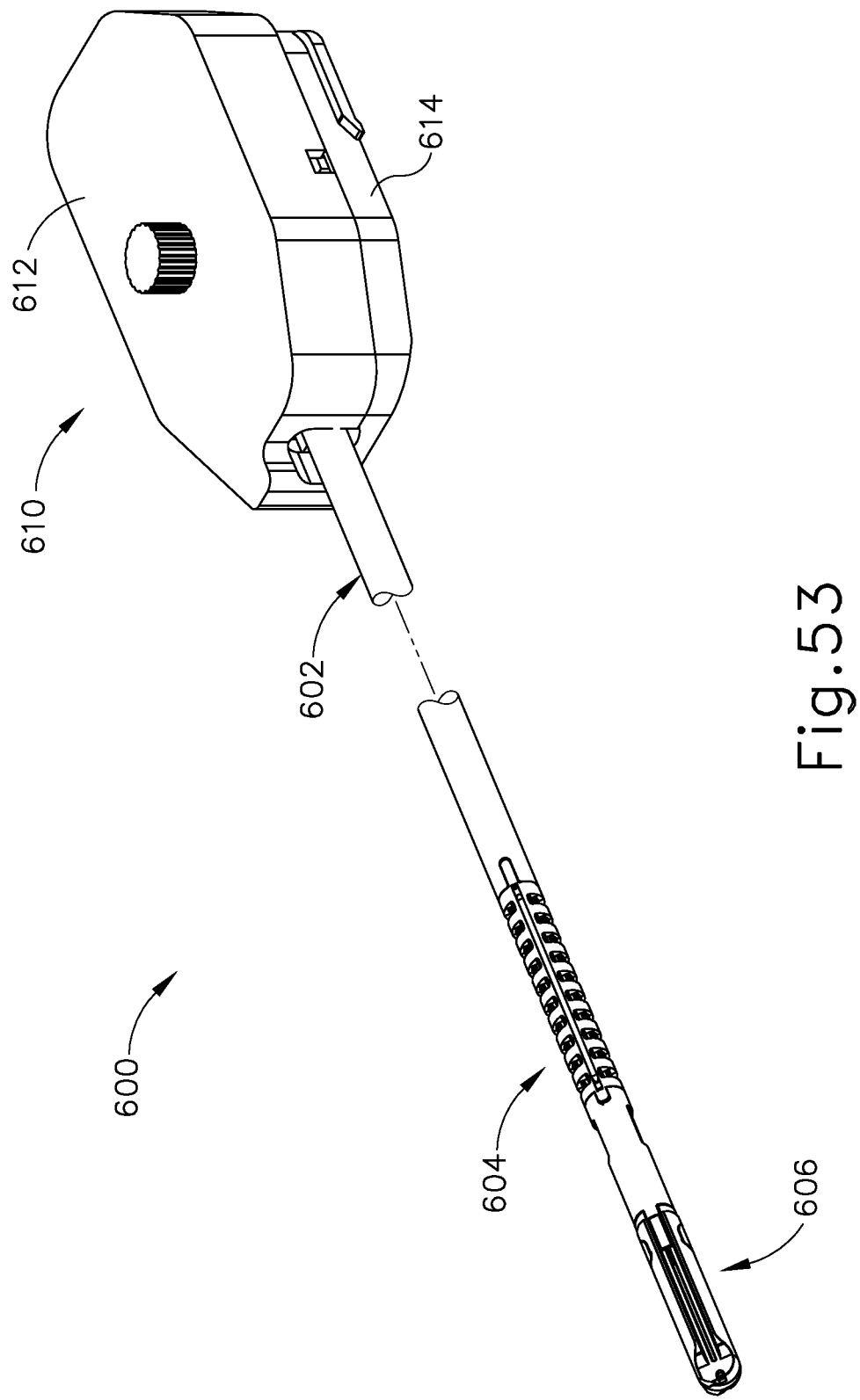
FIG. 53 depicts a perspective view of another exemplary surgical instrument suitable for incorporation with the system of FIG. 1.
Figure 54:
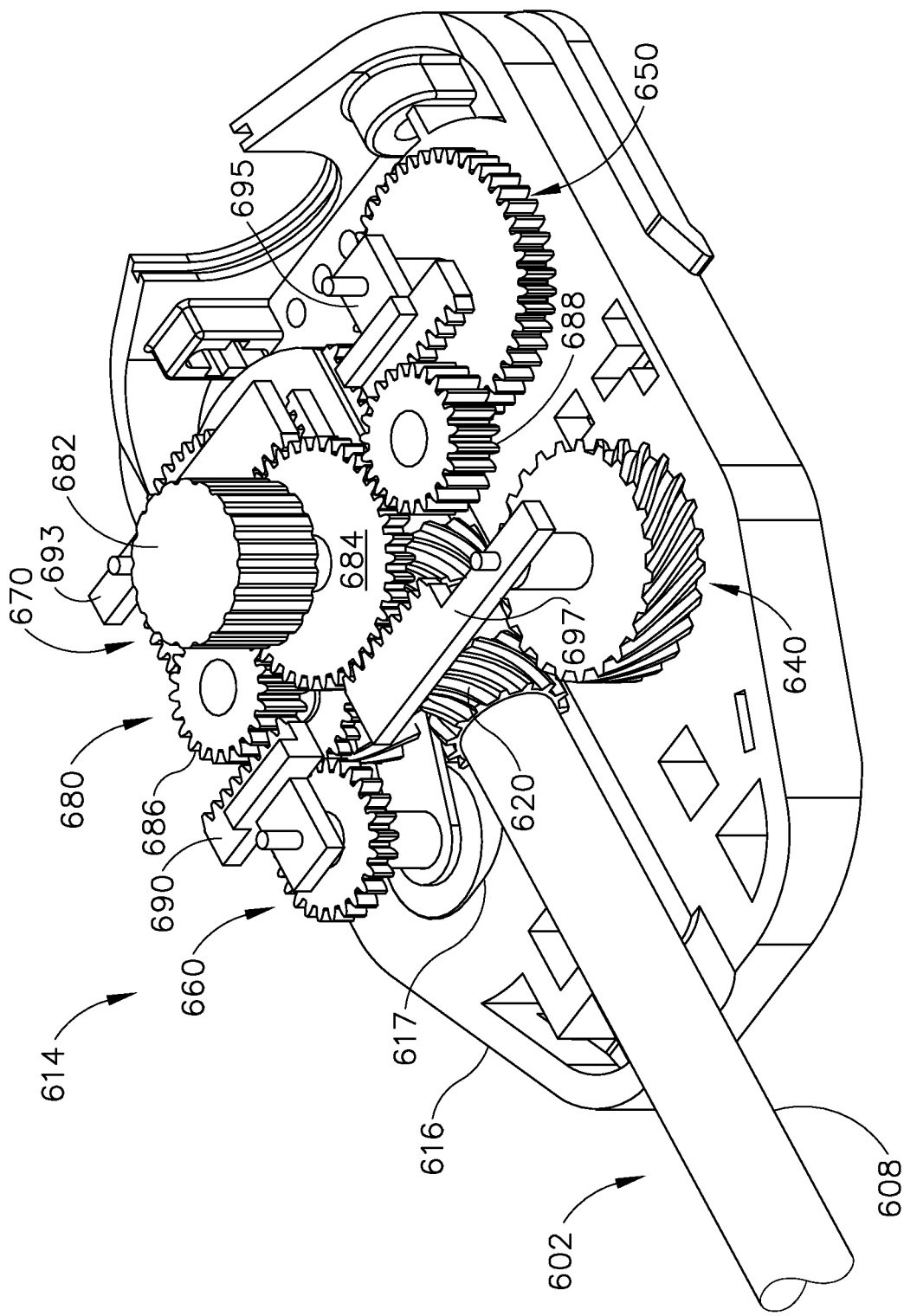
FIG. 54 depicts a partial perspective view of a proximal portion of the shaft assembly and an interface assembly of the instrument of FIG. 53.

E. Exemplary Translating Drive Assemblies with a Top Rotation Knob Gear Assembly FIGS. 53-54 show another exemplary alternative electrosurgical instrument (600) with translating drive assemblies (640, 650, 660, 670). Instrument (600) of this example is substantially similar to instrument (400) described above in that instrument (600) has a shaft assembly (602), an articulation section (604), and an end effector (606) that are substantially identical to shaft assembly (402), articulation section (404), and end effector (406) described above. First drive assembly (640), second drive assembly (650), third drive assembly (660), and fourth drive assembly (670) are also substantially identical to first drive assembly (440), second drive assembly (450), third drive assembly (460), and fourth drive assembly (470). Instrument (600) of this example is also operable to couple with a dock (72) of robotic arm cart (40) via an interface assembly (610). Interface assembly (610) of this example is similar to interface assembly (410), except that interface assembly (610) comprises a rotation knob gear assembly (680) configured to translate drive assemblies (640, 650, 660, 670) instead of a plurality of pin assemblies (480).

Figure 55:
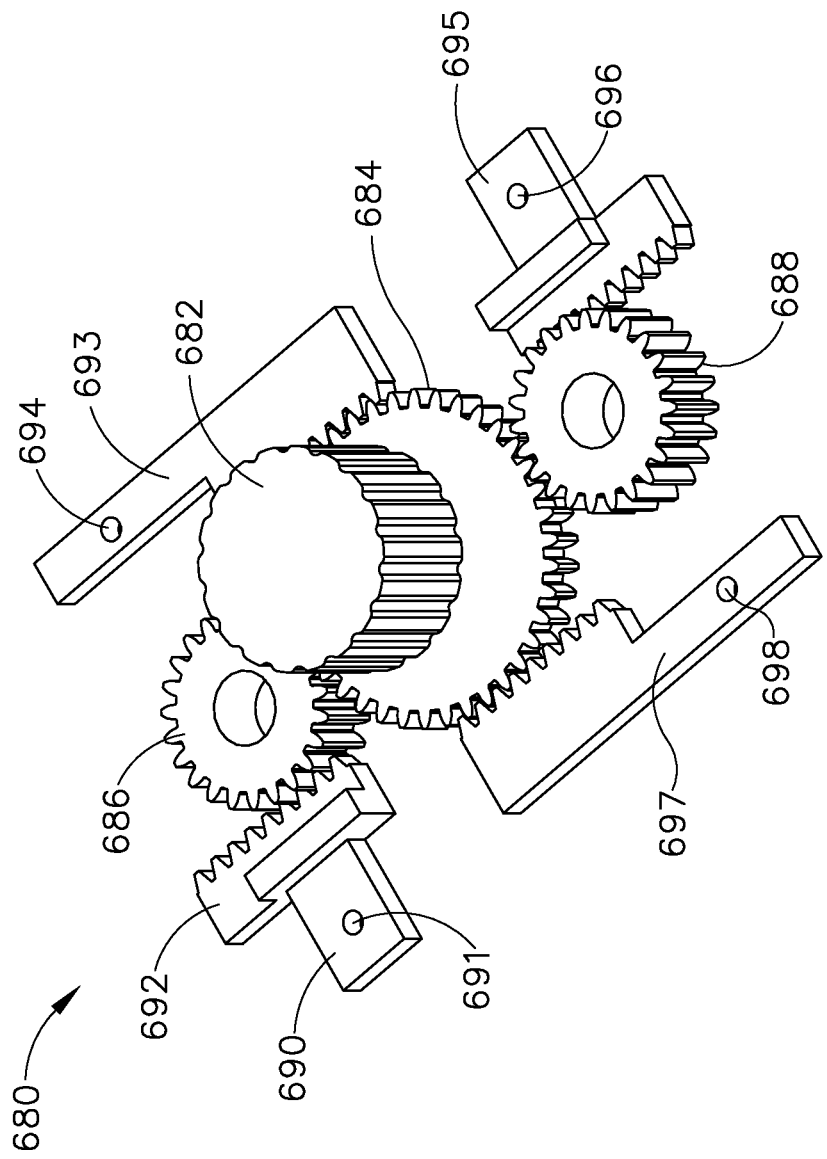
FIG. 55 depicts a perspective view of a gear assembly of the interface assembly of FIG. 54.

Rotation knob gear assembly (680) comprises a rotation knob (682), gears (684, 686, 688), and racks (692, 693, 695, 697), as shown in FIG. 55. Rotation knob (682) is coupled with first gear (684) via a pin (not shown) such that rotation knob (682) and first gear (684) rotate unitarily. The pin extends through housing (612) between rotation knob (682) and first gear (684) such that rotation knob (682) is positioned above housing (612) and first gear (684) is positioned within housing (612). First gear (684) is coupled with first rack (697) and second rack (693) on opposing sides of first gear (684). Accordingly, as first gear (684) is rotated by rotation knob (682), first rack (697) and second rack (693) translate in opposing directions. First rack (697) comprises an opening (698) to receive drive shaft (446) of first drive assembly (440). Second rack (693) comprises an opening (694) to receive drive shaft (676) of fourth drive assembly (670). First gear (684) is also coupled with second gear (686) and third gear (688). Second and third gears (686, 688) may be supported by pins (not shown) on mounting plate (616). Second gear (686) is coupled with third rack (692). Third rack (692) comprises an opening (691) to receive drive shaft (666) of third drive assembly (660). Third gear (688) is coupled with fourth rack (695). Fourth rack (695) comprises an opening (696) to receive drive shaft (656) of second drive assembly (650). As rotation knob (682) is rotated, first gear (684) rotates second gear (686) and third gear (688) to thereby translate third and fourth racks (692, 695) in opposing directions.

Figure 56B:
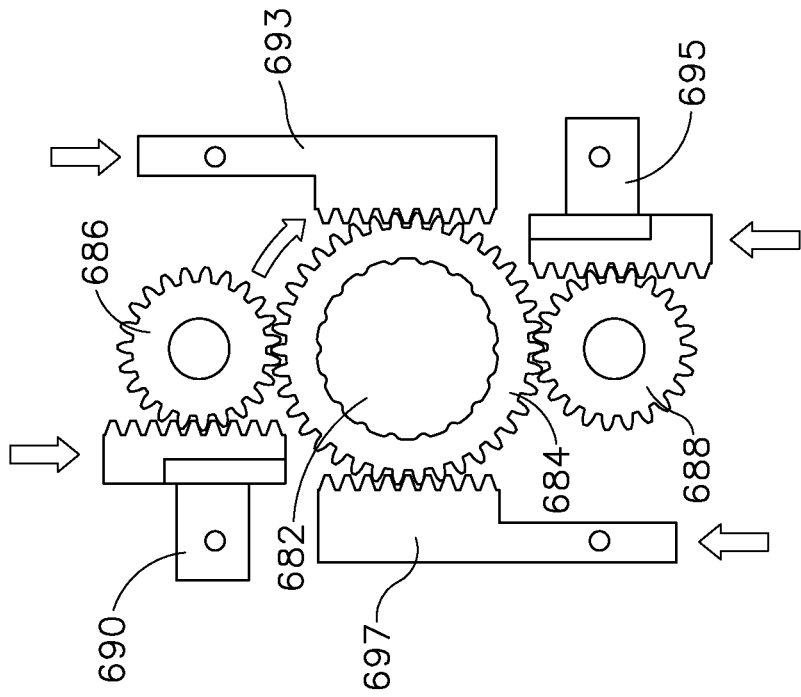
FIG. 56B depicts a top plan view of the gear assembly of FIG. 55 in an engaged position.
Figure 56A:
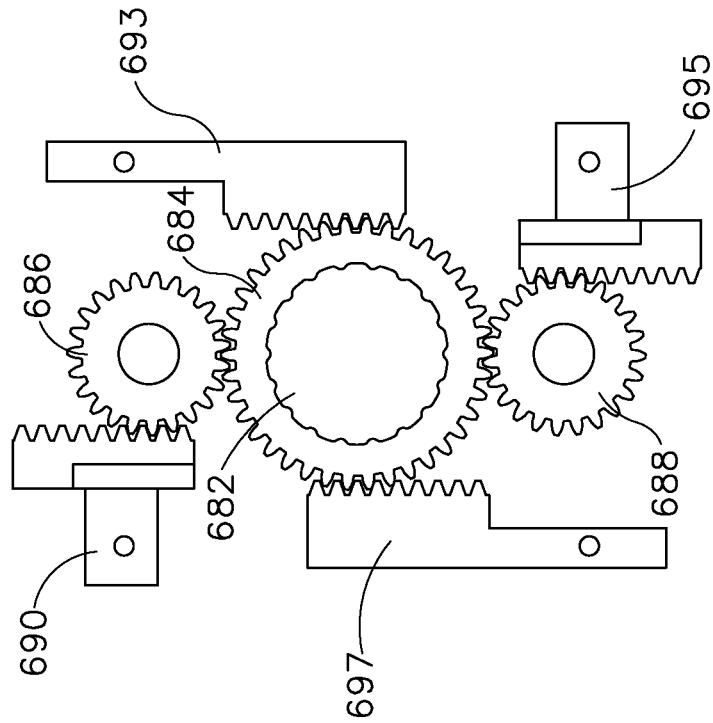
FIG. 56A depicts a top plan view of the gear assembly of FIG. 55 in an initial position.

As rotation knob gear assembly (680) is actuated, racks (692, 693, 695, 697) are configured to translate drive assemblies (640, 650, 660, 670). As shown in FIG. 56A, rotation knob gear assembly (680) is positioned in an initial position such that racks (692, 693, 695, 697) are positioned outwardly within interface assembly (610). Rotation knob (682) is then rotated, as shown in FIG. 56B. As rotation knob (682) rotates clockwise, first gear (684) rotates clockwise to translate first rack (697) and second rack (693) inwardly within interface assembly (610). First gear (684) also rotates second gear (686) and third gear (688) in the counterclockwise direction. Second gear (686) thereby translates third rack (692) inwardly within interface assembly (610) and third gear (688) thereby translates fourth rack (695) inwardly within interface assembly (610). Racks (692, 693, 695, 697) thus pull drive assemblies (640, 650, 660, 670) inwardly. In the present example, rotation knob (682) is rotated clockwise. However, rotation knob (682) may be configured to rotate counterclockwise.

Figure 57A:
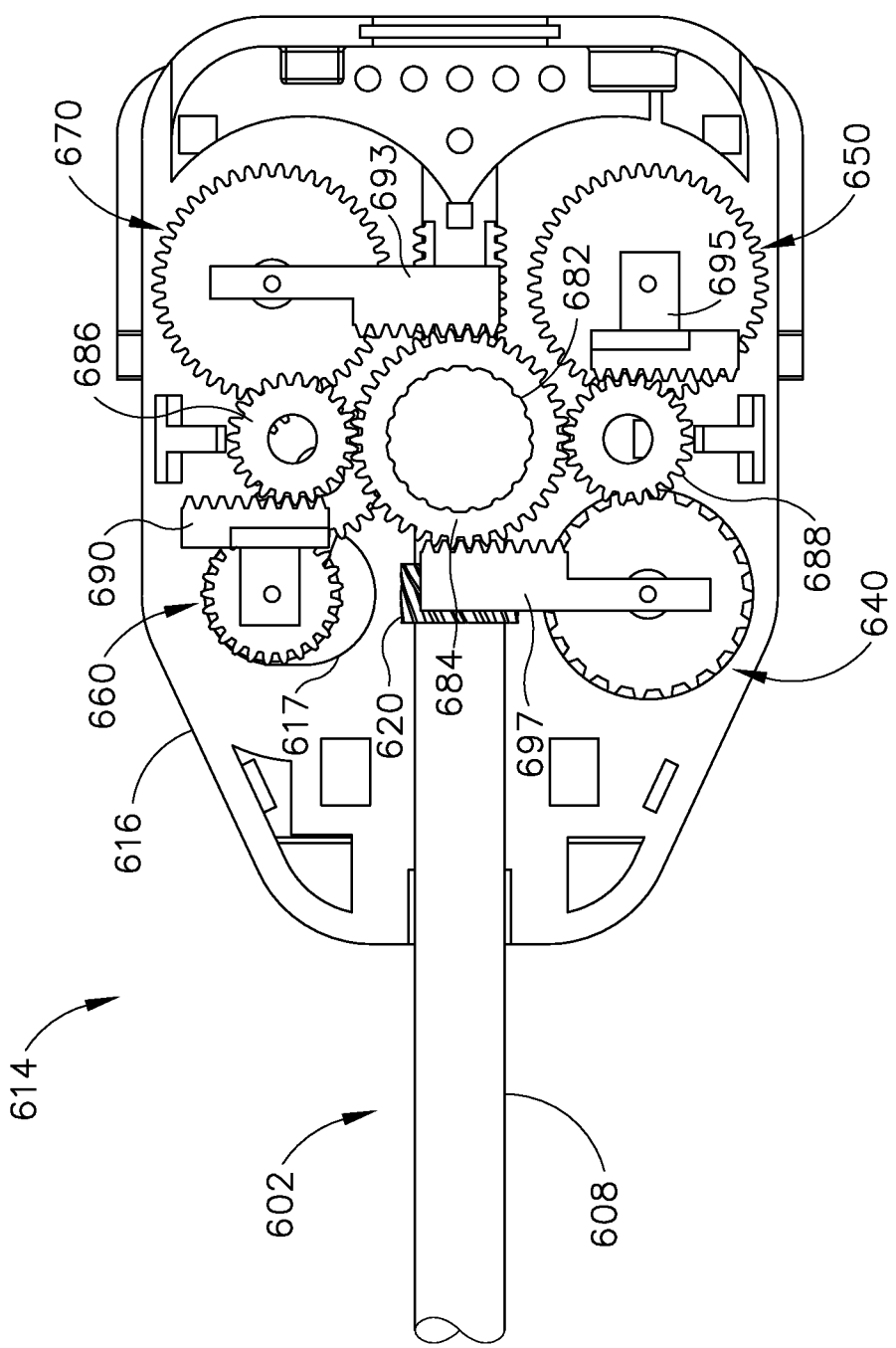
FIG. 57A depicts a partial top view of the interface assembly of FIG. 54 in an initial position.
Figure 57B:
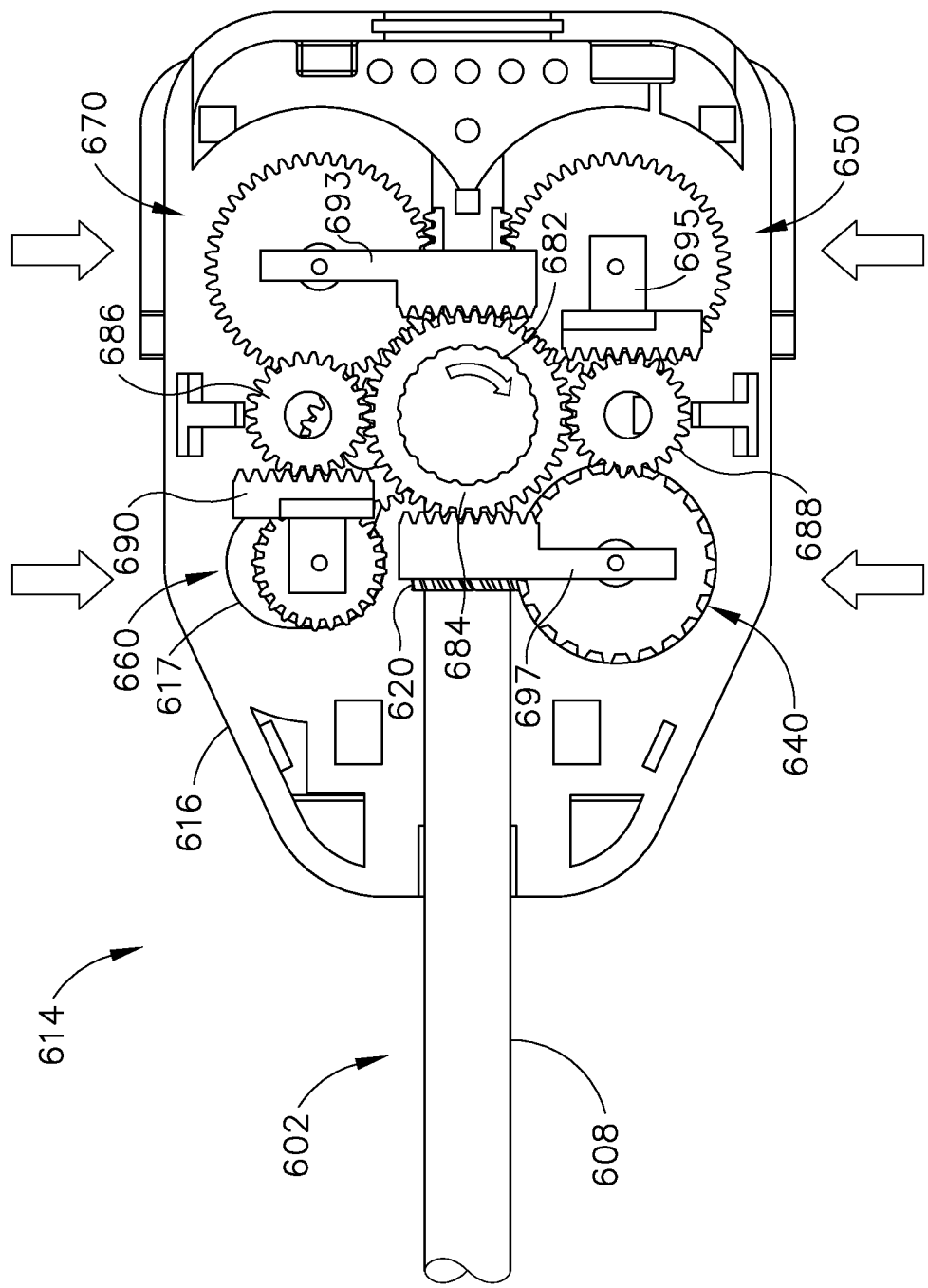
FIG. 57B depicts a partial top view of the interface assembly of FIG. 54 in an engaged position.

In an exemplary use, rotation knob gear assembly (680) is positioned in the initial position of FIG. 57A such that drive assemblies (640, 650, 660, 670) are in an outward position within interface assembly (610). Shaft assembly (602) may be inserted distally through a proximal end of interface assembly (610). A user may rotate rotation knob (682) to rotate gears (684, 686, 688). Gears (684, 686, 688) then translate racks (692, 693, 695, 697) inwardly within interface assembly (610). Accordingly, each corresponding drive assembly (640, 650, 660, 670) engages shaft assembly (602), as shown in FIG. 57B. After drive assemblies (640, 650, 660, 670) engage shaft assembly (602), instrument (600) may be operated similar to instrument (400) described above to sever and weld tissue. After use of instrument (600), rotation knob (682) may be rotated in the opposing direction such that racks (692, 693, 695, 697) translate outwardly to thereby translate drive assemblies (640, 650, 660, 670) to disengage shaft assembly (602), as shown in FIG. 57A. Shaft assembly (602) is then pulled proximally out of interface assembly (610). Shaft assembly (602) may then be discarded, while interface assembly (610) may be sterilized and reused in another surgical procedure. Of course, various other suitable ways in which instrument (600) may be used will be apparent to those of ordinary skill in the art in view of the teachings herein.

Figure 58:
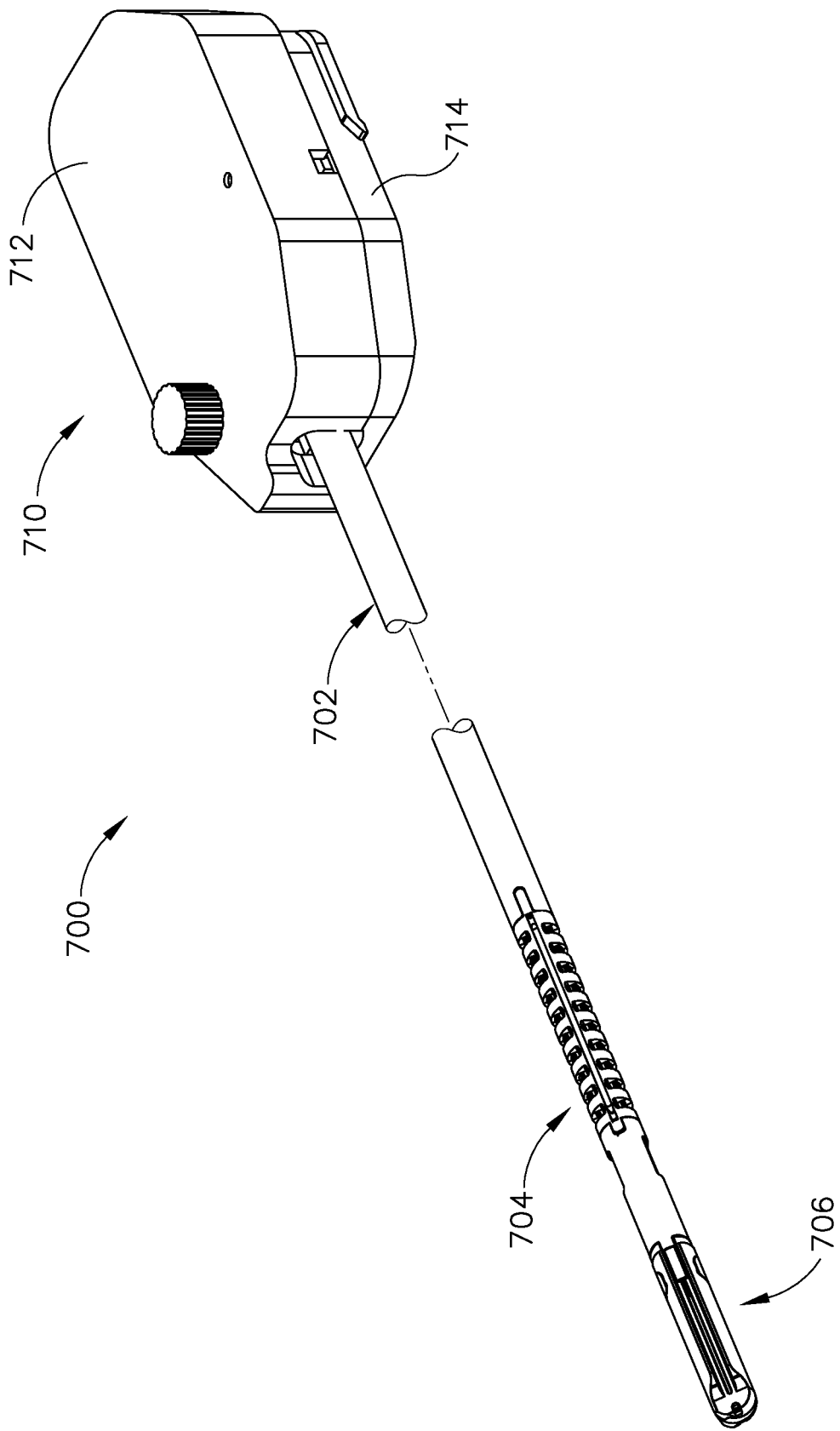
FIG. 58 depicts a perspective view of another exemplary surgical instrument suitable for incorporation with the system of FIG. 1.
Figure 59:
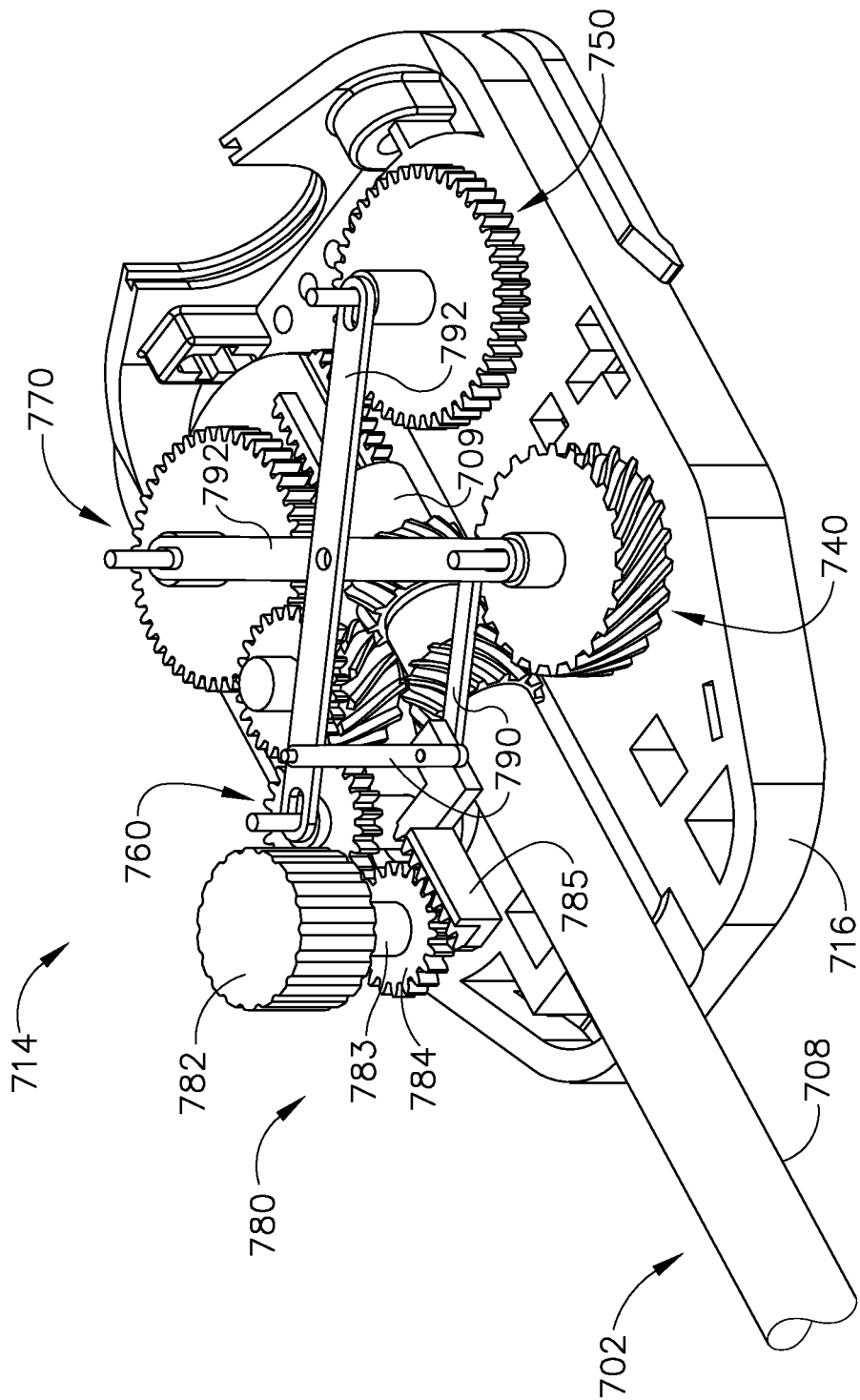
FIG. 59 depicts a partial perspective view of a proximal portion of the shaft assembly and an interface assembly of the instrument of FIG. 58.

F. Exemplary Translating Drive Assemblies with a Top Rotation Knob Linkage Assembly FIGS. 58-59 show another exemplary alternative electrosurgical instrument (700) with translating drive assemblies (740, 750, 760, 770). Instrument (700) of this example is substantially similar to instrument (400) described above in that instrument (700) has a shaft assembly (702), an articulation section (704), and an end effector (706) that are substantially identical to shaft assembly (402), articulation section (404), and end effector (406) described above. First drive assembly (740), second drive assembly (750), third drive assembly (760), and fourth drive assembly (770) are also substantially identical to first drive assembly (440), second drive assembly (450), third drive assembly (460), and fourth drive assembly (470). Instrument (700) of this example is also operable to couple with a dock (72) of robotic arm cart (40) via an interface assembly (710). Interface assembly (710) of this example is similar to interface assembly (410), except that interface assembly (710) comprises a rotation knob linkage assembly (780) configured to translate drive assemblies (740, 750, 760, 770) instead of a plurality of pin assemblies (480).

Figure 60:
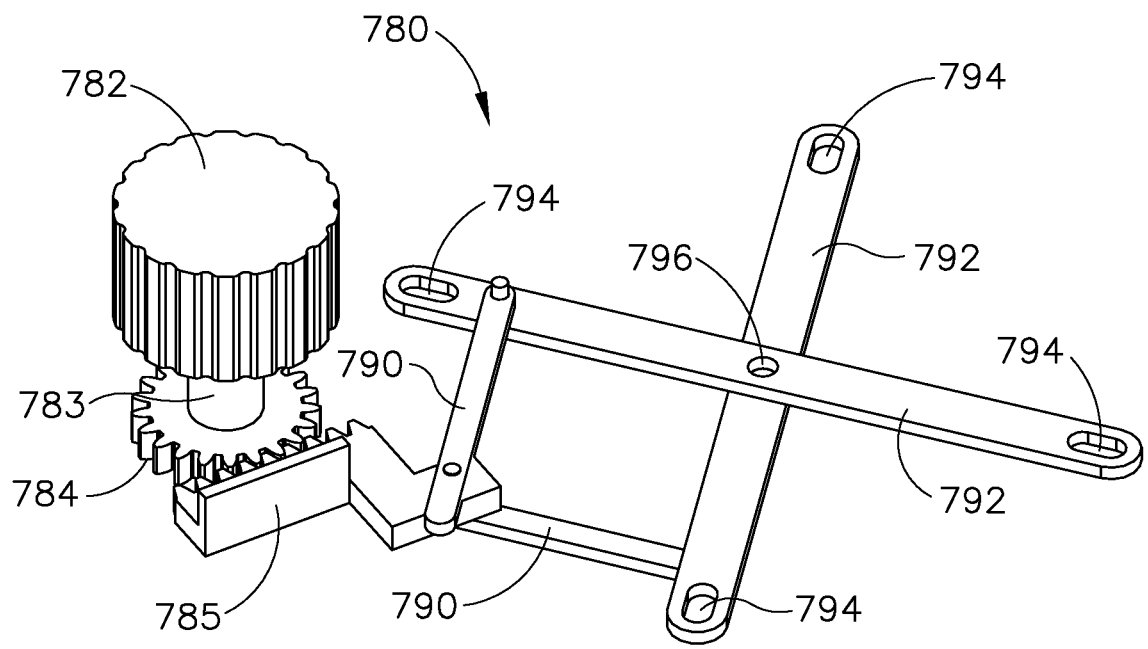
FIG. 60 depicts a perspective view of a linkage assembly of the interface assembly of FIG. 59.
Figure 61:
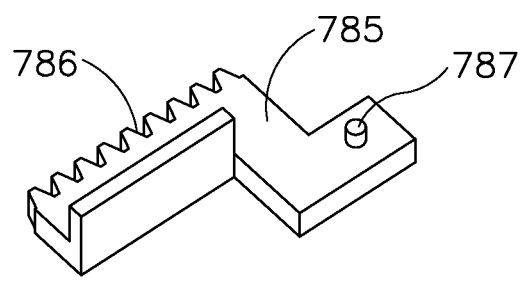
FIG. 61 depicts a perspective view of a translating member of the linkage assembly of FIG. 60.
Figure 62:
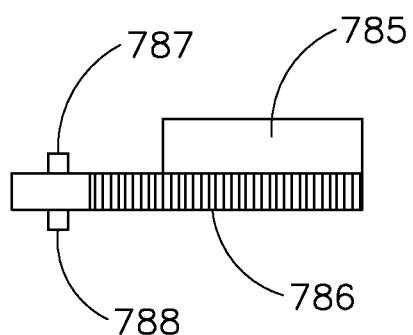
FIG. 62 depicts a side elevational view of the translating member of FIG. 61.

FIG. 60 shows rotation knob linkage assembly (780) in greater detail. Rotation knob linkage assembly (780) comprises a rotation knob (782), gear (783), rack (785), and linkages (790, 792). Rotation knob (782) is coupled to gear (784) via pin (783) such that rotation knob (782) and gear (784) rotate unitarily. Rotation knob (782) is positioned above housing (712) and pin (783) extends through housing (712) into interface assembly (710). Gear (784) is coupled with rack (785). As shown in FIGS. 61-62, rack (785) comprises a longitudinal row of teeth (786) to engage the teeth of gear (784). Rack (785) further comprises a protrusion (787) extending upwardly from rack (785) and a protrusion (788) extending downwardly from rack (785). Each protrusion (787, 788) is disposed in a respective opening of a corresponding link (790) such that each link (790) is pivotable relative to rack (785), as shown in FIG. 60. The opposing end of each link (790) is pivotally coupled to an end portion of a corresponding link (792) such that links (792) are pivotable relative to links (790). Each link (792) comprises an opening (796) in the central portion of link (792). A pin (not shown) may be inserted within openings (796) to pivotally couple links (792) with each other and interface assembly (710). Each link (792) comprises an elongate opening (794) on each end of each link (792). Openings (794) are configured to receive drive shafts (746, 756, 766, 776) of drive assemblies (740, 750, 760, 770) such that drive shafts (746, 756, 766, 776) are translatable within openings (794). Although four links (790, 792) are shown, any other suitable number of links (790, 792) may be used.

Figure 63B:
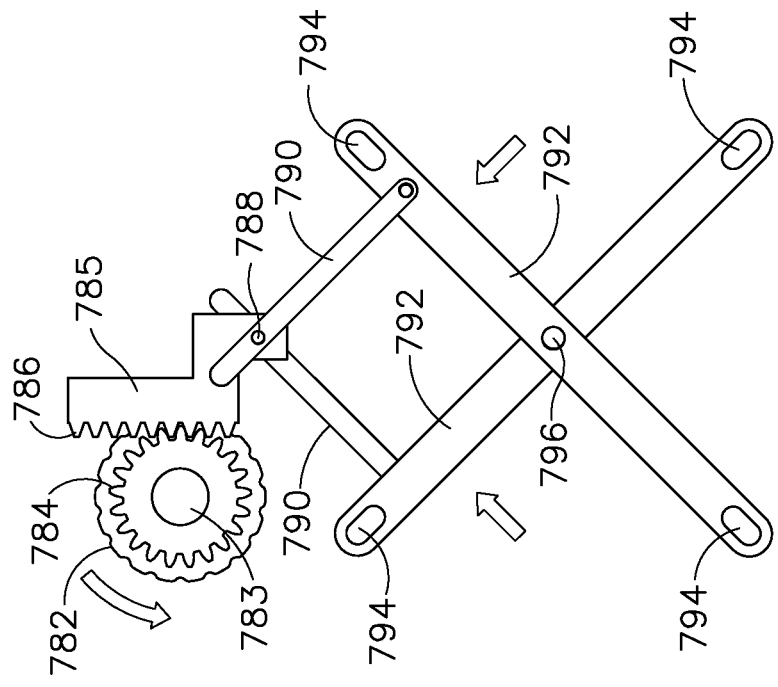
FIG. 63B depicts a top plan view of the linkage assembly of FIG. 60 in an engaged position.
Figure 63A:
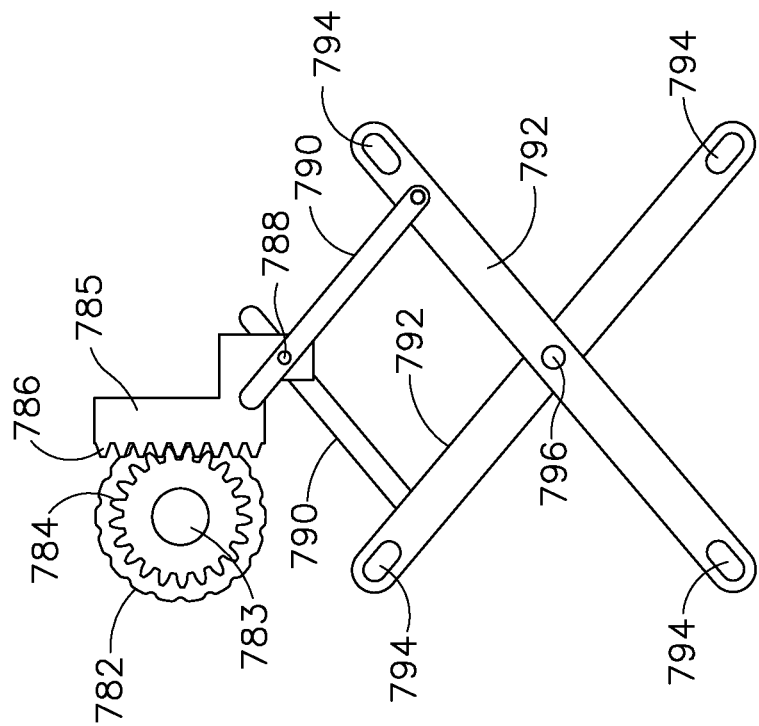
FIG. 63A depicts a top plan view of the linkage assembly of FIG. 60 in an initial position.

As rotation knob linkage assembly (780) is actuated, links (790, 792) are pivoted to translate drive assemblies (740, 750, 760, 770). As shown in FIG. 63A, rotation knob linkage assembly (780) is positioned in an initial position such that links (790, 792) are positioned outwardly within interface assembly (710). Rotation knob (782) is then rotated, as shown in FIG. 63B. As rotation knob (782) rotates, gear (784) rotates to translate rack (785) distally. As rack (785) translates distally, rack (785) pivots links (790) toward each other. Links (790) thereby pivot links (792) inwardly towards each other. Openings (794) of links (792) accordingly translate inwardly to translate drive assemblies (740, 750, 760, 770) inwardly.

Figure 64A:
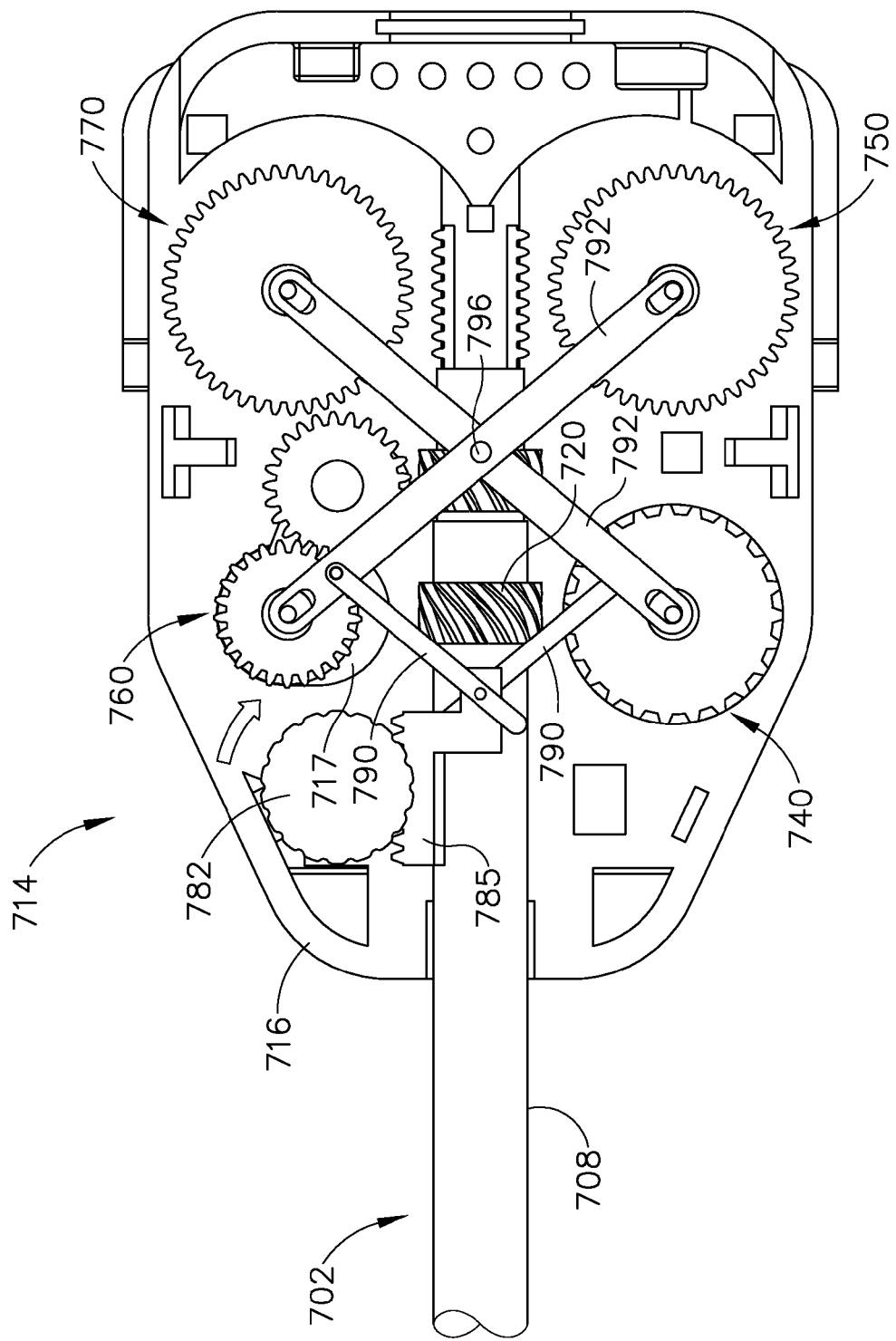
FIG. 64A depicts a partial top view of the interface assembly of FIG. 59 in an initial position.

In an exemplary use, rotation knob linkage assembly (780) is positioned in the initial position of FIG. 64A such that drive assemblies (740, 750, 760, 770) are in an outward position within interface assembly (710). Shaft assembly (702) may be inserted distally through a proximal end of interface assembly (710). A user may rotate rotation knob (782) to translate rack (785) distally. Rack (785) then pivots links (790, 792) inwardly within interface assembly (710). Accordingly, each corresponding drive assembly (740, 750, 760, 770) engages shaft assembly (702), as shown in FIG. 64B. After drive assemblies (740, 750, 760, 770) engage shaft assembly (702), instrument (700) may be operated similar to instrument (400) described above to sever and weld tissue. After use of instrument (700), rotation knob (782) may be rotated in the opposite direction such that rack (785) translates proximally to thereby pivot links (790, 792) to translate drive assemblies (740, 750, 760, 770) outwardly to disengage shaft assembly (702), as shown in FIG. 64A. Shaft assembly (702) is then pulled proximally out of interface assembly (710). Shaft assembly (702) may then be discarded, while interface assembly (710) may be sterilized and reused in another surgical procedure. Of course, various other suitable ways in which instrument (700) may be used will be apparent to those of ordinary skill in the art in view of the teachings herein.

G. Exemplary Rotatable Engagement Assembly

Figure 65:
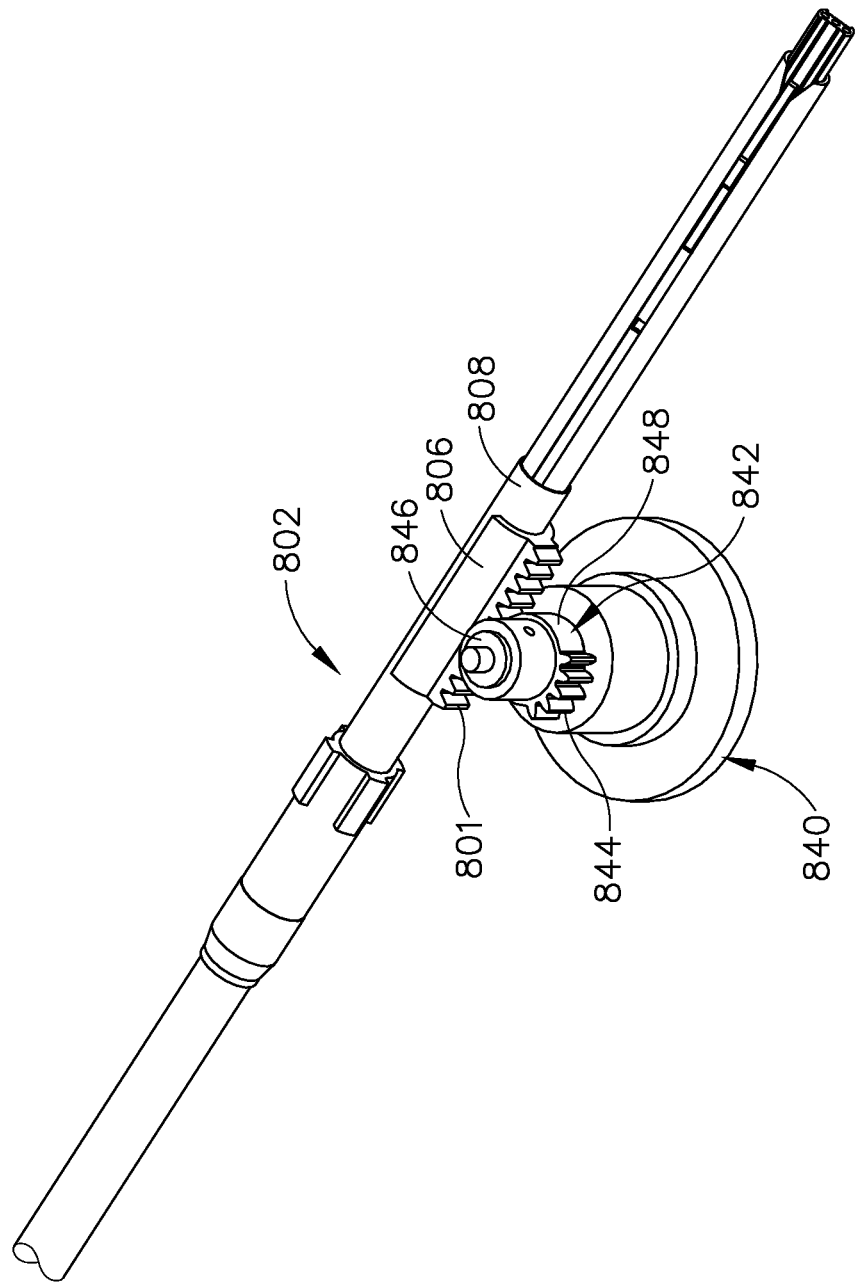
FIG. 65 depicts a partial perspective view of an exemplary gear assembly suitable for use with the interface assembly of the instrument of FIG. 14.

FIG. 65 shows an exemplary rotatable engagement gear (842) for use on a drive assembly (840) to selectively engage and/or disengage a shaft assembly (802). Gear (842) is formed as a sector gear such that gear (842) comprises teeth (844) positioned around a portion of gear (842) and such that gear (842) comprises a smooth portion (848). Gear (842) is positioned around a drive shaft (846) of a drive assembly (840) such that gear (842) rotates with drive shaft (846). A rack (806) is positioned on shaft assembly (802). Rack (806) comprises a longitudinal row of teeth (801) configured to engage gear (842). Gear (842) is positioned such that smooth portion (848) initially faces shaft assembly (802). Shaft assembly (802) may then freely translate relative to drive assembly (840). Once rack (806) is aligned adjacent to gear (842), gear (842) is rotated such that teeth (844) engage teeth (801) of shaft assembly (802). Shaft assembly (802) then translates as gear (842) is rotated through drive shaft (846). Gear (842) may again be rotated such that teeth (844) disengage teeth (801), with smooth portion (848) facing shaft assembly (802), such that shaft assembly (802) may freely translate to be removed from an interface assembly (810). Rotatable engagement gear (842) may be readily incorporated to any of the drive assemblies described above.

Figure 66A:
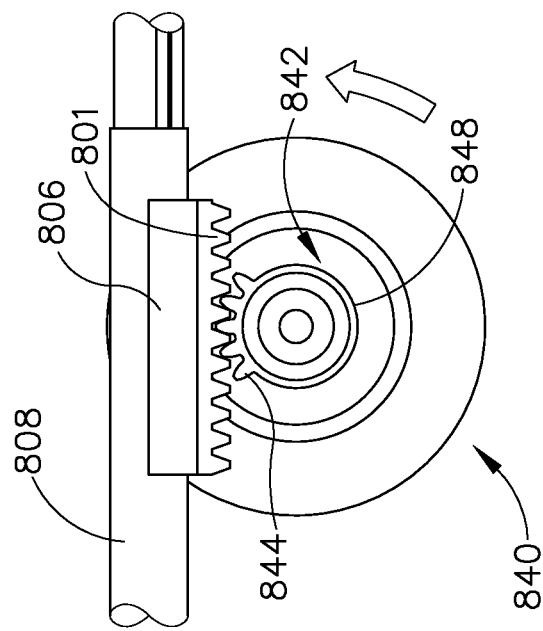
FIG. 66A depicts a partial top plan view of the gear assembly of FIG. 65 in an initial position.
Figure 66B:
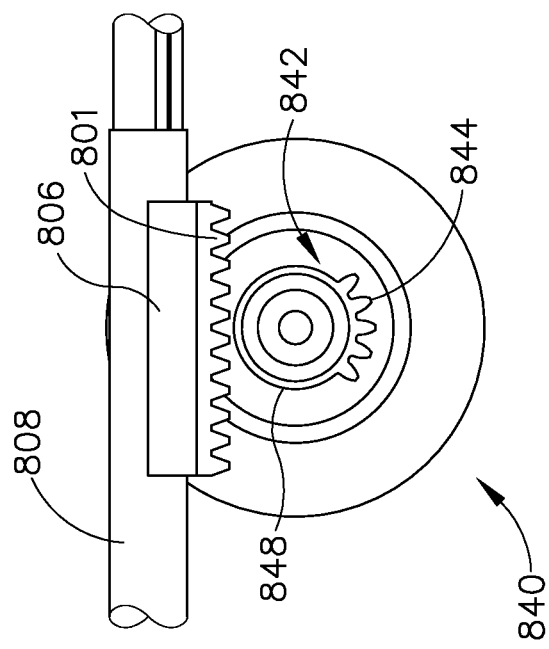
FIG. 66B depicts a partial top plan view of the gear assembly of FIG. 65 in an engaged position.

In an exemplary use, engagement gear (842) is positioned in the initial position of FIG. 66A such that smooth portion (848) of gear (842) faces rack (806). Shaft assembly (802) may be inserted distally through a proximal end of an interface assembly (810) such that rack (806) is laterally aligned with gear (842). Drive shaft (846) is then actuated to rotate gear (842) such that teeth (844) of gear (842) engage teeth (801) rack (806) on shaft assembly (802), as shown in FIG. 66B. Shaft assembly (802) may then be actuated by drive assembly (840) through gear (842). To remove shaft assembly (802), gear (842) is again rotated such that teeth (844) disengage teeth (801), with smooth portion (848) facing shaft assembly (802), as shown in FIG. 66A. Shaft assembly (802) is then pulled proximally out of interface assembly (810). Shaft assembly (802) may then be discarded, while interface assembly (810) may be sterilized and reused in another surgical procedure.

Figure 67:
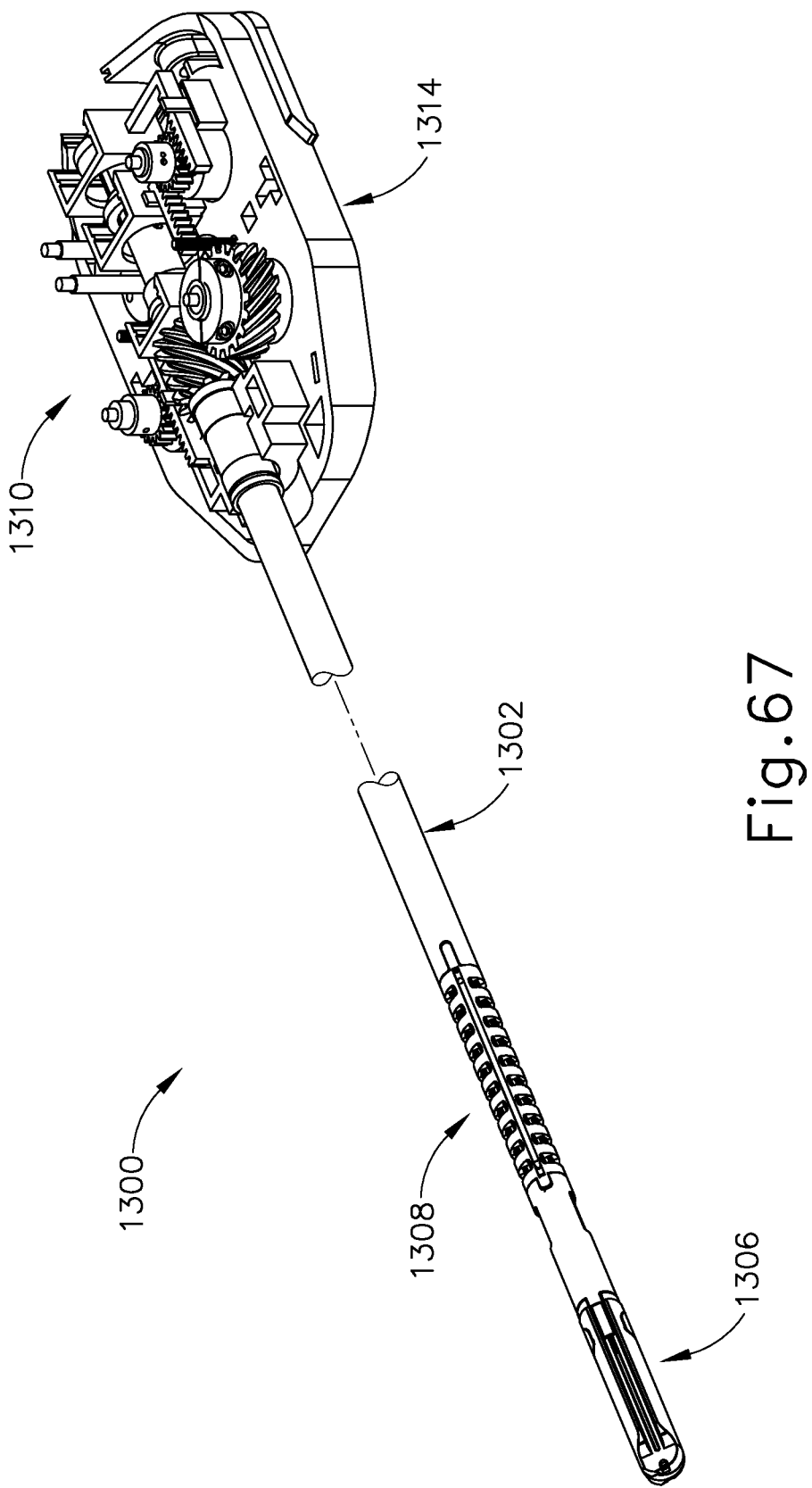
FIG. 67 depicts a partial perspective view of another exemplary surgical instrument suitable for incorporation with the system of FIG. 1.
Figure 68:
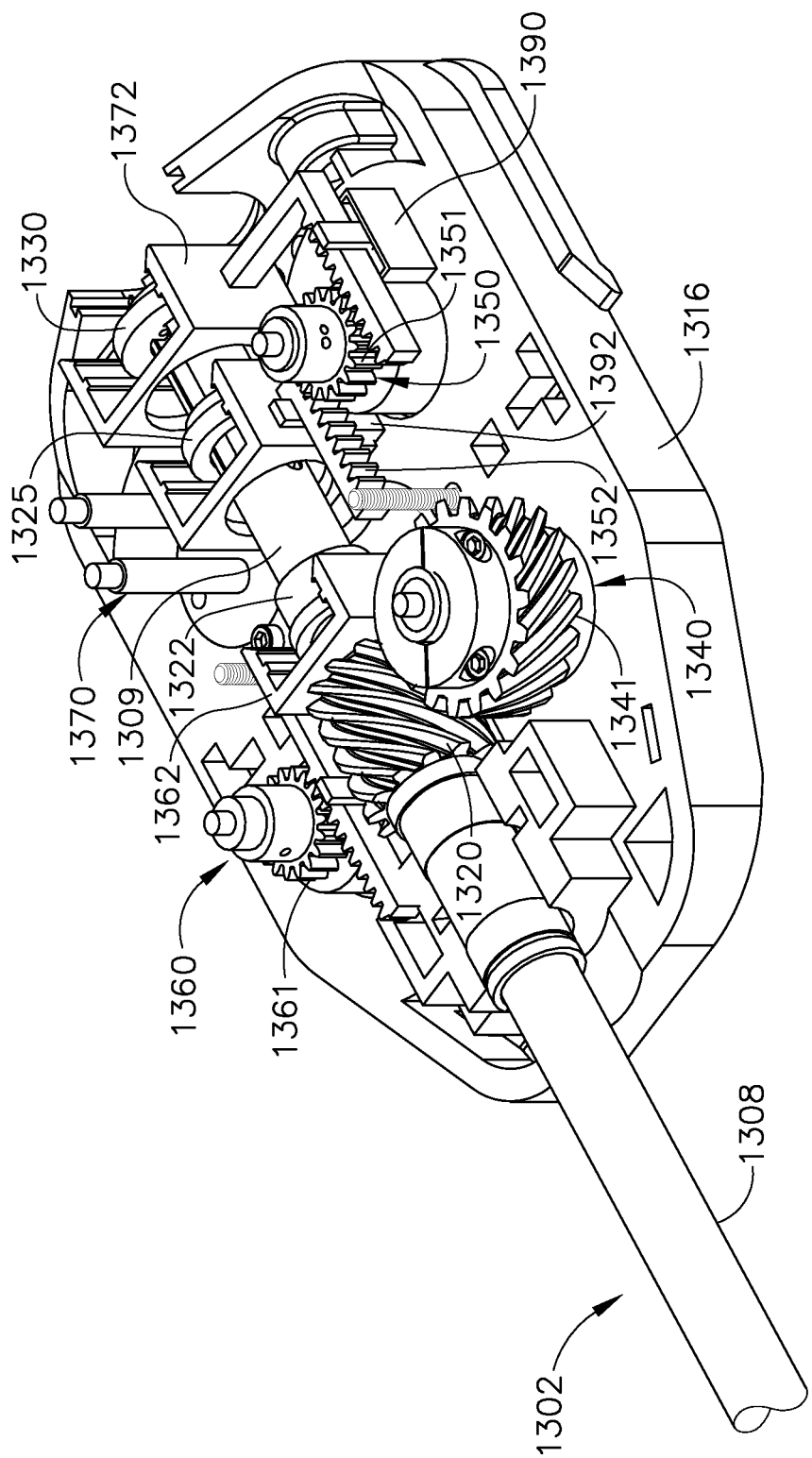
FIG. 68 depicts a partial perspective view of a proximal portion of the shaft assembly and an interface assembly of the instrument of FIG. 67.

IV. Exemplary Alternative Electrosurgical Instrument with a Snap Fit Shaft Assembly In some instances, it may be desirable to couple a shaft assembly and an interface assembly without translating the drive assemblies of the interface assembly. Accordingly, FIGS. 67-68 show an exemplary alternative electrosurgical instrument (1300) with an interface assembly (1310) having snap fit features with shaft assembly (1302) instead of translating drive assemblies. Instrument (1300) of this example is substantially similar to instrument (200) described above in that instrument (1300) has a shaft assembly (1302), an articulation section (1304), and an end effector (1306) that are substantially identical to shaft assembly (202), articulation section (204), and end effector (206) described above. Instrument (1300) of this example is also operable to couple with a dock (72) of robotic arm cart (40) via an interface assembly (1310). Interface assembly (1310) of this example is similar to interface assembly (210), except that interface assembly (1310) comprises features to snap fit with shaft assembly (1302) instead of a translation assembly (280). The examples below include several merely illustrative versions of shaft assembly (1302) features that may be readily introduced to an instrument (200).

Figure 69:
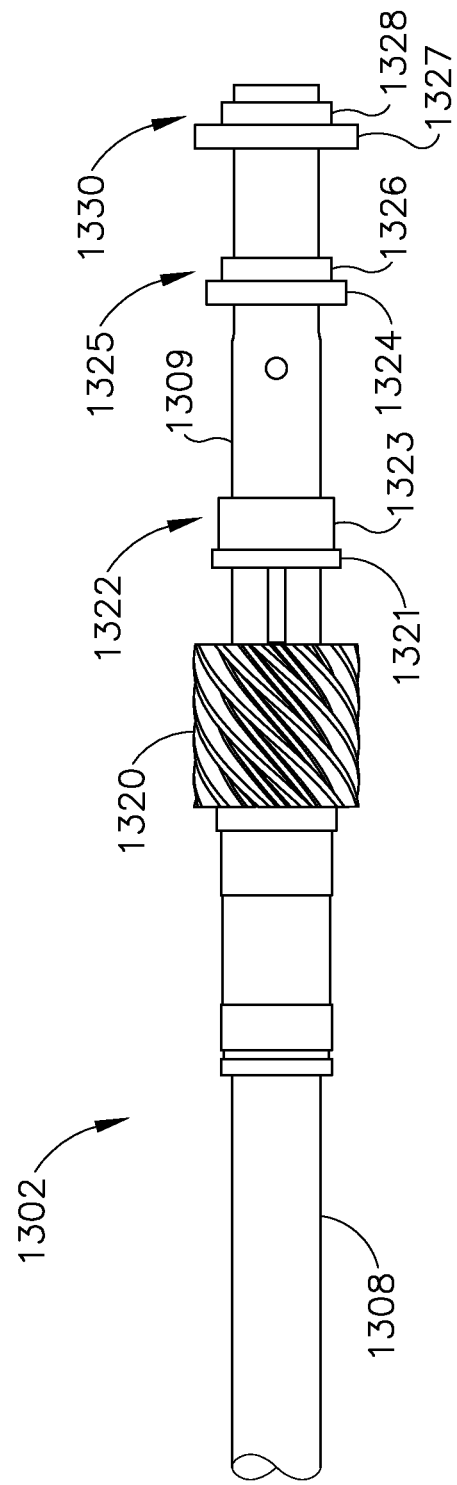
FIG. 69 depicts a partial side elevational view of the shaft assembly of FIG. 68.

Shaft assembly (1302) is similar to shaft assembly (202) and comprises an outer shaft (1308), inner shaft (1309), a helical gear (1320), and collars (1322, 1325, 1330), as shown in FIG. 69. Helical gear (220) is positioned around a proximal portion of outer shaft (208) and is operable to rotate outer shaft (208) relative to interface assembly (210). Collars (1322, 1325, 1330) are positioned around inner shaft (1309). First collar (1322) is proximal to helical gear (1320) and comprises a distal flange (1321) and a proximal portion (1323). Proximal portion (1323) and has a smaller outer diameter than distal flange (1321). First collar (1322) is fixedly secured to a proximal portion of inner shaft (1309) and is thus configured to translate inner shaft (1309) and firing beam (190) relative to outer shaft (1308).

Second collar (1325) is proximal to first collar (1322) and comprises a distal flange (1324) and a proximal portion (1326). Proximal portion (1326) has a smaller outer diameter than distal flange (1324). The outer diameter of distal flange (1324) of second collar (1325) is larger than the outer diameter of distal flange (1321) of first collar (1322). Third collar (1330) is proximal to second collar (1325) and comprises a distal flange (1327) and a proximal portion (1328). Proximal portion (1328) has a smaller outer diameter than distal flange (1327). The outer diameter of distal flange (1327) of third collar (1330) is larger than the outer diameter of distal flange (1324) of second collar (1325). Second and third collars (1325, 1330) are slidably disposed along inner shaft (1309). Second and third collars (1325, 1330) are each fixedly coupled with a respective articulation beam (174, 176) extending within inner shaft (1309) such that translation of second and third collars (1325, 1330) along inner shaft (1309) thereby translates articulation beams (174, 176) relative to inner shaft (1309) and relative to outer shaft (1308).

Figure 70:
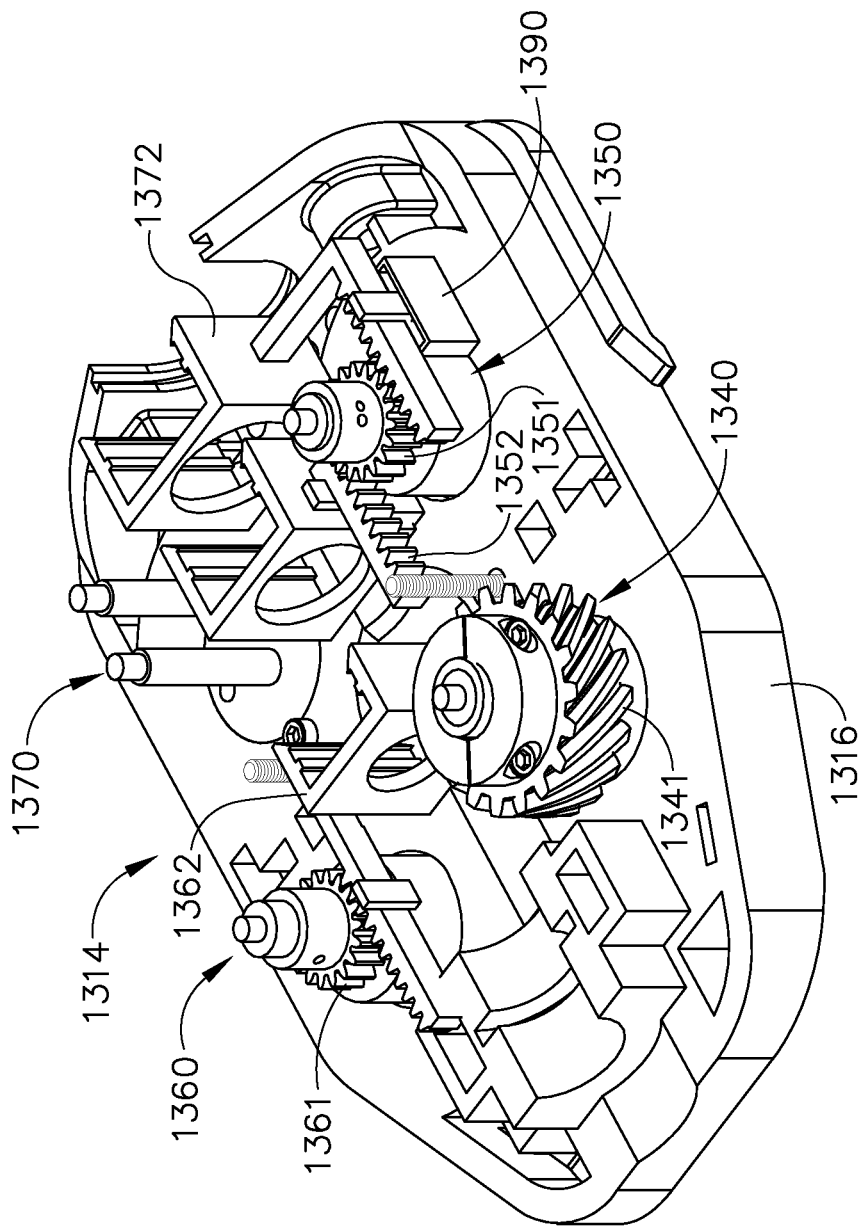
FIG. 70 depicts a perspective view of the interface assembly of FIG. 68.
Figure 71:
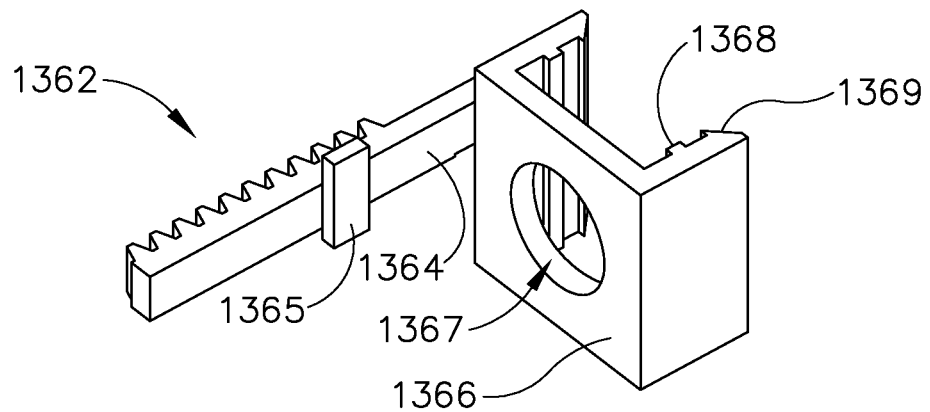
FIG. 71 depicts a perspective view of a first rack of the interface assembly of FIG. 68.
Figure 72:
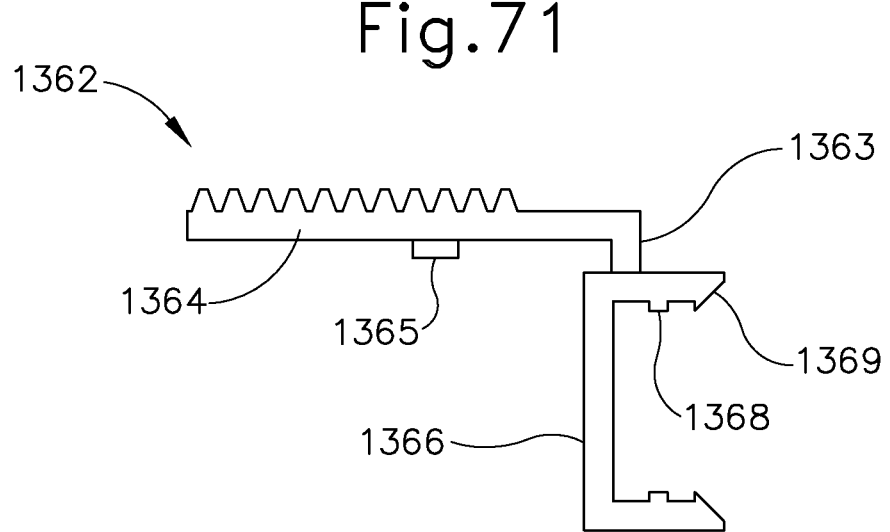
FIG. 72 depicts a top plan view of the first rack of FIG. 71.
Figure 73:
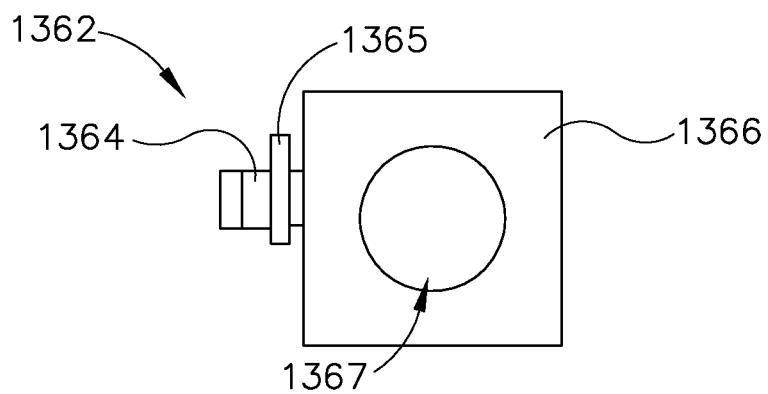
FIG. 73 depicts a front view of the first rack of FIG. 71.

Interface assembly (1310) comprises drive assemblies (1340, 1350, 1360, 1370) similar to drive assemblies (240, 250, 260, 270), as shown in FIG. 70. However, interface assembly (1310) comprises engagement features (1362, 1352, 1372). As shown in FIGS. 71-73, first engagement feature (1362) comprises an arm (1364) with a row of longitudinal teeth to engage gear (1361) of third drive assembly (1360), such that arm (1364) provides a rack. Arm (1364) is connected with arm (1363) extending transversely from arm (1364). Arm (1363) is coupled with bracket (1366). Bracket (1366) comprises walls that extend proximally with protrusions (1368, 1369). Protrusions (1368, 1369) extend inwardly from the walls of bracket (1366) and are configured to engage first collar (1322) of shaft assembly (1302) through a snap fit. In the present example, protrusion (1368) is configured to engage the distal wall of distal flange (1321) of collar (1322). Protrusion (1369) is configured to engage the proximal wall of distal flange (1321) of collar (1322). Protrusions (1368, 1369) thereby engage first collar (1322) to longitudinally fix first collar (1322) relative to engagement feature (1362) such that first collar (1322) translates with engagement feature (1362) when third drive assembly (1360) is actuated. While first collar (1322) translates with engagement feature (1362), engagement feature (1362) allows first collar (1322) to rotate within engagement feature (1362). Engagement feature (1362) comprises an opening (1367) within bracket (1366) to receive shaft assembly (1302) such that shaft assembly (1302) is inserted distally through bracket (1366) such that first collar (1322) engages bracket (1366). First engagement feature (1362) further comprises an alignment feature (1365) extending from arm (1364) of first engagement feature (1362). A channel may be provided on the inner surface of housing (1312) to correspond to alignment feature (1365) such that alignment feature (1365) translates within the channel of housing (1312) as third drive assembly (1360) is actuated to maintain the longitudinal alignment of first engagement feature (1362) relative to shaft assembly (1302).

Figure 74:
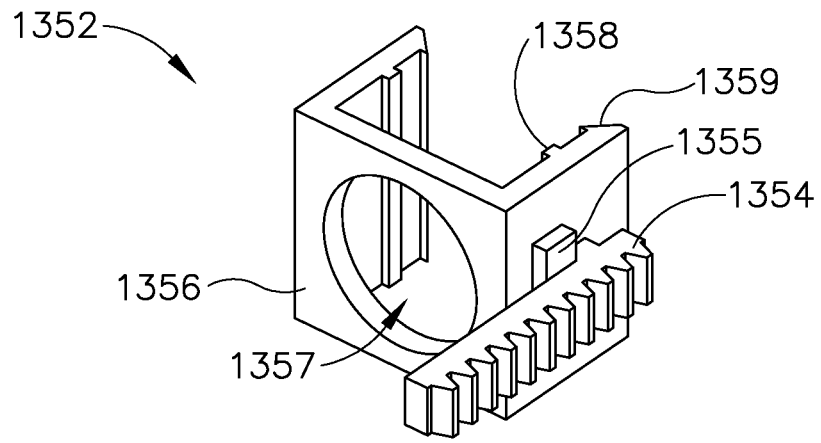
FIG. 74 depicts a perspective view of a second rack of the interface assembly of FIG. 68.
Figure 75:
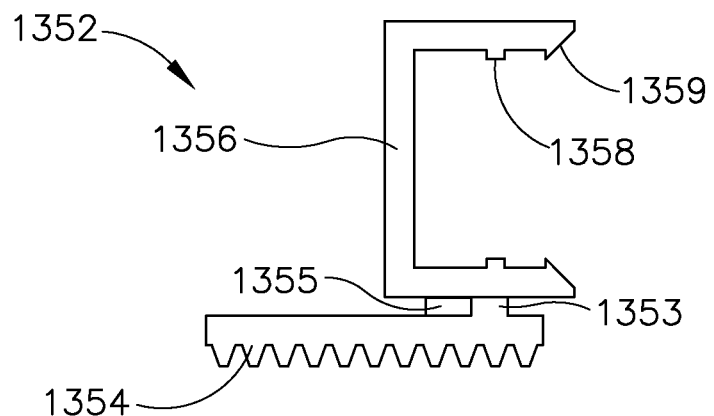
FIG. 75 depicts a top plan view of the second rack of FIG. 74.
Figure 76:
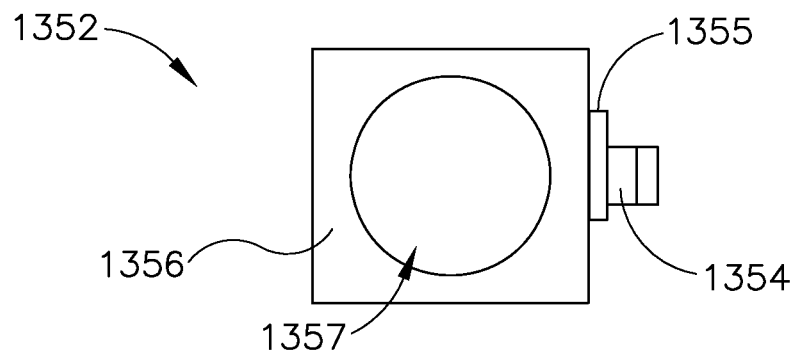
FIG. 76 depicts a front view of the second rack of FIG. 74.

As shown in FIGS. 74-76, second engagement feature (1352) comprises an arm (1354) with a row of longitudinal teeth to engage gear (1351) of second drive assembly (1350), such that arm (1354) provides a rack. Arm (1354) is connected with arm (1353) extending transversely from arm (1354). Arm (1353) is coupled with bracket (1356). Bracket (1356) comprises walls that extend proximally with protrusions (1358, 1359). Protrusions (1358, 1359) extend inwardly from the walls of bracket (1356) and are configured to engage second collar (1325) of shaft assembly (1302) through a snap fit. In the present example, protrusion (1358) is configured to engage the distal wall of distal flange (1324) of collar (1325). Protrusion (1359) is configured to engage the proximal wall of distal flange (1324) of collar (1325). Protrusions (1358, 1359) thereby engage second collar (1325) to longitudinally fix second collar (1325) relative to engagement feature (1352) such that second collar (1325) translates with engagement feature (1352) when second drive assembly (1350) is actuated. While second collar (1325) translates with engagement feature (1352), engagement feature (1352) allows second collar (1325) to rotate within engagement feature (1352). Engagement feature (1352) comprises an opening (1357) within bracket (1356) to receive shaft assembly (1302) such that shaft assembly (1302) is inserted distally through bracket (1356) such that second collar (1325) engages bracket (1356). Opening (1357) is sized to be larger than distal flange (1321) of first collar (1322) to allow first collar (1322) to pass through second engagement feature (1352). Second engagement feature (1352) further comprises an alignment feature (1355) extending from arm (1354) of second engagement feature (1352). A channel (1392) is provided on the top surface of mounting plate (1316) to correspond to alignment feature (1355) such that alignment feature (1355) translates within channel (1392) of mounting plate (1316) as second drive assembly (1350) is actuated to maintain the longitudinal alignment of second engagement feature (1352) relative to shaft assembly (1302).

Figure 77:
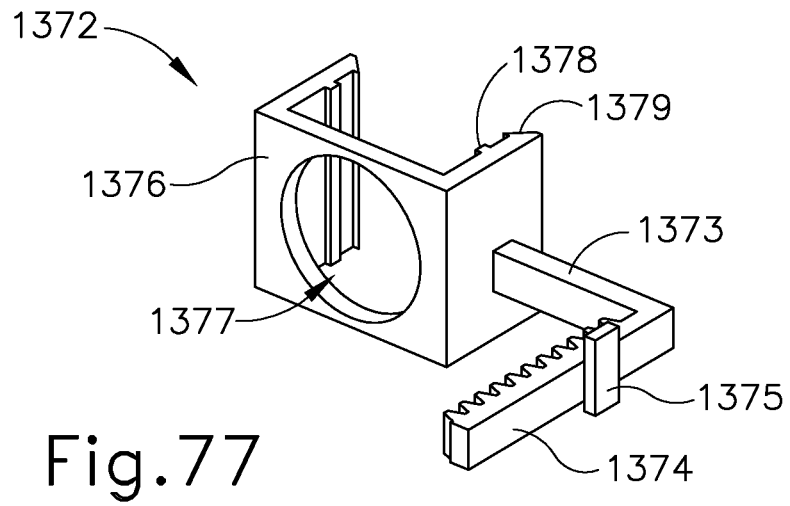
FIG. 77 depicts a perspective view of a third rack of the interface assembly of FIG. 68.
Figure 78:
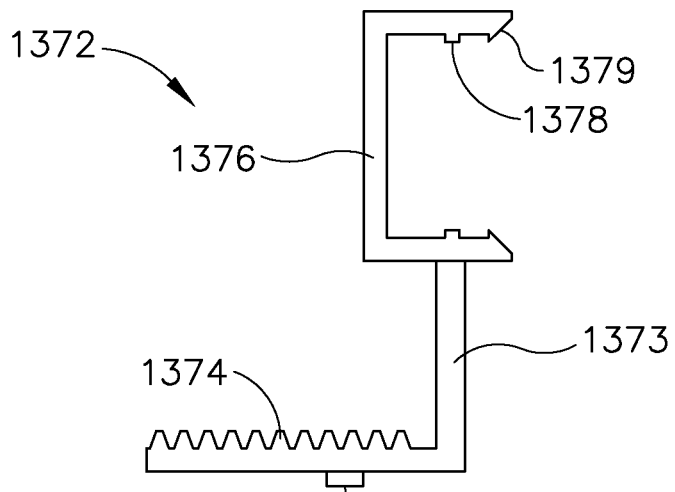
FIG. 78 depicts a top plan view of the third rack of FIG. 77.
Figure 79:
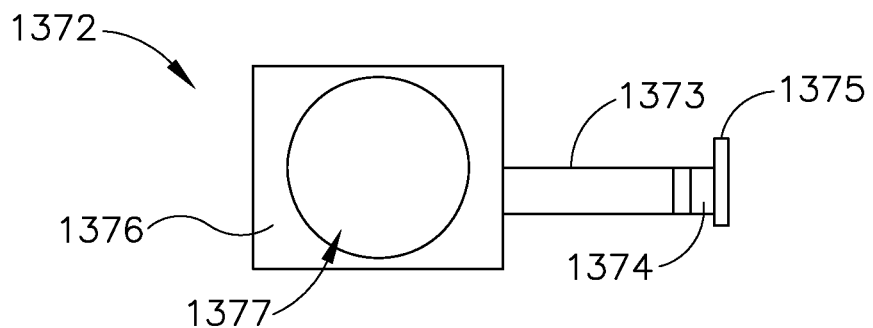
FIG. 79 depicts a front view of the third rack of FIG. 77.

As shown in FIGS. 77-79, third engagement feature (1372) comprises an arm (1374) with a row of longitudinal teeth to engage gear (1351) of second drive assembly (1350), such that arm (1374) provides a rack. Arm (1374) is positioned on the opposing side of gear (1351) from arm (1354) of second engagement feature (1352) such that engagement features (1352, 1372) translate in opposing directions when gear (1351) is rotated by drive shaft (1356). Arm (1374) is connected with arm (1373) extending transversely from arm (1374). Arm (1373) is coupled with bracket (1376). Bracket (1376) comprises walls that extend proximally with protrusions (1378, 1379). Protrusions (1378, 1379) extend inwardly from the walls of bracket (1376) and are configured to engage third collar (1330) of shaft assembly (1302) through a snap fit. In the present example, protrusion (1378) is configured to engage the distal wall of distal flange (1327) of collar (1330). Protrusion (1379) is configured to engage the proximal wall of distal flange (1327) of collar (1330). Protrusions (1378, 1379) thereby engage third collar (1330) to longitudinally fix third collar (1330) relative to engagement feature (1372) such that third collar (1330) translates with engagement feature (1372) when second drive assembly (1350) is actuated. While third collar (1330) translates with engagement feature (1372), engagement feature (1372) allows third collar (1330) to rotate within engagement feature (1372). Engagement feature (1372) comprises an opening (1377) within bracket (1376) to receive shaft assembly (1302) such that shaft assembly (1302) is inserted distally through bracket (1376) such that third collar (1330) engages bracket (1376). Opening (1377) is sized to be larger than distal flange (1321) of first collar (1322) and distal flange (1324) of second collar (1325) to allow first collar (1322) and second collar (1325) to pass through third engagement feature (1372). Third engagement feature (1372) further comprises an alignment feature (1375) extending from arm (1374) of third engagement feature (1372). A channel (1390) is provided on the top surface of mounting plate (1316) to correspond to alignment feature (1375) such that alignment feature (1375) translates within channel (1390) of mounting plate (1316) as second drive assembly (1350) is actuated to maintain the longitudinal alignment of third engagement feature (1372) relative to shaft assembly (1302).

A. Exemplary Assembly of a Snap Fit Shaft Assembly

Figure 80A:
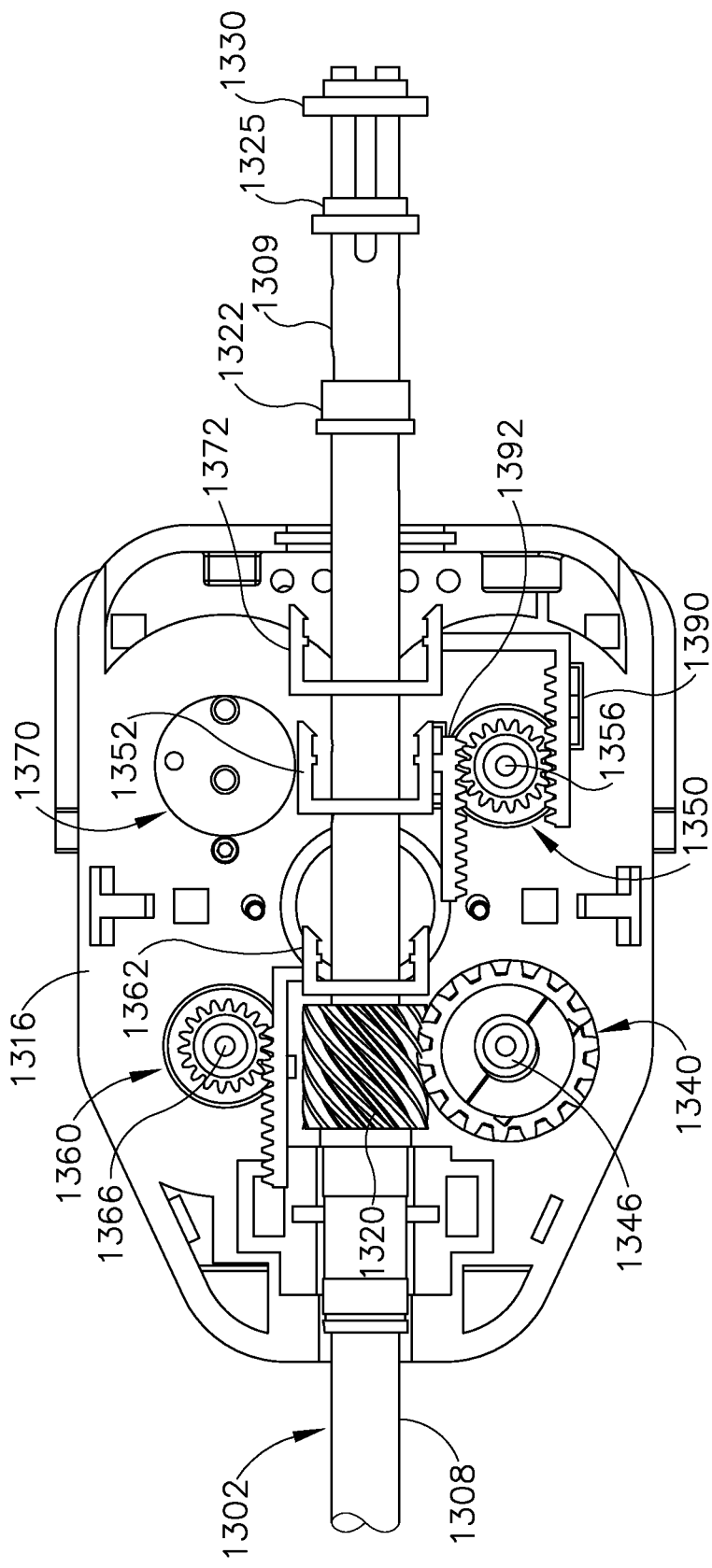
FIG. 80A depicts a top plan view of the interface assembly of FIG. 68, showing the shaft assembly being inserted within the interface assembly.
Figure 80B:
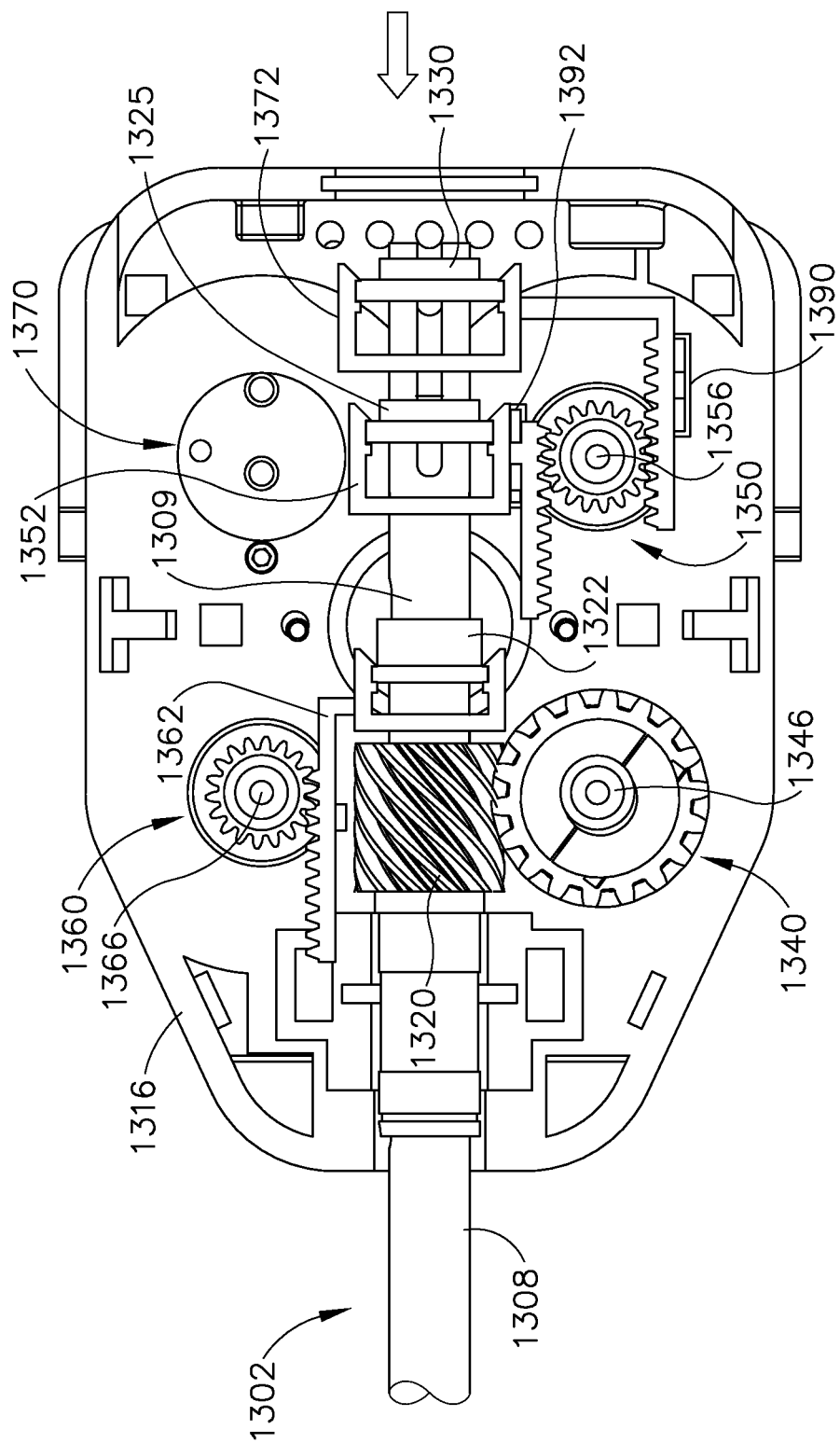
FIG. 80B depicts a top plan view of the interface assembly of FIG. 68, showing the shaft assembly coupled with the interface assembly.

In an exemplary use, shaft assembly (1302) is inserted distally through a proximal end of interface assembly (1310), as shown in FIG. 80A. Shaft assembly (1302) is inserted within interface assembly (1310) until first collar (1322) engages first engagement feature (1362), second collar (1325) engages second engagement feature (1352), and third collar (1330) engages third engagement feature (1372), as shown in FIG. 80B. The proximal edges of engagement features (1362, 1352, 1372) are ramped to cammingly engage collars (1322, 1325, 1330) as collars (1322, 1325, 1330) enter engagement features (1362, 1352, 1372). The walls of engagement features (1362, 1352, 1372) flex slightly outwardly as collars (1322, 1325, 1330) slide into engagement features (1362, 1352, 1372). Engagement features (1362, 1352, 1372) thus snap around collars (1322, 1325, 1330) to maintain the longitudinal alignment of shaft assembly (1302).

After engagement features (1362, 1352, 1362) engage shaft assembly (1302), instrument (1300) may be operated. Arm cart (40) is used to insert end effector (1306) into a patient via a trocar. Articulation section (1304) is substantially straight when end effector (1306) and part of shaft assembly (1302) are inserted through the trocar. Drive shaft (1366) may be actuated to retract firing beam (190) to thereby open jaws (182, 184). Drive shaft (1346) may be rotated through drive features in dock (72) to position end effector (1306) at a desired angular orientation relative to the tissue. Drive shaft (1356) may then be rotated through drive features in dock (72) to pivot or flex articulation section (1304) of shaft assembly (1302) in order to position end effector (1306) at a desired position and orientation relative to an anatomical structure within the patient. Of course drive shaft (1346) and/or drive shaft (1356) may be actuated prior to opening jaws (182, 184). Two layers of tissue of the anatomical structure are then captured between jaws (182, 184) by rotating drive shaft (1366) to advance firing beam (190) distally through a first range of motion. As noted above, flanges (192, 196) cammingly act to pivot jaw (182) toward jaw (184) when firing beam (190) is actuated distally by rotating drive shaft (1366).

With tissue layers captured between jaws (182, 184) firing beam (190) continues to advance distally in response to continued rotation of drive shaft (1366). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (1366) may then be actuated in the opposing direction to retract firing beam (190) and open jaws (182, 184) of end effector (1306) to release the tissue. Articulation section (1304) may be again aligned with shaft assembly (1302) by actuating drive shaft (1356) and jaws (182, 184) may be again re-closed by actuating drive shaft (1366). End effector (1306) may then be removed from the patient.

B. Exemplary Disassembly of a Snap Fit Shaft Assembly

Figure 81:
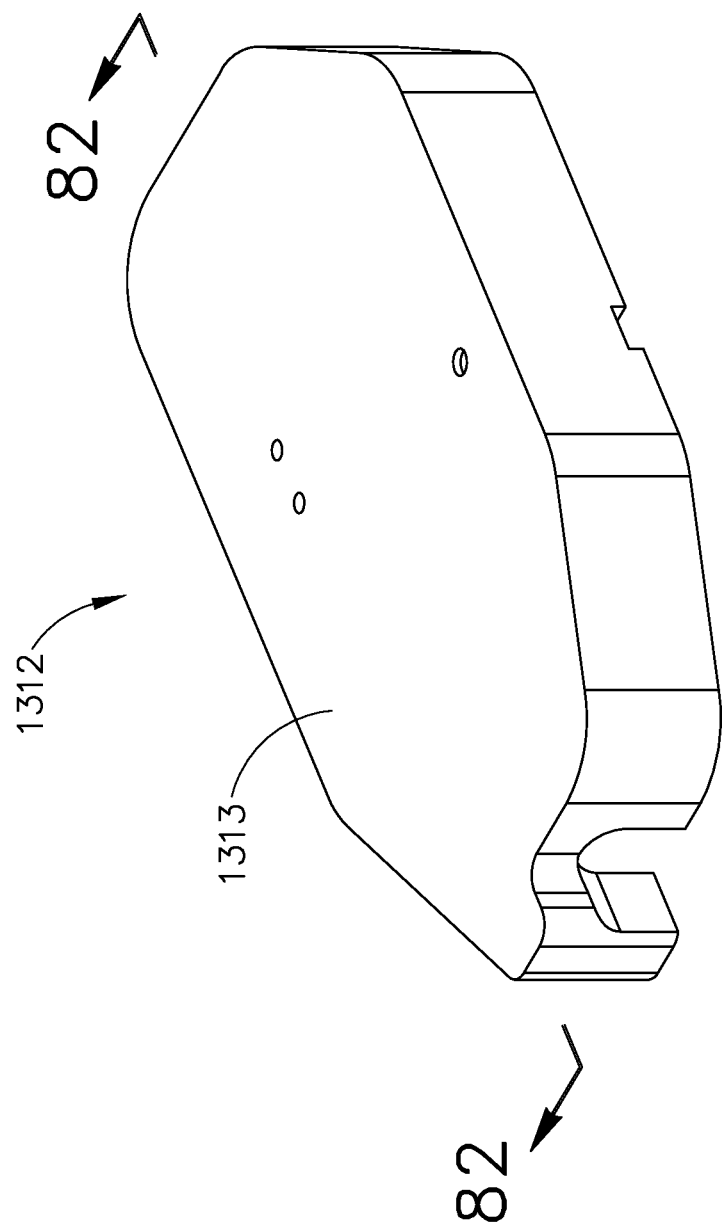
FIG. 81 depicts a perspective view of a cover for use with the interface assembly of FIG. 68.
Figure 82:
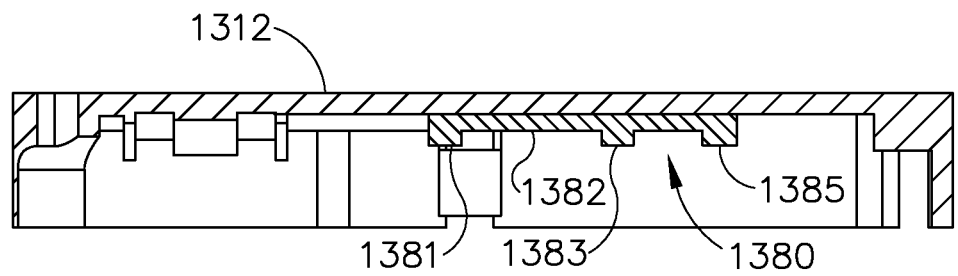
FIG. 82 depicts a cross sectional view of the cover of FIG. 81 taken along the line 82-82 of FIG. 81, showing a locking assembly.
Figure 83:
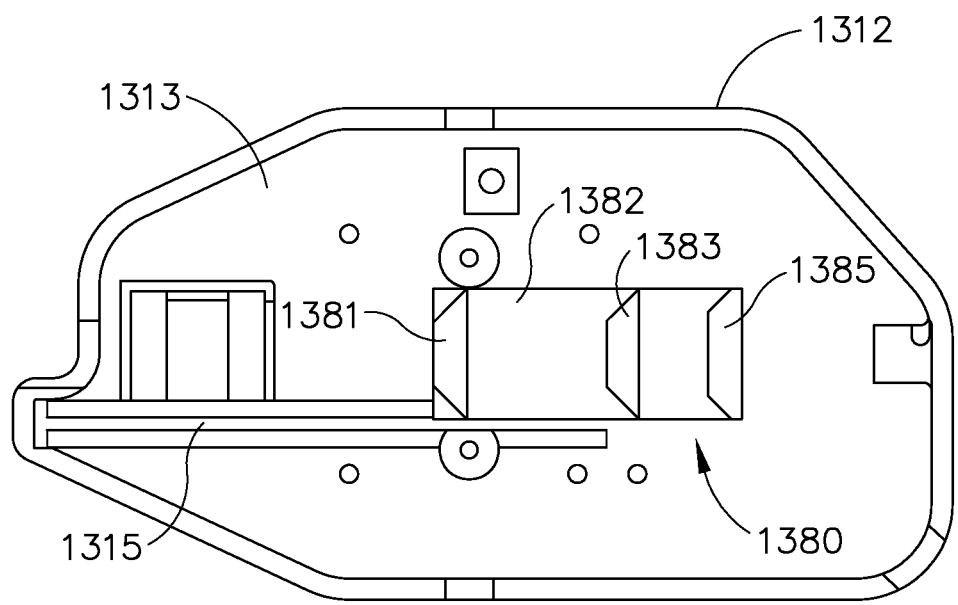
FIG. 83 depicts a bottom plan view of the cover of FIG. 81, showing the locking assembly.

Housing (1312) of interface assembly (1310) comprises exemplary removal features to disengage shaft assembly (1302) from interface assembly (1310). FIGS. 81-83 show housing (1312) with a shaft removal assembly (1380) coupled to the interior of top surface (1313) of housing (1312). Shaft removal assembly (1380) comprises a plate (1382) and wedges (1381, 1383, 1385). Wedges (1381, 1383, 1385) extend downwardly from plate (1382) within housing (1312). Each wedge (1381, 1383, 1385) has a substantially trapezoidal shape such that the proximal wall of each wedge (1381, 1383, 1385) is wider than the distal wall of each edge (1381, 1383, 1385). The side walls of each wedge (1381, 1383, 1385) then ramp between the proximal wall and distal wall of each wedge (1381, 1383, 1385). Wedges (1381, 1383, 1385) are positioned on plate (1382) such that wedges (1381, 1383, 1385) are configured to engage engagement features (1362, 1352, 1372). For instance, wedge (1381) is configured to engage the proximally extending walls of engagement feature (1362) to flex the walls outwardly to release first collar (1322). Wedge (1383) is configured to engage the proximally extending walls of engagement feature (1352) to flex the walls outwardly to release second collar (1325). Wedge (1385) is configured to engage the proximally extending walls of engagement feature (1372) to flex the walls outwardly to release third collar (1330). Plate (1382) is translatable within housing (1312) to simultaneously actuate wedges (1381, 1383, 1385).

Figure 84A:
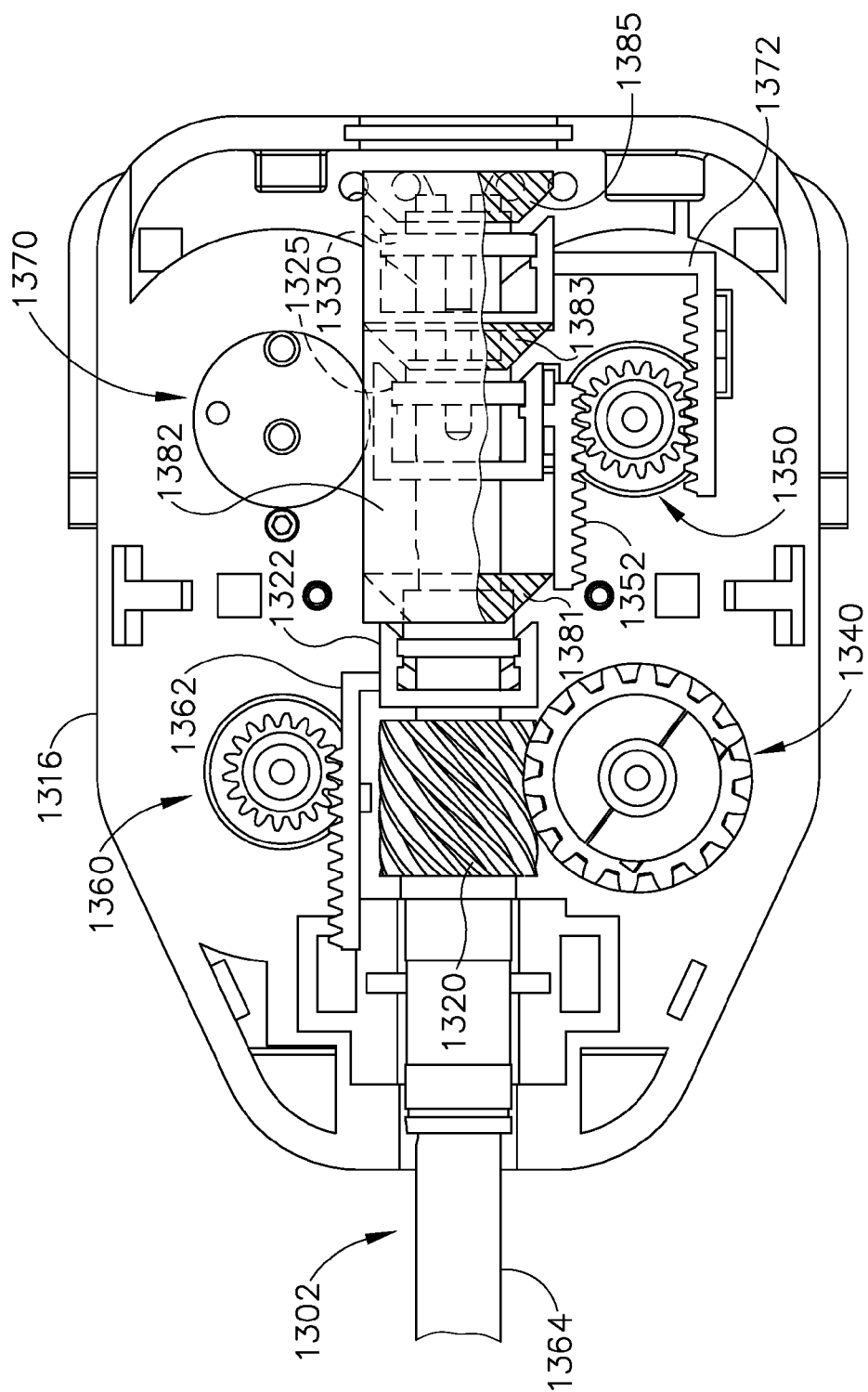
FIG. 84A depicts a top plan view of the interface assembly of FIG. 68, showing the locking assembly of FIG. 82 in a disengaged position with the shaft assembly, with the cover removed.
Figure 84B:
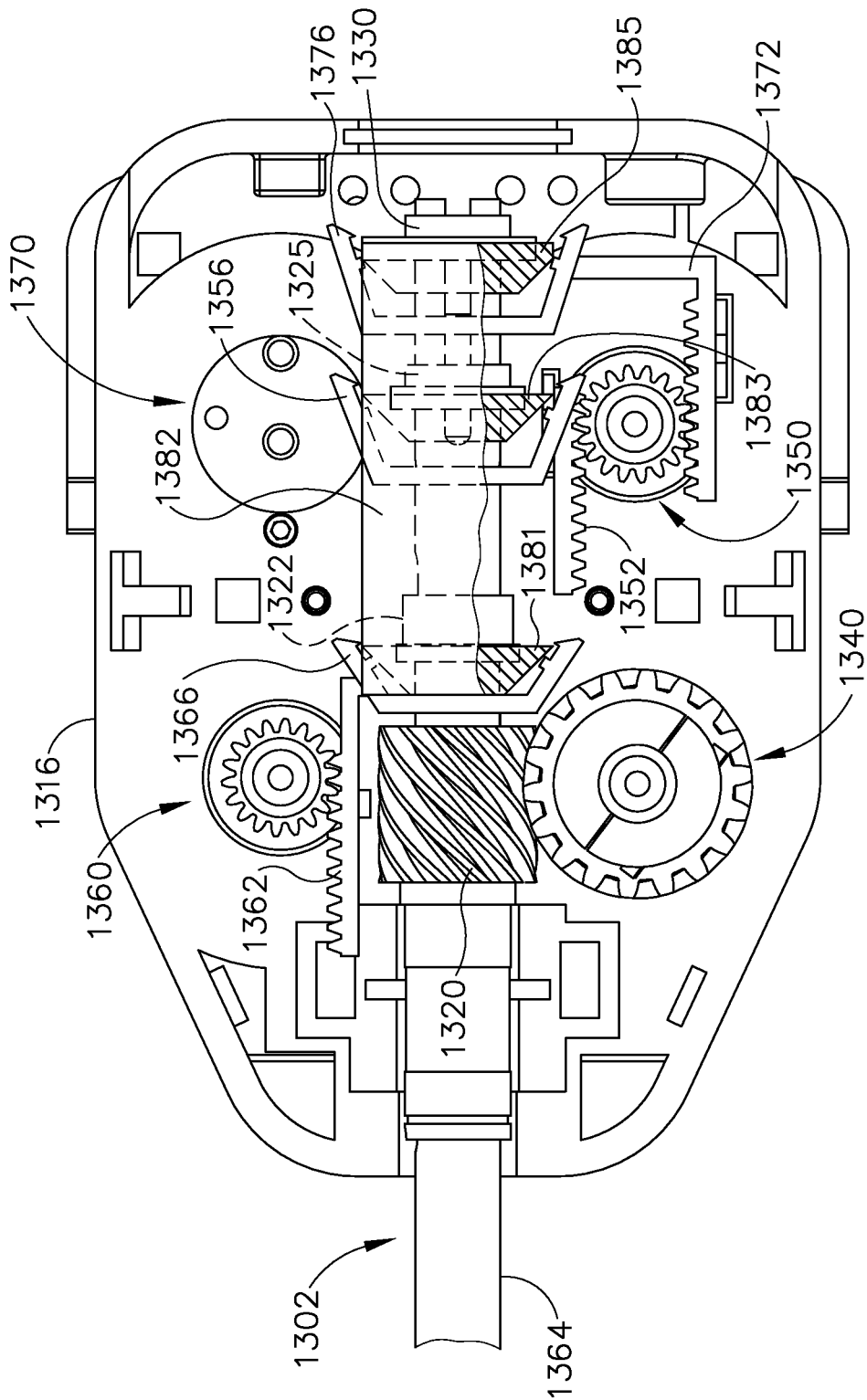
FIG. 84B depicts a top plan view of the interface assembly of FIG. 68, showing the locking assembly of FIG. 82 in an engaged position with the shaft assembly, with the cover removed.

FIGS. 84A-84B show shaft removal assembly (1380) engaging engagement features (1362, 1352, 1372) to release shaft assembly (1302) to allow shaft assembly (1302) to be removed from interface assembly (1310). FIG. 84A shows shaft removal assembly (1380) in a first position such that shaft removal assembly (1380) is disengaged from engagement features (1362, 1352, 1372). In the present example, shaft removal assembly (1380) is positioned adjacent to top surface (1313) of housing (1380) such that wedges (1381, 1383, 1385) are disengaged from engagement features (1362, 1352, 1372) and allow interface assembly (1310) to freely operate. Plate (1382) is positioned to align wedges (1381, 1383, 1385) proximal to engagement features (1362, 1352, 1372). Plate (1382) of shaft removal assembly (1380) is then actuated to pivot downwardly and distally within interface assembly (1310), as shown in FIG. 84B. Plate (1382) is actuated to thereby pivot wedges (1381, 1383, 1385) downwardly and distally within interface assembly (1310). Shaft removal assembly (1380) may be actuated by a lever, linkage, rotation knob, button, or other suitable actuator coupled with interface assembly (1310) that will be apparent to one with ordinary skill in the art in view of the teachings herein. Accordingly, wedge (1381) engages the proximally extending walls of engagement feature (1362) to flex the walls outwardly to release first collar (1322), wedge (1383) engages the proximally extending walls of engagement feature (1352) to flex the walls outwardly to release second collar (1325), and wedge (1385) engages the proximally extending walls of engagement feature (1372) to flex the walls outwardly to release third collar (1330). Shaft assembly (1302) may then freely translate relative to interface assembly (1310) and may be removed by pulling shaft assembly (1302) proximally from interface assembly (1310). Shaft assembly (1302) may then be discarded, while interface assembly (1310) may be sterilized and reused in another surgical procedure. Of course, various other suitable ways in which instrument (1300) may be used will be apparent to those of ordinary skill in the art in view of the teachings herein.

C. Alternative Translating Shaft Engagement Assembly

Figure 85:
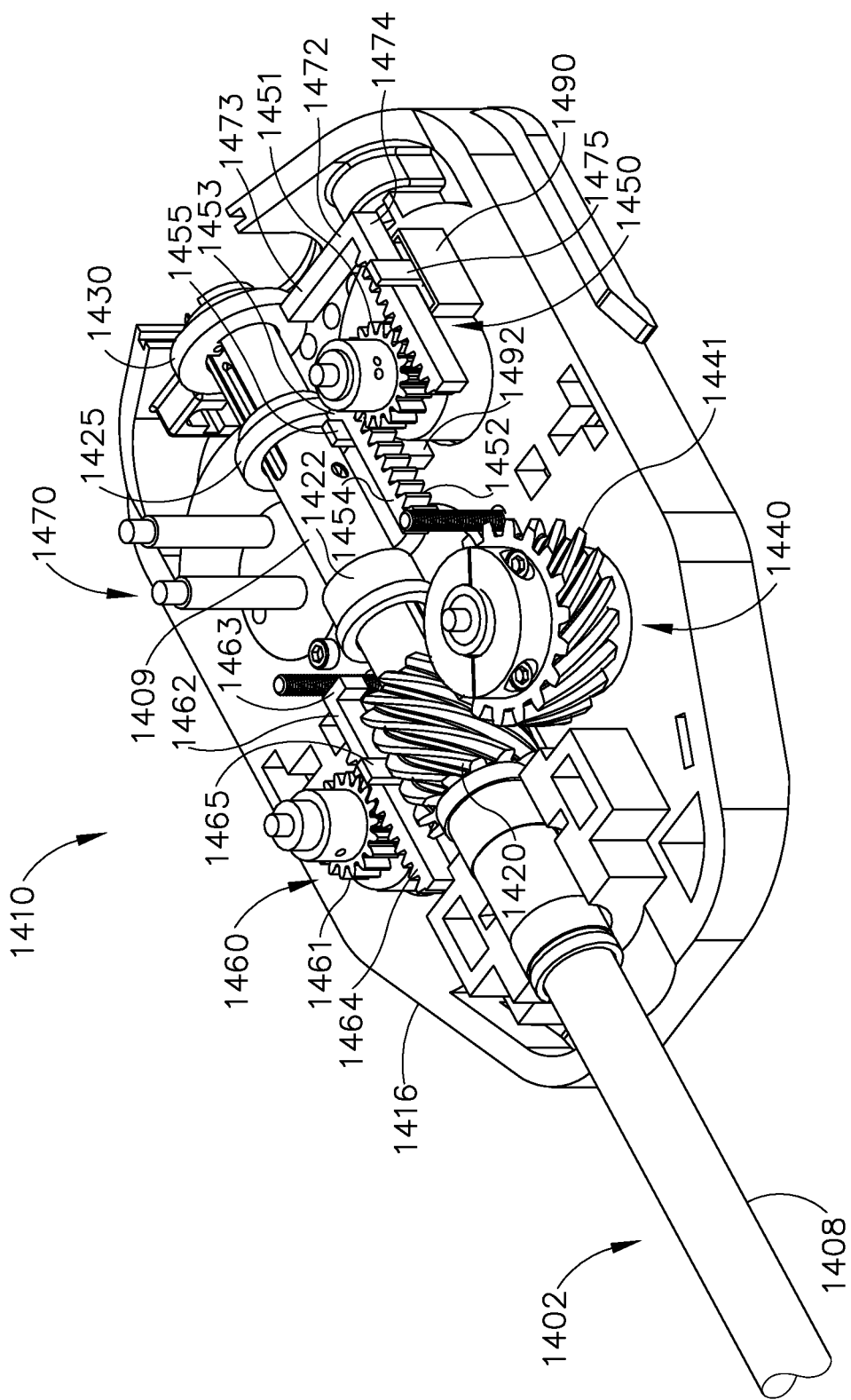
FIG. 85 depicts a partial perspective view of another interface assembly for use with the instrument of FIG. 67.

FIG. 85 shows another exemplary interface assembly (1410) with a translating shaft engagement assembly to selectively engage and/or disengage shaft assembly (1402) without translating drive assemblies (1440, 1450, 1460, 1470). Shaft assembly (1402) is substantially similar to shaft assembly (1302). Interface assembly (1410) is similar to interface assembly (1310), except that engagement features (1462, 1452, 1472) lack brackets (1366, 1356, 1376). Accordingly, engagement features (1462, 1452, 1472) end with arms (1463, 1453, 1473) extending inwardly toward shaft assembly (1402), but arms (1463, 1453, 1473) do not directly engage shaft assembly (1402). Instead, locking collars (1480) are selectively coupled with interface assembly (1410) to engage shaft assembly (1402).

Figure 86:
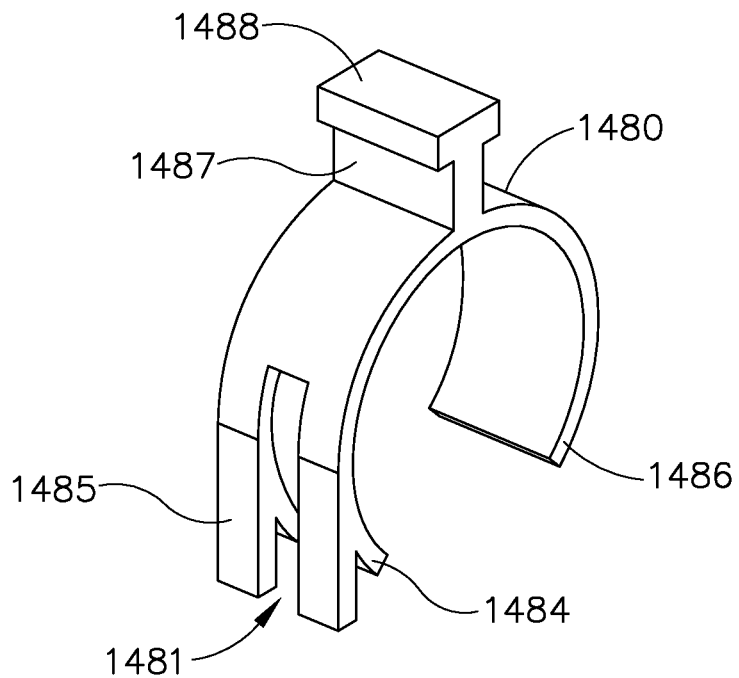
FIG. 86 depicts a perspective view of an exemplary locking collar for use with the interface assembly of FIG. 85.
Figure 87:
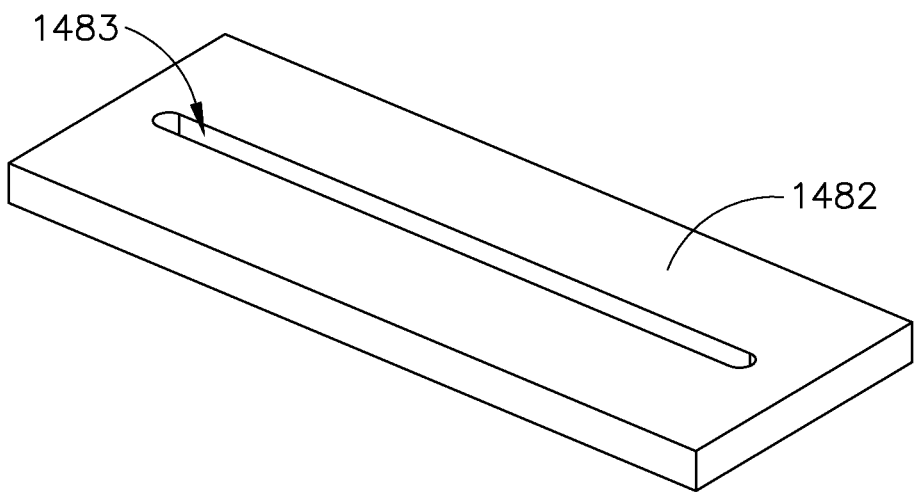
FIG. 87 depicts a perspective view of an exemplary locking plate for use with the interface assembly of FIG. 85.

FIG. 86 shows locking collar (1480) in greater detail. Locking collar (1480) comprises a bracket (1484) having a curved profile and an opening (1486) configured to correspond to collars (1422, 1425, 1430) of shaft assembly (1402). The ends of bracket (1484) are ramped to cammingly engage a corresponding collar (1422, 1425, 1430) when a collar (1422, 1425, 1430) is inserted within opening (1486). Bracket (1484) is configured to flex slightly as a collar (1422, 1425, 1430) is inserted within opening (1486). Locking collar (1480) further comprises an arm (1485) extending adjacent to bracket (1484). Arm (1485) includes a channel (1481) extending within arm (1485). Channel (1481) is sized to receive an arm (1463, 1453, 1473) of a corresponding engagement feature (1462, 1452, 1472). A tab (1488) is positioned on a top surface of locking collar (1480) and is coupled to bracket (1484) of locking collar (1480) via post (1487). Locking collar (1480) is couplable with a plate (1482), shown in FIG. 87. Plate (1482) comprises a channel (1483) extending within plate (1482). Post (1487) of locking collar (1480) is positioned through channel (1483) of plate (1482) such that bracket (1484) of locking collar (1480) is positioned below plate (1482) and tab (1488) of locking collar (1480) is positioned above plate (1482) to hold locking collar (1480) within plate (1482). Locking collar (1480) is translatable within channel (1483) of plate (1482).

Figure 88A:
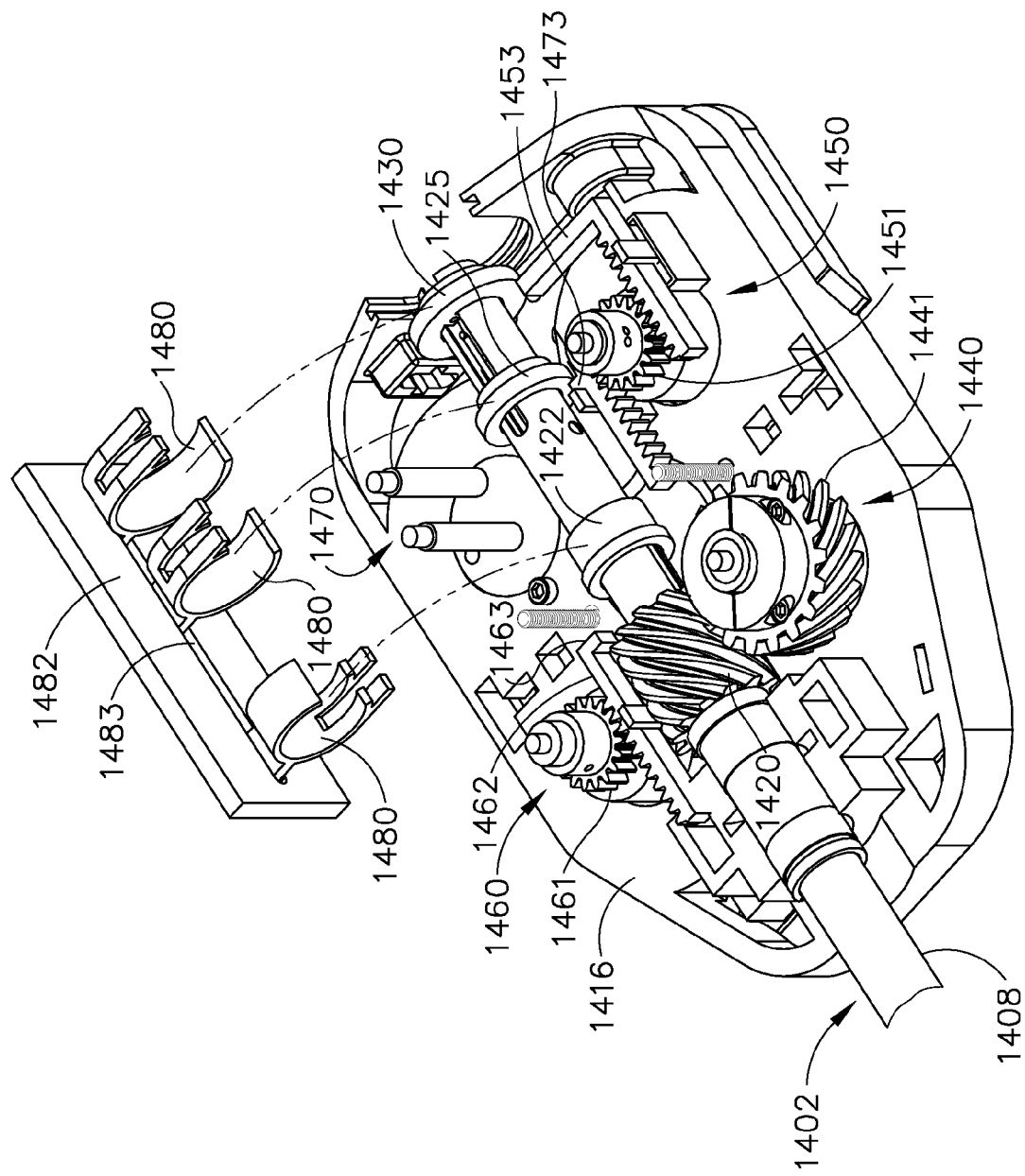
FIG. 88A depicts a perspective view of the interface assembly of FIG. 67, showing the locking assembly in an unlocked position.
Figure 88B:
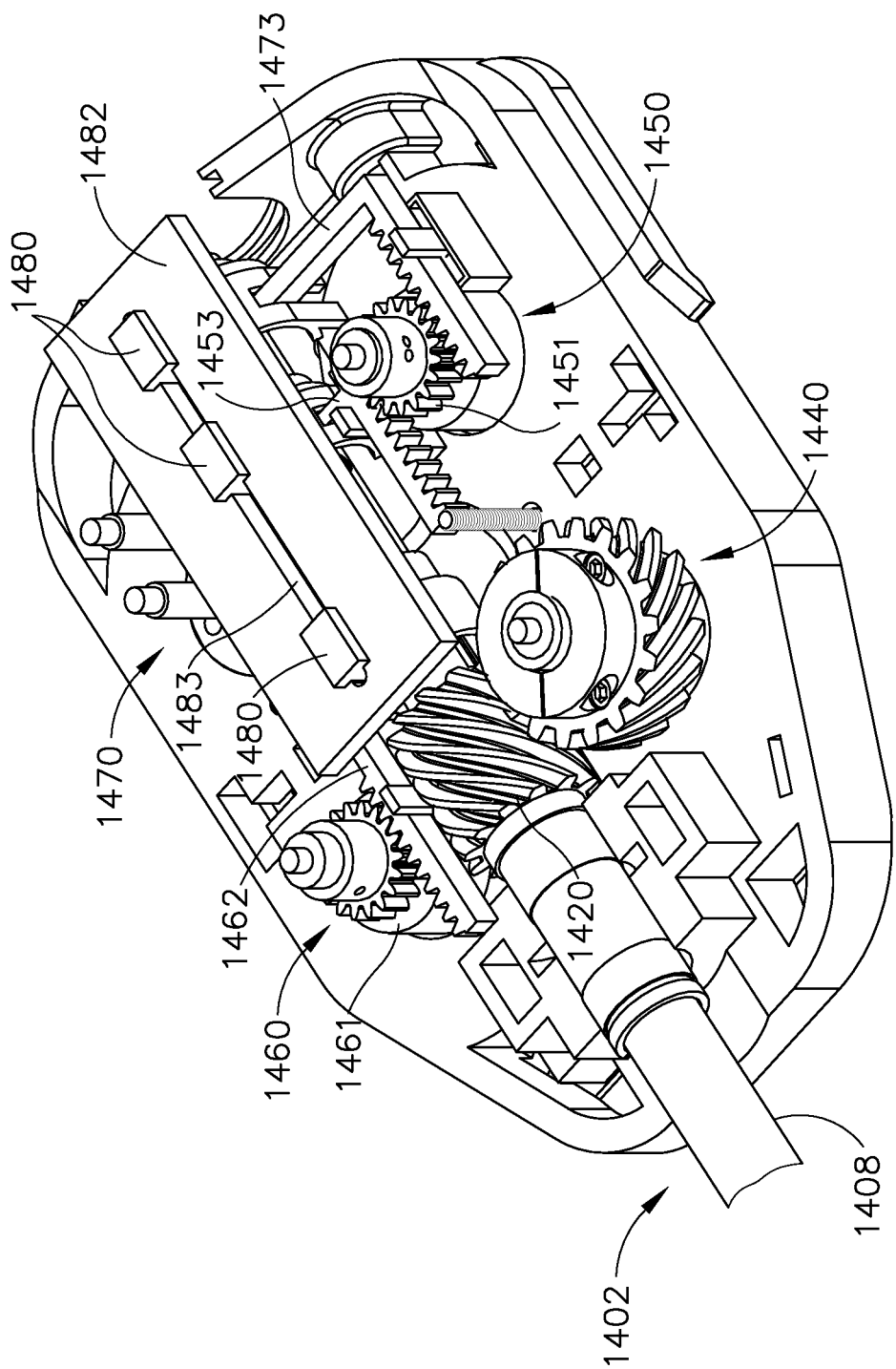
FIG. 88B depicts a perspective view of the interface assembly of FIG. 67, showing the locking assembly in a locked position.

In the present example, three locking collars (1480) are coupled to plate (1482), as shown in FIG. 88A. However, any other suitable number of locking collars (1480) may be used. Plate (1482) is positioned above shaft assembly (1402) such that locking collars (1480) are disengaged with shaft assembly (1402). Shaft assembly (1402) may thus translate freely within interface assembly (1410). Accordingly, shaft assembly (1402) may be inserted distally through the proximal end of interface assembly (1410). Plate (1482) is then actuated to translate downwardly within interface assembly (1410), as shown in FIG. 88B. As plate (1482) translates downwardly, a bracket (1484) of a locking collar (1480) snaps onto first collar (1422) to wrap around at least a portion of first collar (1422), and an arm (1485) receives arm (1463) of first engagement feature (1462). Another bracket (1484) of a second locking collar (1480) snaps onto second collar (1425) to wrap around at least a portion of second collar (1425), and an arm (1485) receives arm (1453) of second engagement feature (1452). A third bracket (1484) of a third locking collar (1480) snaps onto third collar (1430) to wrap around at least a portion of third collar (1430), and an arm (1485) receives arm (1473) of third engagement feature (1472). Plate (1482) is actuated to thereby translate locking collars (1480) simultaneously downwardly within interface assembly (1410). Plate (1482) may be coupled with a housing (not shown) of interface assembly (1410) and may be actuated by a lever, linkage, rotation knob, button, or other suitable actuator coupled with interface assembly (1410) that will be apparent to one with ordinary skill in the art in view of the teachings herein.

When locking collars (1480) are engaged with shaft assembly (1402), locking collars (1480) maintain the longitudinal alignment of shaft assembly (1402) within interface assembly (1410) while allowing shaft assembly (1402) to rotate within interface assembly (1410). Interface assembly (1410) may then be actuated to operate shaft assembly (1410). As collars (1422, 1425, 1430) are actuated to operate shaft assembly (1402), locking collars (1480) translate with collars (1422, 1425, 1430) within channel (1483) of plate (1482). Once shaft assembly (1402) is ready to be removed from interface assembly (1410), plate (1482) is actuated to translate locking collars (1480) upwardly to disengage collars (1422, 1425, 1430), as shown in FIG. 88A. Shaft assembly (1402) may then freely translate relative to interface assembly (1410) and may be removed by pulling shaft assembly (1402) proximally from interface assembly (1410). Shaft assembly (1402) may then be discarded, while interface assembly (1410) may be sterilized and reused in another surgical procedure.

Figure 89:
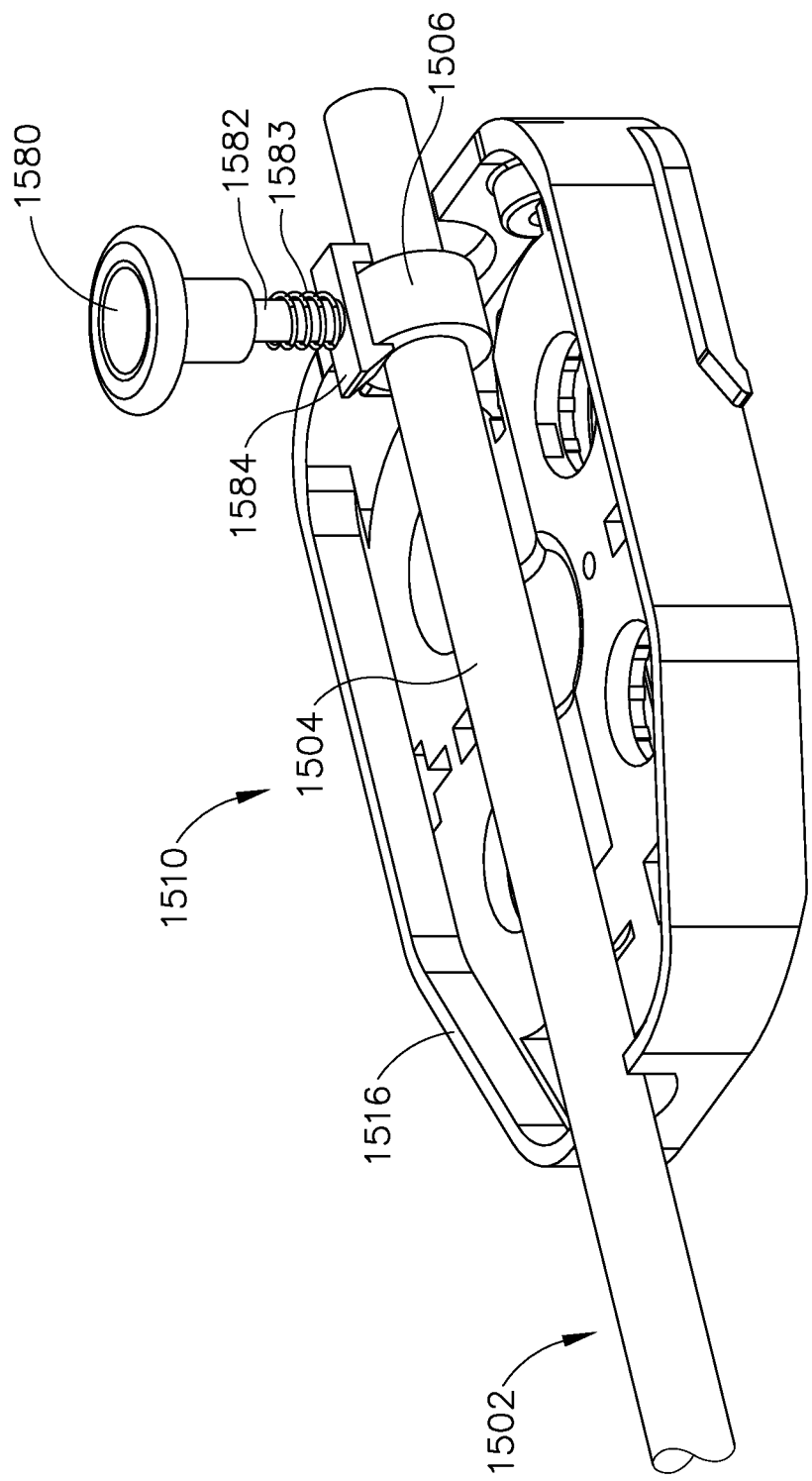
FIG. 89 depicts a partial perspective view of a locking assembly for use with the interface assembly of FIG. 85.

In some instances, it may be desirable to independently engage each collar (1422, 1425, 1430) of shaft assembly (1402). Accordingly, a spring assembly (1580) may be provided to engage each collar (1506) of a shaft assembly (1502), as shown in FIG. 89. Spring assembly (1580) comprises an actuator (1582) coupled with a bracket (1584) via a pin (1586). Bracket (1584) comprises walls extending downwardly to engage each side of a collar (1506) of a shaft assembly (1502) to maintain the longitudinal alignment of shaft assembly (1502). A resilient member (1583) is provided on pin (1586) to bias bracket (1584) downwardly.

Figure 90A:
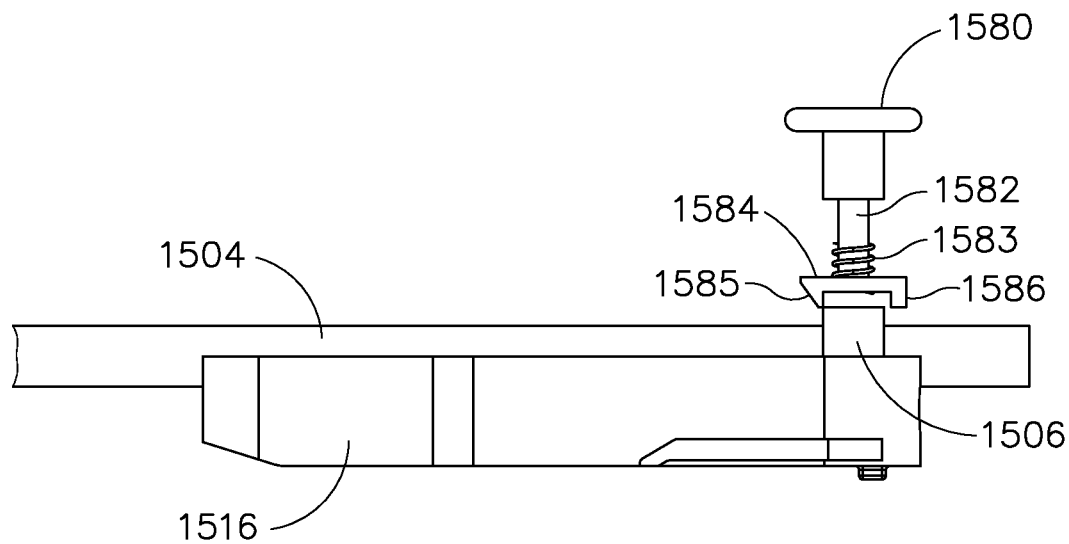
FIG. 90A depicts a side elevational view of the locking assembly of FIG. 89 in an initial position.
Figure 90B:
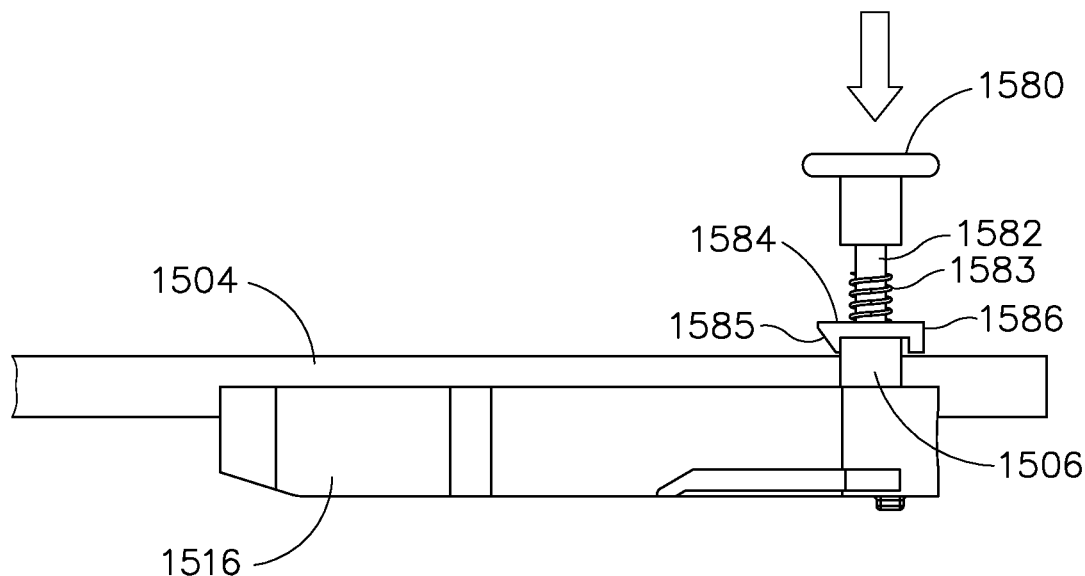
FIG. 90B depicts a side elevational view of the locking assembly of FIG. 89 in an engaged position.

Spring assembly (1580) is positioned in an upward position, as shown in FIG. 90A, such that bracket (1584) does not engage collar (1506) of shaft assembly (1502). Shaft assembly (1502) may thus freely translate within interface assembly (1510). Actuator (1582) may then be released to allow resilient member (1583) to translate pin (1586) downwardly such that bracket (1584) engages collar (1506) of shaft assembly (1502), as shown in FIG. 90B. This maintains the longitudinal alignment of shaft assembly (1502) within interface assembly (1510). Interface assembly (1510) may then be actuated to operate shaft assembly (1502). To remove shaft assembly (1502) from interface assembly (1510), actuator (1582) of spring assembly (1580) is actuated to pull pin (1586) upwardly such that bracket (1584) disengages collar (1506), as shown in FIG. 90A. Shaft assembly (1502) may then freely translate within interface assembly (1510) and be removed from interface assembly (1510). Spring assembly (1510) may thus be readily incorporated with any interface assembly (210, 310, 410, 510, 610, 710, 1310, 1410) described above.

V. Miscellaneous

In any of the foregoing examples, the end effector may be rotatable relative to the shaft assembly and articulation section (in addition to or in lieu of the shaft assembly being rotatable relative to the interface assembly). In some such versions, end effector is independently rotatable in accordance with at least some of the teachings of U.S. Pub. No. 2012/0078247, the disclosure of which is incorporated by reference herein. By way of example only, instruments (400, 500, 600, 700) may readily provide such rotatability by being modified such that helical gear (422, 522, 622, 722) drives rotation of end effector (406, 506, 606, 706) relative to articulation section (404, 504, 604, 704) and shaft assembly (402, 502, 602, 702). Lead screw (403) and nut (407) may thus be omitted. Instead of both drive assemblies (450, 470, 550, 570, 650, 670, 750, 770) of the interface assembly (414, 514, 614, 714) driving articulation of articulation section (404, 504, 604, 704), one drive assembly (450, 470, 550, 570, 650, 670, 750, 770) of the interface assembly (414, 514, 614, 714) may drive articulation while the other drive assembly (450, 470, 550, 570, 650, 670, 750, 770) of the interface assembly (414, 514, 614, 714) drives firing beam (190) (e.g., through a similar rack and pinion configuration). Other suitable ways in which an end effector may be independently rotated (e.g., relative to a shaft assembly and/or relative to an articulation section, etc.) will be apparent to those of ordinary skill in the art in view of the teachings herein.

Examples herein include insertion of a shaft assembly into an interface assembly along a longitudinal axis of the shaft assembly from a proximal side of the interface assembly. It should be understood that some axial insertion techniques may include inserting the shaft assembly from the distal side of the interface assembly instead of approaching from the proximal side. In some versions, a shaft assembly may be inserted into an interface assembly along a path that is transverse to the longitudinal axis of the shaft assembly. It should also be understood that an interface assembly may include an integral power source such as a battery, and that such a battery may provide at least some of any electrical power required to operate the surgical instrument of the interface assembly. In other words, an interface assembly may provide electrical power to one or more components of the associated surgical instrument from a source that is internal to the interface assembly and/or from a source that is external to the interface assembly (e.g., through system (10)). Regardless of where the source is located, the interface assembly may include one or more conductive clips, contacts, and/or other features that provide automatic electrical coupling with the shaft assembly when the shaft assembly is mechanically coupled with the interface assembly. Various suitable ways in which a shaft assembly and an interface assembly may be electrically coupled will be apparent to those of ordinary skill in the art in view of the teachings herein.

Furthermore, an interface assembly may be configured to couple with a variety of types of modular shaft assemblies. Such modular shaft assemblies may provide inter-modality and/or intra-modality variation. Examples of inter-modality variation may include a single interface assembly being able to selectively couple with different shaft assemblies having a variety of end effectors that include staplers, RF electrosurgical features, ultrasonic cutting features, etc. Examples of intra-modality variation may include a single interface assembly being able to selectively couple with different RF electrosurgical shaft assemblies having a variety of end effectors that include straight jaws, curved jaws, etc. Other inter-modality variations and intra-modality variations will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to a surgical stapling instrument, it should be understood that the teachings herein may be combined with the teachings of one or more of the following, the disclosures of all of which are incorporated by reference herein: U.S. Pat. No. 7,380,696; U.S. Pat. No. 7,404,508; U.S. Pat. No. 7,455,208; U.S. Pat. No. 7,506,790; U.S. Pat. No. 7,549,564; U.S. Pat. No. 7,559,450; U.S. Pat. No. 7,654,431; U.S. Pat. No. 7,780,054; U.S. Pat. No. 7,784,662; and/or U.S. Pat. No. 7,798,386. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) an interface assembly for use with a robotic system, wherein the interface assembly comprises:
      (i) a first drive assembly, wherein the interface assembly is configured to receive inputs from an operator to actuate the first drive assembly, and (ii) a mounting plate, wherein the mounting plate comprises an opening, wherein the first drive assembly is positioned within the opening of the mounting plate, wherein the first drive assembly is laterally translatable within the opening from a first position to a second position; and (b) a shaft assembly removably couplable with the interface assembly, wherein the shaft assembly comprises:

(i) an end effector, wherein the first drive assembly of the interface assembly is operable to actuate the end effector of the shaft assembly, and (ii) a first coupling feature, wherein the first coupling feature is configured to longitudinally align with the first drive assembly, wherein the first drive assembly is configured to selectively engage the first coupling feature of the shaft assembly when the first drive assembly is laterally translated from the first position to the second position.

2. The apparatus of claim 1, wherein the shaft assembly is longitudinally translatable within the interface assembly when the first drive assembly is in the first position.

3. The apparatus of claim 2, wherein the shaft assembly is configured to insert distally within a proximal end of the interface assembly.

4. The apparatus of claim 1, wherein the first coupling feature of the shaft assembly comprises a collar.

5. The apparatus of claim 4, wherein the first drive assembly comprises an arm, wherein the arm is configured to engage the collar of the first coupling feature when the first drive assembly is in the second position.

6. The apparatus of claim 1, wherein the interface assembly comprises four drive assemblies.

7. The apparatus of claim 6, wherein each of the four drive assemblies are configured to independently translate within the interface assembly to selectively engage the shaft assembly.

8. The apparatus of claim 1, wherein the interface assembly comprises an actuator to translate the first drive assembly.

9. The apparatus of claim 8, wherein the actuator comprises a rotation knob.

10. The apparatus of claim 9, wherein the rotation knob is coupled with a link, wherein the link is coupled with the first drive assembly, wherein the rotation knob is operable to pivot the link to thereby translate the first drive assembly from the first position to the second position.

11. The apparatus of claim 10 further comprising a screw, wherein the screw is coupled with the rotation knob, wherein a threaded nut is positioned around the screw such that the threaded nut is translatable relative to the screw, wherein the link is pivotably coupled with the threaded nut such that the link is pivotable relative to the threaded nut.

12. The apparatus of claim 10, wherein the rotation knob is coupled with a plate having a curved channel, wherein a portion of the link is translatable within the curved channel of the plate.

13. The apparatus of claim 9, wherein the rotation knob is coupled with a gear assembly, wherein the gear assembly is coupled with a rack, wherein the rack is coupled with the first drive assembly, wherein the rotation knob is operable to rotate the gear assembly to thereby translate the rack and first drive assembly.

14. The apparatus of claim 8, wherein the actuator comprises a pin assembly, wherein the pin assembly is coupled with the first drive assembly, wherein the pin assembly is translatable from a first position to a second position, wherein the pin assembly is operable to translate the first drive assembly when the pin assembly is translated from the first position to the second position.

15. The apparatus of claim 1, wherein the interface assembly comprises a locking assembly, wherein the locking assembly is configured to lock the first drive assembly in the second position.

16. An apparatus for operating on tissue, the apparatus comprising:

(a) an interface assembly for use with a robotic system, wherein the interface assembly comprises:

(i) a first drive assembly, wherein the interface assembly is configured to receive inputs from an operator to actuate the first drive assembly, and (ii) a mounting plate, wherein the mounting plate comprises a bore, wherein the first drive assembly is positioned within the bore of the mounting plate, wherein the first drive assembly is laterally translatable within the bore from a first position to a second position; and (b) a shaft assembly removably couplable with the interface assembly, wherein the shaft assembly comprises:

(i) an end effector, wherein the first drive assembly of the interface assembly is operable to actuate the end effector of the shaft assembly, and (ii) a first coupling feature, wherein the first drive assembly is configured to selectively engage the first coupling feature of the shaft assembly when the first drive assembly is laterally translated from the first position to the second position.

17. The apparatus of claim 16, wherein the shaft assembly further comprises a first gear, wherein the first drive assembly further comprises a second gear.

18. The apparatus of claim 17, wherein the first gear and the second gear are configured to mesh when the first drive assembly is laterally translated from the first position to the second position.

19. The apparatus of claim 18, wherein the first drive assembly is biased towards the second position.

20. An apparatus for operating on tissue, the apparatus comprising:

(a) an interface assembly for use with a robotic system, wherein the interface assembly comprises:

(i) a first drive assembly, wherein the interface assembly is configured to receive inputs from an operator to actuate the first drive assembly, and (ii) a mounting plate, wherein the mounting plate comprises a bore and a resilient member, wherein the first drive assembly is positioned within the bore of the mounting plate, wherein the resilient member is configured to bias the first drive assembly toward a second position, wherein the first drive assembly is translatable within the bore from a first position to the second position; and (b) a shaft assembly removably couplable with the interface assembly, wherein the shaft assembly comprises:

(i) an end effector, wherein the first drive assembly of the interface assembly is operable to actuate the end effector of the shaft assembly, and (ii) a first coupling feature, wherein the first drive assembly is configured to selectively engage the first coupling feature of the shaft assembly when the first drive assembly is translated from the first position to the second position.

* * * * *